(12) United States Patent
Huganir et al.

(10) Patent No.: US 6,723,838 B1
(45) Date of Patent: Apr. 20, 2004

(54) SIGNAL TRANSDUCING SYNAPTIC MOLECULES AND USES THEREOF

(75) Inventors: Richard L. Huganir, Baltimore, MD (US); Jee Hae Kim, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/294,298

(22) Filed: Apr. 19, 1999

Related U.S. Application Data
(60) Provisional application No. 60/082,690, filed on Apr. 22, 1998, and provisional application No. 60/082,717, filed on Apr. 23, 1998.

(51) Int. Cl.[7] .............................................. C07H 21/04
(52) U.S. Cl. ..................................................... 536/23.5
(58) Field of Search ............................ 536/23.5, 24.33; 435/320, 252.3, 69.1

(56) References Cited

U.S. PATENT DOCUMENTS

| | | | |
|---|---|---|---|
| 5,384,242 A | * | 1/1995 | Oakes |
| 5,496,705 A | | 3/1996 | Sugano |
| 5,629,325 A | | 5/1997 | Lin et al. |
| 5,661,024 A | | 8/1997 | Kao et al. |
| 5,693,476 A | | 12/1997 | Scheller |
| 5,707,649 A | | 1/1998 | Inokuchi et al. |

OTHER PUBLICATIONS

Chen et al., Society for Neuroscience, Abstracts, 27th Annual Meeting, Oct. 25–30, 1997, 578.10.*
Sambrook et al. 1989. Molecular Cloning: A Laboratory Manual, Cold Spring Harbor Laboratory Press, Cold Spring Harbor, Chapter 17.*
Skolnick et al., Trends in Biotechnology, vol. 18(1):34–39, Jan. 2000.*
M. Takeuchi, et al. "SAPAPs A Family of PSD–95/SAP90–Associated Proteins Localized at Postsynaptic Density", The Journal Of Biological Chemistry, vol. 272, No. 18, May 2, 1997, pp. 11943–11951.
B. Müller, et al. "SAP102, a Novel Postsynaptic Protein That Interacts With NMDA Receptor Complexes In Vivo", Neuron, vol. 17, Aug., 1996, pp. 255–265.
M. D. Ehlers, et al. "Synaptic Targeting of Glutamate Receptors", Current Opinion in Cell Biology, 1996, 8: pp. 484–489.
Mary B. Kennedy "Origin of PDZ (DHR, GLGF) Domains", TIBS, 20, 1995, p. 350.
H. Dong, et al. "GRIP: a Synaptic PDZ Domain–Containing Protein That Interacts With AMPA Receptors", Nature, vol. 386, Mar. 20, 1997, pp. 279–284.
Craig D. Blackstone, et al. "Biochemical Characterization and Localization of a Non–N–Methyl–D–Aspartate Glutamate Receptor in Rat Brain", Journal of Neurochemistry, vol. 58, No. 3, 1992, pp. 1118–1126.
R. Brambilla, et al. "A Role For the Ras Signalling Pathway In Synaptic Transmission and Long–Term Memory", Nature, vol. 390, Nov. 20, 1997, pp. 281–286.
G. Shaw "The Pleckstrin Homology Domain: An Intriguing Multifunctional Protein Module", BioEssays, vol. 18, No. 1, 1996, pp. 35–46.
Jay E. Brenman et al., "Interaction of Nitric Oxide Synthase With The Postsynaptic Density Protein PSD–95 and 1–Syntrophin Mediated by PDZ Domiains,", Cell, vol. 84, Mar. 8, 1996, pp. 757–767.
J. Saras, et al. "PDZ Domains Bind Carboxy–Terminal Sequences Of Target Proteins", TIBS 21, Dec., 1996, pp. 455–458.
S. Gomperts "Clustering Membrane Proteins: It's All Coming Together With The PSD–95/SAP90 Protein Family", Cell, vol. 84, Mar. 8, 1996, pp. 659–662.
H. Kornau, et al. "Domain Interaction Between NMDA Receptor Subunits and the Postsynaptic Density Protein PSD–95", Science, vol. 269, Sep. 22, 1995, pp. 1737–1740.
K. Scheffzek, et al. "The Ras–RasGAP Complex: Structural Basis For GTPase Activation And Its Loss In Oncogenic Ras Mutants", Science, vol. 277, Jul. 18, 1997, pp. 333–338.
W. G. Tingley et al., "Regulation of NMDA Receptor Phosphorylation By Alternative Splicing of the C–Terminal Domain", Nature, vol. 364, Jul. 1, 1993, pp. 70–73.
M. Sheng, "PDZs And Receptor/Channel Clustering: Rounding Up The Latest Suspects", Neuron, vol. 17, Oct., 1996, pp. 575–578.
C. J. Marshall "Ras Effectors", Current Opinion in Cell Biology, vol. 8, 1996, pp. 197–204.
Mary B. Kennedy "The Postsynaptic Density At Glutamatergic Synapses", TINS, vol. 20, No. 6, 1997, pp. 264–268.
Ulrich Thomas, et al. "Synaptic Clustering Of the Cell Adhesion Molecule Fasciclin II by Discs–Large And Its Role In The Regulation Of Presynaptic Structure", Neuron, vol. 19, Oct., 1997, pp. 787–799.

* cited by examiner

Primary Examiner—Patrick J. Nolan
(74) Attorney, Agent, or Firm—Edwards & Angell, LLP; Peter F. Corless; Robert L. Buchanan

(57) ABSTRACT

The present invention features molecules that relate to SYNGAP (Synaptic GTPase Activating Protein), an excitatory synapse protein that has been found to bind synaptic proteins and modulate signal transduction. In one aspect, the invention provides isolated polynucleotides that encode SYNGAP or fragments or derivatives thereof. Further provided are SYNGAP or SYNGAP-related polypeptides encoded by the polynucleotides. In another aspect, the invention provides immunological molecules that are capable of binding the polypetides. Additionally provided are methods for using the molocules of this invention, e.g., to treat or prevent a disorder mediated by SYNGAP. The invention also provides screening assays for detecting compounds useful in the diagnosis or treatment of disorders impacted by SYNGAP.

1 Claim, 31 Drawing Sheets

```
         10            20            30            40            50            60
ATG TCC TAT GCC CCC TTC AGA GAT GTA CGG GGA CCC CCT ATG CAC CGA ACC CAA TAC GTT CAT
TAC AGG ATA CGG GGG AAG TCT CTA CAT GCC CCT GGG GGA TAC GTG GCT TGG GTT ATG CAA GTA
 M   S   Y   A   P   F   R   D   V   R   G   P   P   M   H   R   T   Q   Y   V   H 70            80            90           100           110           120
TCC CCG TAT GAC CGT CCC GGT TGG AAC CCC CGG TTC TGC ATC ATC TCT GGG AAC CAG CTG CTC
AGG GGC ATA CTG GCA GGG CCA ACC TTG GGG GCC AAG ACG TAG TAG AGA CCC TTG GTC GAC GAG
 S   P   Y   D   R   P   G   W   N   P   R   F   C   I   I   S   G   N   Q   L   L 130           140           150           160           170           180
ATG CTG GAT GAG GAT GAG ATA CAC CCC CTT CTG ATC CGC GAC CGG AGG AGC GAG TCC AGC CGA
TAC GAC CTA CTC CTA CTC TAT GTG GGG GAA GAC TAG GCG CTG GCC TCC TCG CTC AGG TCG GCT
 M   L   D   E   D   E   I   H   P   L   L   I   R   D   R   R   S   E   S   S   R 190           200           210           220           230           240           250
AAC AAA CTG CTG AGA CGC ACC GTC TCT GTG CCA GTG GAG GGG CGG CCC CAC GGC GAG CAT GAA
TTG TTT GAC GAC TCT GCG TGG CAG AGA CAC GGT CAC CTC CCC GCC GGG GTG CCG CTC GTA CTT
 N   K   L   L   R   R   T   V   S   V   P   V   E   G   R   P   H   G   E   H   E 260           270           280           290           300           310
TAC CAC TTG GGT CGC TCG AGG AGG AAG AGT GTC CCC GGG GGG AAA CAG TAC AGC ATG GAA GCC
ATG GTG AAC CCA GCG AGC TCC TCC TTC TCA CAG GGG CCC CCC TTT GTC ATG TCG TAC CTT CGG
 Y   H   L   G   R   S   R   R   K   S   V   P   G   G   K   Q   Y   S   M   E   A 320           330           340           350           360           370
GCC CCC GCT GCG CCC TTC CGG CCC TCG CAA GGC TTC CTG AGC CGG AGG CTA AAA AGC TCC ATC
CGG GGG CGA CGC GGG AAG GCC GGG AGC GTT CCG AAG GAC TCG GCC TCC GAT TTT TCG AGG TAG
 A   P   A   A   P   F   R   P   S   Q   G   F   L   S   R   R   L   K   S   S   I 380           390           400           410           420           430           440
AAA CGT ACA AAG TCA CAA CCC AAA CTT GAC CGG ACC AGC AGC TTT CGA CAG ATC CTG CCT CGC
TTT GCA TGT TTC AGT GTT GGG TTT GAA CTG GCC TGG TCG TCG AAA GCT GTC TAG GAC GGA GCG
 K   R   T   K   S   Q   P   K   L   D   R   T   S   S   F   R   Q   I   L   P   R 450           460           470           480           490           500
TTC CGA AGT GCT GAC CAT GAC CGG GCC CGG CTG ATG CAG AGC TTC AAG GAG TCT CAC TCC CAT
AAG GCT TCA CGA CTG GTA CTG GCC CGG GCC GAC TAC GTC TCG AAG TTC CTC AGA GTG AGG GTA
 F   R   S   A   D   H   D   R   A   R   L   M   Q   S   F   K   E   S   H   S   H 510           520           530           540           550           560
GAG TCC CTG CTG AGT CCC AGC AGT GCT GCT GAG GCC CTG GAG CTC AAC CTG GAT GAA GAC TCC
CTC AGG GAC GAC TCA GGG TCG TCA CGA CGA CTC CGG GAC CTC GAG TTG GAC CTA CTT CTG AGG
 E   S   L   L   S   P   S   S   A   A   E   A   L   E   L   N   L   D   E   D   S 570           580           590           600           610           620           630
ATT ATC AAG CCA GTA CAC AGC TCC ATC CTG GGC CAG GAG TTC TGC TTT GAG GTA ACA ACA TCG
TAA TAG TTC GGT CAT GTG TCG AGG TAG GAC CCG GTC CTC AAG ACG AAA CTC CAT TGT TGT AGC
 I   I   K   P   V   H   S   S   I   L   G   Q   E   F   C   F   E   V   T   T   S 640           650           660           670           680           690
TCT GGG ACA AAA TGT TTT GCC TGT CGG TCT GCA GCC GAA AGG GAC AAA TGG ATT GAG AAT CTA
AGA CCC TGT TTT ACA AAA CGG ACA GCC AGA CGT CGG CTT TCC CTG TTT ACC TAA CTC TTA GAT
 S   G   T   K   C   F   A   C   R   S   A   A   E   R   D   K   W   I   E   N   L
```

FIGURE 1A

```
         700         710         720         730         740         750
          *           *           *           *           *           *
CAG AGG GCT GTG AAA CCC AAC AAG GAC AAC AGC CGC CGG GTA GAT AAC GTG CTG AAA CTA TGG
GTC TCC CGA CAC TTT GGG TTG TTC CTG TTG TCG GCG GCC CAT CTA TTG CAC GAC TTT GAT ACC
 Q   R   A   V   K   P   N   K   D   N   S   R   R   V   D   N   V   L   K   L   W 780         790         800         810         820         830
          *           *           *           *           *           *
ATC ATA GAA GCT CGA GAG CTG CCC CCC AAG AAG CGA TAT TAC TGC GAG TTA TGC CTG GAC GAC
TAG TAT CTT CGA GCT CTC GAC GGG GGG TTC TTC GCT ATA ATG ACG CTC AAT ACG GAC CTG CTG
 I   I   E   A   R   E   L   P   P   K   K   R   Y   Y   C   E   L   C   L   D   D 820         830         840         850         860         870         880
  *           *           *           *           *           *           *
ATG CTC TAT GCA CGG ACC ACT TCC AAG CCC CGC TCA GCC TCA GGA GAC ACT GTC TTT TGG GGC
TAC GAG ATA CGT GCC TGG TGA AGG TTC GGG GCG AGT CGG AGT CCT CTG TGA CAG AAA ACC CCG
 M   L   Y   A   R   T   T   S   K   P   R   S   A   S   G   D   T   V   F   W   G 890         900         910         920         930         940
          *           *           *           *           *           *
GAG CAC TTC GAG TTT AAC AAC CTG CCT GCT GTC CGG GCG CTG CGG CTG CAT CTG TAC CGT GAC
CTC GTG AAG CTC AAA TTG TTG GAC GGA CGA CAG GCC CGC GAC GCC GAC GTA GAC ATG GCA CTG
 E   H   F   E   F   N   N   L   P   A   V   R   A   L   R   L   H   L   Y   R   D 950         960         970         980         990        1000
          *           *           *           *           *           *
TCG GAC AAA AAG CGG AAG AAG GAC AAG GCA GGC TAC GTT GGC CTG GTG ACT GTT CCA GTG GCC
AGC CTG TTT TTC GCC TTC TTC CTG TTC CGT CCG ATG CAA CCG GAC CAC TGA CAA GGT CAC CGG
 S   D   K   K   R   K   K   D   K   A   G   Y   V   G   L   V   T   V   P   V   A 1010        1020        1030        1040        1050        1060        1070
  *           *           *           *           *           *           *
ACC CTG GCT GGG CGC CAC TTC ACA GAG CAG TGG TAC CCC GTG ACC CTG CCA ACA GGA AGT GGG
TGG GAC CGA CCC GCG GTG AAG TGT CTC GTC ACC ATG GGG CAC TGG GAC GGT TGT CCT TCA CCC
 T   L   A   G   R   H   F   T   E   Q   W   Y   P   V   T   L   P   T   G   S   G 1080        1090        1100        1110        1120        1130
          *           *           *           *           *           *
GGC TCT GGG GGT ATG GGC TCG GGG GGA GGA GGG GGG TCA GGG GGC GGC TCA GGG GGC AAA GGG
CCG AGA CCC CCA TAC CCG AGC CCC CCT CCT CCC CCC AGT CCC CCG CCG AGT CCC CCG TTT CCC
 G   S   G   G   M   G   S   G   G   G   G   S   G   G   G   S   G   G   K   G 1140        1150        1160        1170        1180        1190
          *           *           *           *           *           *
AAA GGA GGC TGT CCT GCT GTG CGG CTG AAG GCC CGT TAC CAG ACA ATG AGT ATC CTG CCC ATG
TTT CCT CCG ACA GGA CGA CAC GCC GAC TTC CGG GCA ATG GTC TGT TAC TCA TAG GAC GGG TAC
 K   G   G   C   P   A   V   R   L   K   A   R   Y   Q   T   M   S   I   L   P   M 1200        1210        1220        1230        1240        1250        1260
  *           *           *           *           *           *           *
GAG CTA TAT AAG GAG TTT GCA GAA TAT GTG ACC AAC CAC TAC CGC ATG CTG TGT GCC GTG CTG
CTC GAT ATA TTC CTC AAA CGT CTT ATA CAC TGG TTG GTG ATG GCG TAC GAC ACA CGG CAC GAC
 E   L   Y   K   E   F   A   E   Y   V   T   N   H   Y   R   M   L   C   A   V   L 1270        1280        1290        1300        1310        1320
          *           *           *           *           *           *
GAG CCC GCC CTC AAT GTC AAG GGC AAG GAG GAG GTC GCT AGT GCA CTG GTT CAC ATC CTG CAA
CTC GGG CGG GAG TTA CAG TTC CCG TTC CTC CTC CAG CGA TCA CGT GAC CAA GTG TAG GAC GTT
 E   P   A   L   N   V   K   G   K   E   E   V   A   S   A   L   V   H   I   L   Q 1330        1340        1350        1360        1370        1380
          *           *           *           *           *           *
AGC ACA GGC AAG GCC AAG GAC TTC CTT TCA GAC ATG GCC ATG TCA GAG GTA GAC CGG TTC ATG
TCG TGT CCG TTC CGG TTC CTG AAG GAA AGT CTG TAC CGG TAC AGT CTC CAT CTG GCC AAG TAC
 S   T   G   K   A   K   D   F   L   S   D   M   A   M   S   E   V   D   R   F   M
```

FIGURE 1B

```
     1390          1400         1410         1420         1430         1440
       •             •            •            •            •            •
GAG CGG GAA CAC CTC ATA TTC CGC GAG AAC ACG CTC GCC ACT AAA GCC ATA GAA GAG TAT ATG
CTC GCC CTT GTG GAG TAT AAG GCG CTC TTG TGC GAG CGG TGA TTT CGG TAT CTT CTC ATA TAC
 E   R   E   H   L   I   F   R   E   N   T   L   A   T   K   A   I   E   E   Y   M 1450          1460         1470         1480         1490         1500         1510
       •             •            •            •            •            •            •
AGA CTG ATT GGC CAG AAA TAC CTC AAG GAT GCC ATT GGG GAG TTC ATC CGG GCT CTG TAT GAA
TCT GAC TAA CCG GTC TTT ATG GAG TTC CTA CGG TAA CCC CTC AAG TAG GCC CGA GAC ATA CTT
 R   L   I   G   Q   K   Y   L   K   D   A   I   G   E   F   I   R   A   L   Y   E 1520         1530         1540         1550         1560         1570
            •            •            •            •            •            •
TCT GAG GAG AAC TGT GAA GTA GAC CCC ATC AAG TGC ACA GCG TCC AGT CTG GCA GAG CAC CAG
AGA CTC CTC TTG ACA CTT CAT CTG GGG TAG TTC ACG TGT CGC AGG TCA GAC CGT CTC GTG GTC
 S   E   E   N   C   E   V   D   P   I   K   C   T   A   S   S   L   A   E   H   Q 1580         1590         1600         1610         1620         1630
       •            •            •            •            •            •
GCC AAC CTG CGG ATG TGC TGT GAG TTG GCC CTG TGC AAG GTG GTC AAC TCC CAT TGC GTG TTC
CGG TTG GAC GCC TAC ACG ACA CTC AAC CGG GAC ACG TTC CAC CAG TTG AGG GTA ACG CAC AAG
 A   N   L   R   M   C   C   E   L   A   L   C   K   V   V   N   S   H   C   V   F 1640         1650         1660         1670         1680         1690         1700
   •            •            •            •            •            •            •
CCG AGG GAG CTG AAG GAG GTG TTT GCA TCA TGG CGG CTG CGC TGT GCA GAG CGG GGC CGG GAG
GGC TCC CTC GAC TTC CTC CAC AAA CGT AGT ACC GCC GAC GCG ACA CGT CTC GCC CCG GCC CTC
 P   R   E   L   K   E   V   F   A   S   W   R   L   R   C   A   E   R   G   R   E 1710         1720         1730         1740         1750         1760
            •            •            •            •            •            •
GAC ATT GCT GAC AGG CTG ATC AGC GCC TCG CTC TTC CTG CGC TTC CTC TGC CCG GCC ATC ATG
CTG TAA CGA CTG TCC GAC TAG TCG CGG AGC GAG AAG GAC GCG AAG GAG ACG GGC CGG TAG TAC
 D   I   A   D   R   L   I   S   A   S   L   F   L   R   F   L   C   P   A   I   M 1770         1780         1790         1800         1810         1820
       •            •            •            •            •            •
TCG CCC AGT CTG TTT GGA CTG ATG CAG GAG TAC CCA GAT GAG CAG ACC TCA CGA ACC CTC ACC
AGC GGG TCA GAC AAA CCT GAC TAC GTC CTC ATG GGT CTA CTC GTC TGG AGT GCT TGG GAG TGG
 S   P   S   L   F   G   L   M   Q   E   Y   P   D   E   Q   T   S   R   T   L   T 1830         1840         1850         1860         1870         1880         1890
       •            •            •            •            •            •            •
CTC ATC GCC AAG GTT ATC CAG AAC CTG GCC AAC TTT TCC AAG TTT ACC TCA AAG GAG GAC TTC
GAG TAG CGG TTC CAA TAG GTC TTG GAC CGG TTG AAA AGG TTC AAA TGG AGT TTC CTC CTG AAG
 L   I   A   K   V   I   Q   N   L   A   N   F   S   K   F   T   S   K   E   D   F 1900         1910         1920         1930         1940         1950
            •            •            •            •            •            •
CTG GGC TTC ATG AAC GAG TTT CTG GAG CTG GAG TGG GGT TCT ATG CAG CAA TTC TTG TAT GAG
GAC CCG AAG TAC TTG CTC AAA GAC CTC GAC CTC ACC CCA AGA TAC GTC GTT AAG AAC ATA CTC
 L   G   F   M   N   E   F   L   E   L   E   W   G   S   M   Q   Q   F   L   Y   E 1960         1970         1980         1990         2000         2010
       •            •            •            •            •            •
ATA TCC AAC CTG GAC ACA CTG ACC AAC AGC AGT TTT GAG GGC TAC ATA GAC TTG GGC CGC
TAT AGG TTG GAC CTG TGT GAC TGG TTG TCG TCG TCA AAA CTC CCG ATG TAT CTG AAC CCG GCG
 I   S   N   L   D   T   L   T   N   S   S   S   F   E   G   Y   I   D   L   G   R 2020         2030         2040         2050         2060         2070
       •            •            •            •            •            •
GAG CTC TCC ACA CTT CAC GCC CTG CTC TGG GAG GTG CTG CCC CAG CTC AGC AAG GAA GCC CTC
CTC GAG AGG TGT GAA GTG CGG GAC GAG ACC CTC CAC GAC GGG GTC GAG TCG TTC CTT CGG GAG
 E   L   S   T   L   H   A   L   L   W   E   V   L   P   Q   L   S   K   E   A   L
```

FIGURE 1C

```
2080        2090        2100        2110        2120        2130        2140
 *           *           *           *           *           *           *
CTG AAG CTG GGC CCG CTG CCC CGG CTC CTC AGC GAC ATC AGC ACA GCC CTG AGG AAC CCT AAC
GAC TTC GAC CCG GGC GAC GGG GCC GAG GAG TCG CTG TAG TCG TGT CGG GAC TCC TTG GGA TTG
 L   K   L   G   P   L   P   R   L   L   S   D   I   S   T   A   L   R   N   P   N 2150        2160        2170        2180        2190        2200
         *           *           *           *           *           *
ATC CAA AGG CAG CCG AGC CGC CAG AGC GAG CGC GCT CGG TCT CAG CCC ATG GTG CTG CGC GGG
TAG GTT TCC GTC GGC TCG GCG GTC TCG CTC GCG CGA GCC AGA GTC GGG TAC CAC GAC GCG CCC
 I   Q   R   Q   P   S   R   Q   S   E   R   A   R   S   Q   P   M   V   L   R   G 2210        2220        2230        2240        2250        2260
     *           *           *           *           *           *
CCG TCA GCC GAG ATG CAG GGC TAC ATG ATG CGG GAC CTC AAC AGC TCC ATC GAC CTT CAG TCC
GGC AGT CGG CTC TAC GTC CCG ATG TAC TAC GCC CTG GAG TTG TCG AGG TAG CTG GAA GTC AGG
 P   S   A   E   M   Q   G   Y   M   M   R   D   L   N   S   S   I   D   L   Q   S 2270        2280        2290        2300        2310        2320        2330
 *           *           *           *           *           *           *
TTC ATG GCT CGA GGC CTC AAC AGC TCT ATG GAC ATG GCT CGC CTC CCC TCC CCA ACC AAG GAG
AAG TAC CGA GCT CCG GAG TTG TCG AGA TAC CTG TAC CGA GCG GAG GGG AGG GGT TGG TTC CTC
 F   M   A   R   G   L   N   S   S   M   D   M   A   R   L   P   S   P   T   K   E 2340        2350        2360        2370        2380        2390
         *           *           *           *           *           *
AAA CCC CCG CCG CCC CCT CCC GGT GGG GGT AAA GAC CTG TTC TAT GTG AGC CGG CCA CCA CTG
TTT GGG GGC GGC GGG GGA GGG CCA CCC CCA TTT CTG GAC AAG ATA CAC TCG GCC GGT GGT GAC
 K   P   P   P   P   P   P   G   G   G   K   D   L   F   Y   V   S   R   P   P   L 2400        2410        2420        2430        2440        2450
     *           *           *           *           *           *
GCC CGG TCC TCC CCA GCA TAC TGC ACG AGC AGC TCG GAC ATC ACA GAG CCG GAG CAG AAG ATG
CGG GCC AGG AGG GGT CGT ATG ACG TGC TCG TCG AGC CTG TAG TGT CTC GGC CTC GTC TTC TAC
 A   R   S   S   P   A   Y   C   T   S   S   S   D   I   T   E   P   E   Q   K   M 2460        2470        2480        2490        2500        2510        2520
 *           *           *           *           *           *           *
CTG AGT GTC AAC AAG AGT GTG TCC ATG CTG GAC CTG CAG GGC GAC GGG CCT GGG GGC CGC CTT
GAC TCA CAG TTG TTC TCA CAC AGG TAC GAC CTG GAC GTC CCG CTG CCC GGA CCC CCG GCG GAA
 L   S   V   N   K   S   V   S   M   L   D   L   Q   G   D   G   P   G   G   R   L 2530        2540        2550        12560       2570        2580
         *           *           *           *           *           *
AAC AGC AGT AGT GTT TCC AAC CTG GCA GCT GTT GGG GAC CTG TTG CAC TCA AGC CAG GCT TCA
TTG TCG TCA TCA CAA AGG TTG GAC CGT CGA CAA CCC CTG GAC AAC GTG AGT TCG GTC CGA AGT
 N   S   S   S   V   S   N   L   A   A   V   G   D   L   L   H   S   S   Q   A   S 2590        2600        2610        2620        2630        2640
     *           *           *           *           *           *
CTG ACA GCA GCC TTG GGG TTG CGG CCT GCA CCT GCC GGG CGC CTC TCC CAA GGG AGT GGC TCT
GAC TGT CGT CGG AAC CCC AAC GCC GGA CGT GGA CGG CCC GCG GAG AGG GTT CCC TCA CCG AGA
 L   T   A   A   L   G   L   R   P   A   P   A   G   R   L   S   Q   G   S   G   S 2650        2660        2670        2680        2690        2700
 *           *           *           *           *           *
TCC ATC ACA GCA GCC GGC ATG CGC CTC AGC CAG ATG GGT GTC ACT ACG GAT GGT GTC CCC GCC
AGG TAG TGT CGT CGG CCG TAC GCG GAG TCG GTC TAC CCA CAG TGA TGC CTA CCA CAG GGG CGG
 S   I   T   A   A   G   M   R   L   S   Q   M   G   V   T   T   D   G   V   P   A 2710        2720        2730        2740        2750        2760        2770
 *           *           *           *           *           *           *
CAG CAA CTG CGC ATC CCT CTT TCC TTC CAG AAC CCT CTC TTC CAT ATG GCT GCC GAT GGA CCA
GTC GTT GAC GCG TAG GGA GAA AGG AAG GTC TTG GGA GAG AAG GTA TAC CGA CGG CTA CCT GGT
 Q   Q   L   R   I   P   L   S   F   Q   N   P   L   F   H   M   A   A   D   G   P
```

FIGURE 1D

```
           2780          2790          2800          2810          2820          2830
             •             •             •             •             •             •
GGG CCC CCA GCA GGC CAT GGA GGG AGC AGT GGC CAT GGT CCA CCT TCC TCC CAT CAC CAC CAC
CCC GGG GGT CGT CCG GTA CCT CCC TCG TCA CCG GTA CCA GGT GGA AGG AGG GTA GTG GTG GTG
 G   P   P   A   G   H   G   G   S   S   G   H   G   P   P   S   S   H   H   H   H 2840          2850          2860          2870          2880          2890
             •             •             •             •             •             •
CAC CAC CAT CAC CAT CAC CGA GGG GGA GAA CCC CCA GGG GAC ACT TTT GCC CCG TTC CAT GGC
GTG GTG GTA GTG GTA GTG GCT CCC CCT CTT GGG GGT CCC CTG TGA AAA CGG GGC AAG GTA CCG
 H   H   H   H   H   H   R   G   G   E   P   P   G   D   T   F   A   P   F   H   G 2900          2910          2920          2930          2940          2950          2960
       •             •             •             •             •             •             •
TAT AGC AAG AGC GAG GAC CTC TCT ACA GGG GTC CCT AAG CCC CCT GCG GCC TCC ATC CTT CAC
ATA TCG TTC TCG CTC CTG GAG AGA TGT CCC CAG GGA TTC GGG GGA CGC CGG AGG TAG GAA GTG
 Y   S   K   S   E   D   L   S   T   G   V   P   K   P   P   A   A   S   I   L   H 2970          2980          2990          3000          3010          3020
             •             •             •             •             •             •
AGC CAC AGC TAC AGT GAT GAG TTT GGA CCC TCT GGT ACT GAT TTT ACC CGT CGG CAG CTC TCA
TCG GTG TCG ATG TCA CTA CTC AAA CCT GGG AGA CCA TGA CTA AAA TGG GCA GCC GTC GAG AGT
 S   H   S   Y   S   D   E   F   G   P   S   G   T   D   F   T   R   R   Q   L   S 3030          3040          3050          3060          3070          3080
             •             •             •             •             •             •
CTT CAG GAC AAC CTA CAG CAC ATG CTC TCC CCG CCC CAG ATC ACC ATC GGT CCC CAG AGG CCA
GAA GTC CTG TTG GAT GTC GTG TAC GAG AGG GGC GGG GTC TAG TGG TAG CCA GGG GTC TCC GGT
 L   Q   D   N   L   Q   H   M   L   S   P   P   Q   I   T   I   G   P   Q   R   P 3090          3100          3110          3120          3130          3140          3150
   •             •             •             •             •             •             •
GCT CCC TCA GGG CCA GGA GGG GGC AGT GGT GGG GGC AGT GGT GGG GGC GGT GGG GGC CAG CCA
CGA GGG AGT CCC GGT CCT CCC CCG TCA CCA CCC CCG TCA CCA CCC CCG CCA CCC CCG GTC GGT
 A   P   S   G   P   G   G   G   S   G   G   G   S   G   G   G   G   G   G   Q   P 3160          3170          3180          3190          3200          3210
             •             •             •             •             •             •
CCT CCC TTG CAG AGG GGC AAA TCT CAG CAG TTG ACA GTG AGT GCT GCC CAG AAA CCC CGG CCG
GGA GGG AAC GTC TCC CCG TTT AGA GTC GTC AAC TGT CAC TCA CGA CGG GTC TTT GGG GCC GGC
 P   P   L   Q   R   G   K   S   Q   Q   L   T   V   S   A   A   Q   K   P   R   P 3220          3230          3240          3250          3260          3270
             •             •             •             •             •             •
TCC AGC GGG AAC CTA TTG CAG TCC CCG GAA CCA AGT TAT GGT CCT GCC CGT CCA CGG CAA CAG
AGG TCG CCC TTG GAT AAC GTC AGG GGC CTT GGT TCA ATA CCA GGA CGG GCA GGT GCC GTT GTC
 S   S   G   N   L   L   Q   S   P   E   P   S   Y   G   P   A   R   P   R   Q   Q 3280          3290          3300          3310          3320          3330
             •             •             •             •             •             •
AGC CTC AGC AAA GAG GGC AGC ATT GGG GGC AGC GGG GGC AGC GGT GGC GGA GGG GGT GGG GGG
TCG GAG TCG TTT CTC CCG TCG TAA CCC CCG TCG CCC CCG TCG CCA CCG CCT CCC CCA CCC CCC
 S   L   S   K   E   G   S   I   G   G   S   G   G   S   G   G   G   G   G   G   G 3340          3350          3360          3370          3380          3390          3400
             •             •             •             •             •             •             •
CTC AAG CCC TCC ATC ACC AAG CAG CAT TCC CAG ACT CCA TCC ACG CTG AAC CCC ACG ATG CCG
GAG TTC GGG AGG TAG TGG TTC GTC GTA AGG GTC TGA GGT AGG TGC GAC TTG GGG TGC TAC GGC
 L   K   P   S   I   T   K   Q   H   S   Q   T   P   S   T   L   N   P   T   M   P 3410          3420          3430          3440          3450          3460
             •             •             •             •             •             •
GCC TCG GAG CGG ACT GTA GCC TGG GTG TCC AAT ATG CCT CAC CTG TCC GCT GAC ATC GAG AGT
CGG AGC CTC GCC TGA CAT CGG ACC CAC AGG TTA TAC GGA GTG GAC AGG CGA CTG TAG CTC TCA
 A   S   E   R   T   V   A   W   V   S   N   M   P   H   L   S   A   D   I   E   S
```

FIGURE 1E

```
      3470            3480            3490            3500            3510            3520
        •               •               •               •               •               •
GCA CAC ATT GAG CGG GAA GAG TAC AAG CTG AAG GAG TAC TCG AAG TCC ATG GAC GAG AGC CGA
CGT GTG TAA CTC GCC CTT CTC ATG TTC GAC TTC CTC ATG AGC TTC AGG TAC CTG CTC TCG GCT
 A   H   I   E   R   E   E   Y   K   L   K   E   Y   S   K   S   M   D   E   S   R 3530            3540            3550            3560            3570            3580            3590
    •               •               •               •               •               •               •
CTG GAC AGG GTG AAG GAG TAC GAG GAG GAG ATC CAC TCA CTG AAG GAA AGG CTA CAC ATG TCC
GAC CTG TCC CAC TTC CTC ATG CTC CTC CTC TAG GTG AGT GAC TTC CTT TCC GAT GTG TAC AGG
 L   D   R   V   K   E   Y   E   E   E   I   H   S   L   K   E   R   L   H   M   S 3600            3610            3620            3630            3640            3650
              •               •               •               •               •               •
AAC CGG AAG CTG GAA GAG TAC GAG CGG AGG CTG CTG TCC CAG GAA GAG CAG ACC AGC AAG ATC
TTG GCC TTC GAC CTT CTC ATG CTC GCC TCC GAC GAC AGG GTC CTT CTC GTC TGG TCG TTC TAG
 N   R   K   L   E   E   Y   E   R   R   L   L   S   Q   E   E   Q   T   S   K   I 3660            3670            3680            3690            3700            3710
        •               •               •               •               •               •
CTG ATG CAG TAC CAA GCC CGC CTG GAG CAG AGC GAG AAG CGC TTG AGG CAG CAG CAG GTG GAG
GAC TAC GTC ATG GTT CGG GCG GAC CTC GTC TCG CTC TTC GCG AAC TCC GTC GTC GTC CAC CTC
 L   M   Q   Y   Q   A   R   L   E   Q   S   E   K   R   L   R   Q   Q   Q   V   E 3720            3730            3740            3750            3760            3770            3780
  •               •               •               •               •               •               •
AAG GAC TCC CAG ATC AAG AGC ATC ATT GGC AGG CTG ATG CTG GTG GAG GAG GAG CTG CGC CGG
TTC CTG AGG GTC TAG TTC TCG TAG TAA CCG TCC GAC TAC GAC CAC CTC CTC CTC GAC GCG GCC
 K   D   S   Q   I   K   S   I   I   G   R   L   M   L   V   E   E   E   L   R   R 3790            3800            3810            3820            3830            3840
              •               •               •               •               •               •
GAC CAC CCC GCC ATG GCT GAG CCG CTG CCT GAA CCC AAG AAG AGG CTG CTC GAC GCT CAG AGA
CTG GTG GGG CGG TAC CGA CTC GGC GAC GGA CTT GGG TTC TTC TCC GAC GAG CTG CGA GTC TCT
 D   H   P   A   M   A   E   P   L   P   E   P   K   K   R   L   L   D   A   Q   R 3850            3860            3870            3880            3890            3900
        •               •               •               •               •               •
GGC AGC TTC CCC CCT TGG GTC CAA CAA ACC CGC GTG TGA CGC TGG CCC CAC CTT GGA ACG GCC
CCG TCG AAG GGG GGA ACC CAG GTT GTT TGG GCG CAC ACT GCG ACC GGG GTG GAA CCT TGC CGG
 G   S   F   P   P   W   V   Q   Q   T   R   V   *   R   W   P   H   L   G   T   A 3910            3920            3930            3940            3950            3960
  •               •               •               •               •               •
TGG CCC CCC CAG CCC CAC CCC CCC CAC CCC GGC TGC AGA TCA CAG AGA ACG GCG AGT TCC GGA
ACC GGG GGG GTC GGG GTG GGG GGG GTG GGG CCG ACG TCT AGT GTC TCT TGC CGC TCA AGG CCT
 W   P   P   Q   P   H   P   P   H   P   G   C   R   S   Q   R   T   A   S   S   G 3970            3980            3990            4000            4010            4020            4030
  •               •               •               •               •               •               •
ACA CCG CAG ACC ACT AGC CCA CCC AGC ATC ACA GAC CTC CTT CCC TGT GCA CCC TAC CCC GGC
TGT GGC GTC TGG TGA TCG GGT GGG TCG TAG TGT CTG GAG GAA GGG ACA CGT GGG ATG GGG CCG
 T   P   Q   T   T   S   P   P   S   I   T   D   L   L   P   C   A   P   Y   P   G 4040            4050            4060            4070            4080            4090
              •               •               •               •               •               •
CCA CCC AGC GTC ACA GAC CTC CTT CCC AGT GCA CCC GAC CCT GGA ACA TCA CCA ACC ACC AGG
GGT GGG TCG CAG TGT CTG GAG GAA GGG TCA CGT GGG CTG GGA CCT TGT AGT GGT TGG TGG TCC
 P   P   S   V   T   D   L   L   P   S   A   P   D   P   G   T   S   P   T   T   R 4100            4110            4120            4130            4140            4150
        •               •               •               •               •               •
ACT GGA CGT CAC CAA GGG ACA GCG GGA TTG TCT CCC TTA ACG CCT CCT TGG GGC ACC CAT CTG
TGA CCT GCA GTG GTT CCC TGT CGC CCT AAC AGA GGG AAT TGC GGA GGA ACC CCG TGG GTA GAC
 T   G   R   H   Q   G   T   A   G   L   S   P   L   T   P   P   W   G   T   H   L
```

FIGURE 1F

```
       4160           4170           4180           4190           4200           4210           4220
         •              •              •              •              •              •              •
TCA ACC CCA CTG CTC CAT TCC AGG AGG GAG AGT GGG ACC CTC AGC TGC CCT CTC ACC CCA GGA
AGT TGG GGT GAC GAG GTA AGG TCC TCC CTC TCA CCC TGG GAG TCG ACG GGA GAG TGG GGT CCT
 S   T   P   L   L   H   S   R   R   E   S   G   T   L   S   C   P   L   T   P   G 4230           4240           4250           4260           4270
         •              •              •              •              •
CAC CAC CTA CCC CAC ACA GAC CCC TTC ACT CTG GGG TGC TAT CCC CAT CCT
GTG GTG GAT GGG GTG TGT CTG GGG AAG TGA GAC CCC ACG ATA GGG GTA GGA
 H   H   L   P   H   T   D   P   F   T   L   G   C   Y   P   H   P
```

FIGURE 1G

```
         10          20          30          40          50          60
          •           •           •           •           •           •
TAA GGC CCC CCA CCC CGA CCC CGT CAG GGG GCT CCG GTT CAG GTT CCT TGC CCC CTC CTT CCC
ATT CCG GGG GGT GGG GCT GGG GCA GTC CCC CGA GGC CAA GTC CAA GGA ACG GGG GAG GAA GGG
 *   G   P   P   P   R   P   R   Q   G   A   P   V   Q   V   P   C   P   L   L   P 70          80          90         100         110         120
          •           •           •           •           •           •
ACC GCC AGC CTC TCC GCC GCC GCT GCT CTT CCT GCT GCT TTC CGG GGG AAT ACC ACT TGG GTC
TGG CGG TCG GAG AGG CGG CGG CGA CGA GAA GGA CGA CGA AAG GCC CCC TTA TGG TGA ACC CAG
 T   A   S   L   S   A   A   A   A   L   P   A   A   F   R   G   N   T   T   W   V 130         140         150         160         170         180
          •           •           •           •           •           •
GCT CGA GGA GGA AGA GTG TCC CCG GGG GGG AAA CAG TAC AGC ATG GAA GCC GCC CCC GCT GCG
CGA GCT CCT CCT TCT CAC AGG GGC CCC CCC TTT GTC ATG TCG TAC CTT CGG CGG GGG CGA CGC
 A   R   G   G   R   V   S   P   G   G   K   Q   Y   S   M   E   A   A   P   A   A 190         200         210         220         230         240         250
          •           •           •           •           •           •           •
CCC TTC CGG CCC TCG CAA GGC TTC CTG AGC CGG AGG CTA AAA AGC TCC ATC AAA CGT ACA AAG
GGG AAG GCC GGG AGC GTT CCG AAG GAC TCG GCC TCC GAT TTT TCG AGG TAG TTT GCA TGT TTC
 P   F   R   P   S   Q   G   F   L   S   R   R   L   K   S   S   I   K   R   T   K 260         270         280         290         300         310
          •           •           •           •           •           •
TCA CAA CCC AAA CTT GAC CGG ACC AGC AGC TTT CGA CAG ATC CTG CCT CGC TTC CGA AGT GCT
AGT GTT GGG TTT GAA CTG GCC TGG TCG TCG AAA GCT GTC TAG GAC GGA GCG AAG GCT TCA CGA
 S   Q   P   K   L   D   R   T   S   S   F   R   Q   I   L   P   R   F   R   S   A 320         330         340         350         360         370
          •           •           •           •           •           •
GAC CAT GAC CGG GCC CGG CTG ATG CAG AGC TTC AAG GAG TCT CAC TCC CAT GAG TCC CTG CTG
CTG GTA CTG GCC CGG GCC GAC TAC GTC TCG AAG TTC CTC AGA GTG AGG GTA CTC AGG GAC GAC
 D   H   D   R   A   R   L   M   Q   S   F   K   E   S   H   S   H   E   S   L   L 380         390         400         410         420         430         440
          •           •           •           •           •           •           •
AGT CCC AGC AGT GCT GCT GAG GCC CTG GAG CTC AAC CTG GAT GAA GAC TCC ATT ATC AAG CCA
TCA GGG TCG TCA CGA CGA CTC CGG GAC CTC GAG TTG GAC CTA CTT CTG AGG TAA TAG TTC GGT
 S   P   S   S   A   A   E   A   L   E   L   N   L   D   E   D   S   I   I   K   P 450         460         470         480         490         500
          •           •           •           •           •           •
GTA CAC AGC TCC ATC CTG GGC CAG GAG TTC TGC TTT GAG GTA ACA ACA TCG TCT GGG ACA AAA
CAT GTG TCG AGG TAG GAC CCG GTC CTC AAG ACG AAA CTC CAT TGT TGT AGC AGA CCC TGT TTT
 V   H   S   S   I   L   G   Q   E   F   C   F   E   V   T   T   S   S   G   T   K 510         520         530         540         550         560
          •           •           •           •           •           •
TGT TTT GCC TGT CGG TCT GCA GCC GAA AGG GAC AAA TGG ATT GAG AAT CTA CAG AGG GCT GTG
ACA AAA CGG ACA GCC AGA CGT CGG CTT TCC CTG TTT ACC TAA CTC TTA GAT GTC TCC CGA CAC
 C   F   A   C   R   S   A   A   E   R   D   K   W   I   E   N   L   Q   R   A   V 570         580         590         600         610         620         630
          •           •           •           •           •           •           •
AAA CCC AAC AAG GAC AAC AGC CGC CGG GTA GAT AAC GTG CTG AAA CTA TGG ATC ATA GAA GCT
TTT GGG TTG TTC CTG TTG TCG GCG GCC CAT CTA TTG CAC GAC TTT GAT ACC TAG TAT CTT CGA
 K   P   N   K   D   N   S   R   R   V   D   N   V   L   K   L   W   I   I   E   A
```

FIGURE 2A

```
      640           650           660           670           680           690
       •             •             •             •             •             •
CGA GAG CTG CCC CCC AAG AAG CGA TAT TAC TGC GAG TTA TGC CTG GAC GAC ATG CTC TAT GCA
GCT CTC GAC GGG GGG TTC TTC GCT ATA ATG ACG CTC AAT ACG GAC CTG CTG TAC GAG ATA CGT
 R   E   L   P   P   K   K   R   Y   Y   C   E   L   C   L   D   D   M   L   Y   A 700           710           720           730           740           750
       •             •             •             •             •             •
CGG ACC ACT TCC AAG CCC CGC TCA GCC TCA GGA GAC ACT GTC TTT TGG GGC GAG CAC TTC GAG
GCC TGG TGA AGG TTC GGG GCG AGT CGG AGT CCT CTG TGA CAG AAA ACC CCG CTC GTG AAG CTC
 R   T   T   S   K   P   R   S   A   S   G   D   T   V   F   W   G   E   H   F   E 780           790           800           810           820           830
       •             •             •             •             •             •
TTT AAC AAC CTG CCT GCT GTC CGG GCG CTG CGG CTG CAT CTG TAC CGT GAC TCG GAC AAA AAG
AAA TTG TTG GAC GGA CGA CAG GCC CGC GAC GCC GAC GTA GAC ATG GCA CTG AGC CTG TTT TTC
 F   N   N   L   P   A   V   R   A   L   R   L   H   L   Y   R   D   S   D   K   K 820           830           840           850           860           870           880
 •             •             •             •             •             •             •
CGG AAG AAG GAC AAG GCA GGC TAC GTT GGC CTG GTG ACT GTT CCA GTG GCC ACC CTG GCT GGG
GCC TTC TTC CTG TTC CGT CCG ATG CAA CCG GAC CAC TGA CAA GGT CAC CGG TGG GAC CGA CCC
 R   K   K   D   K   A   G   Y   V   G   L   V   T   V   P   V   A   T   L   A   G 890           900           910           920           930           940
             •             •             •             •             •             •
CGC CAC TTC ACA GAG CAG TGG TAC CCC GTG ACC CTG CCA ACA GGA AGT GGG GGC TCT GGG GGT
GCG GTG AAG TGT CTC GTC ACC ATG GGG CAC TGG GAC GGT TGT CCT TCA CCC CCG AGA CCC CCA
 R   H   F   T   E   Q   W   Y   P   V   T   L   P   T   G   S   G   G   S   G   G 950           960           970           980           990           1000
       •             •             •             •             •             •
ATG GGC TCG GGG GGA GGA GGG GGG TCA GGG GGC GGC TCA GGG GGC AAA GGG AAA GGA GGC TGT
TAC CCG AGC CCC CCT CCT CCC CCC AGT CCC CCG CCG AGT CCC CCG TTT CCC TTT CCT CCG ACA
 M   G   S   G   G   G   G   S   G   G   G   S   G   G   K   G   K   G   G   C 1010          1020          1030          1040          1050          1060          1070
 •             •             •             •             •             •             •
CCT GCT GTG CGG CTG AAG GCC CGT TAC CAG ACA ATG AGT ATC CTG CCC ATG GAG CTA TAT AAG
GGA CGA CAC GCC GAC TTC CGG GCA ATG GTC TGT TAC TCA TAG GAC GGG TAC CTC GAT ATA TTC
 P   A   V   R   L   K   A   R   Y   Q   T   M   S   I   L   P   M   E   L   Y   K 1080          1090          1100          1110          1120          1130
           •             •             •             •             •             •
GAG TTT GCA GAA TAT GTG ACC AAC CAC TAC CGC ATG CTG TGT GCC GTG CTG GAG CCC GCC CTC
CTC AAA CGT CTT ATA CAC TGG TTG GTG ATG GCG TAC GAC ACA CGG CAC GAC CTC GGG CGG GAG
 E   F   A   E   Y   V   T   N   H   Y   R   M   L   C   A   V   L   E   P   A   L 1140          1150          1160          1170          1180          1190
       •             •             •             •             •             •
AAT GTC AAG GGC AAG GAG GAG GTC GCT AGT GCA CTG GTT CAC ATC CTG CAA AGC ACA GGC AAG
TTA CAG TTC CCG TTC CTC CTC CAG CGA TCA CGT GAC CAA GTG TAG GAC GTT TCG TGT CCG TTC
 N   V   K   G   K   E   E   V   A   S   A   L   V   H   I   L   Q   S   T   G   K 1200          1210          1220          1230          1240          1250          1260
 •             •             •             •             •             •             •
GCC AAG GAC TTC CTT TCA GAC ATG GCC ATG TCA GAG GTA GAC CGG TTC ATG GAG CGG GAA CAC
CGG TTC CTG AAG GAA AGT CTG TAC CGG TAC AGT CTC CAT CTG GCC AAG TAC CTC GCC CTT GTG
 A   K   D   F   L   S   D   M   A   M   S   E   V   D   R   F   M   E   R   E   H 1270          1280          1290          1300          1310          1320
           •             •             •             •             •             •
CTC ATA TTC CGC GAG AAC ACG CTC GCC ACT AAA GCC ATA GAA GAG TAT ATG AGA CTG ATT GGC
GAG TAT AAG GCG CTC TTG TGC GAG CGG TGA TTT CGG TAT CTT CTC ATA TAC TCT GAC TAA CCG
 L   I   F   R   E   N   T   L   A   T   K   A   I   E   E   Y   M   R   L   I   G
```

FIGURE 2B

```
       1330            1340            1350            1360            1370            1380
         •               •               •               •               •               •
CAG AAA TAC CTC AAG GAT GCC ATT GGG GAG TTC ATC CGG GCT CTG TAT GAA TCT GAG GAG AAC
GTC TTT ATG GAG TTC CTA CGG TAA CCC CTC AAG TAG GCC CGA GAC ATA CTT AGA CTC CTC TTG
 Q   K   Y   L   K   D   A   I   G   E   F   I   R   A   L   Y   E   S   E   E   N 1390            1400            1410            1420            1430            1440
         •               •               •               •               •               •
TGT GAA GTA GAC CCC ATC AAG TGC ACA GCG TCC AGT CTG GCA GAG CAC CAG GCC AAC CTG CGG
ACA CTT CAT CTG GGG TAG TTC ACG TGT CGC AGG TCA GAC CGT CTC GTG GTC CGG TTG GAC GCC
 C   E   V   D   P   I   K   C   T   A   S   L   A   E   H   Q   A   N   L   R 1450            1460            1470            1480            1490            1500            1510
    •               •               •               •               •               •               •
ATG TGC TGT GAG TTG GCC CTG TGC AAG GTG GTC AAC TCC CAT TGC GTG TTC CCG AGG GAG CTG
TAC ACG ACA CTC AAC CGG GAC ACG TTC CAC CAG TTG AGG GTA ACG CAC AAG GGC TCC CTC GAC
 M   C   C   E   L   A   L   C   K   V   V   N   S   H   C   V   F   P   R   E   L 1520            1530            1540            1550            1560            1570
              •               •               •               •               •               •
AAG GAG GTG TTT GCA TCA TGG CGG CTG CGC TGT GCA GAG CGG GGC CGG GAG GAC ATT GCT GAC
TTC CTC CAC AAA CGT AGT ACC GCC GAC GCG ACA CGT CTC GCC CCG GCC CTC CTG TAA CGA CTG
 K   E   V   F   A   S   W   R   L   R   C   A   E   R   G   R   E   D   I   A   D 1580            1590            1600            1610            1620            1630
         •               •               •               •               •               •
AGG CTG ATC AGC GCC TCG CTC TTC CTG CGC TTC CTC TGC CCG GCC ATC ATG TCG CCC AGT CTG
TCC GAC TAG TCG CGG AGC GAG AAG GAC GCG AAG GAG ACG GGC CGG TAG TAC AGC GGG TCA GAC
 R   L   I   S   A   S   L   F   L   R   F   L   C   P   A   I   M   S   P   S   L 1640            1650            1660            1670            1680            1690            1700
         •               •               •               •               •               •               •
TTT GGA CTG ATG CAG GAG TAC CCA GAT GAG CAG ACC TCA CGA ACC CTC ACC CTC ATC GCC AAG
AAA CCT GAC TAC GTC CTC ATG GGT CTA CTC GTC TGG AGT GCT TGG GAG TGG GAG TAG CGG TTC
 F   G   L   M   Q   E   Y   P   D   E   Q   T   S   R   T   L   T   L   I   A   K 1710            1720            1730            1740            1750            1760
              •               •               •               •               •               •
GTT ATC CAG AAC CTG GCC AAC TTT TCC AAG TTT ACC TCA AAG GAG GAC TTC CTG GGC TTC ATG
CAA TAG GTC TTG GAC CGG TTG AAA AGG TTC AAA TGG AGT TTC CTC CTG AAG GAC CCG AAG TAC
 V   I   Q   N   L   A   N   F   S   K   F   T   S   K   E   D   F   L   G   F   M 1770            1780            1790            1800            1810            1820
         •               •               •               •               •               •
AAC GAG TTT CTG GAG CTG GAG TGG GGT TCT ATG CAG CAA TTC TTG TAT GAG ATA TCC AAC CTG
TTG CTC AAA GAC CTC GAC CTC ACC CCA AGA TAC GTC GTT AAG AAC ATA CTC TAT AGG TTG GAC
 N   E   F   L   E   L   E   W   G   S   M   Q   Q   F   L   Y   E   I   S   N   L 1830            1840            1850            1860            1870            1880            1890
    •               •               •               •               •               •               •
GAC ACA CTG ACC AAC AGC AGC AGT TTT GAG GGC TAC ATA GAC TTG GGC CGC GAG CTC TCC ACA
CTG TGT GAC TGG TTG TCG TCG TCA AAA CTC CCG ATG TAT CTG AAC CCG GCG CTC GAG AGG TGT
 D   T   L   T   N   S   S   S   F   E   G   Y   I   D   L   G   R   E   L   S   T 1900            1910            1920            1930            1940            1950
              •               •               •               •               •               •
CTT CAC GCC CTG CTC TGG GAG GTG CTG CCC CAG CTC AGC AAG GAA GCC CTC CTG AAG CTG GGC
GAA GTG CGG GAC GAG ACC CTC CAC GAC GGG GTC GAG TCG TTC CTT CGG GAG GAC TTC GAC CCG
 L   H   A   L   L   W   E   V   L   P   Q   L   S   K   E   A   L   L   K   L   G
```

FIGURE 2C

```
      1960              1970              1980              1990              2000              2010
        *                 *                 *                 *                 *                 *
CCG CTG CCC CGG CTC CTC AGC GAC ATC AGC ACA GCC CTG AGG AAC CCT AAC ATC CAA AGG CAG
GGC GAC GGG GCC GAG GAG TCG CTG TAG TCG TGT CGG GAC TCC TTG GGA TTG TAG GTT TCC GTC
 P   L   P   R   L   L   S   D   I   S   T   A   L   R   N   P   N   I   Q   R   Q 2020              2030              2040              2050              2060              2070
        *                 *                 *                 *                 *                 *
CCG AGC CGC CAG AGC GAG CGC GCT CGG TCT CAG CCC ATG GTG CTG CGC GGG CCG TCA GCC GAG
GGC TCG GCG GTC TCG CTC GCG CGA GCC AGA GTC GGG TAC CAC GAC GCG CCC GGC AGT CGG CTC
 P   S   R   Q   S   E   R   A   R   S   Q   P   M   V   L   R   G   P   S   A   E 2080              2090              2100              2110              2120              2130              2140
        *                 *                 *                 *                 *                 *                 *
ATG CAG GGC TAC ATG ATG CGG GAC CTC AAC AGC TCC ATC GAC CTT CAG TCC TTC ATG GCT CGA
TAC GTC CCG ATG TAC TAC GCC CTG GAG TTG TCG AGG TAG CTG GAA GTC AGG AAG TAC CGA GCT
 M   Q   G   Y   M   M   R   D   L   N   S   S   I   D   L   Q   S   F   M   A   R 2150              2160              2170              2180              2190              2200
        *                 *                 *                 *                 *                 *
GGC CTC AAC AGC TCT ATG GAC ATG GCT CGC CTC CCC TCC CCA ACC AAG GAG AAA CCC CCG CCG
CCG GAG TTG TCG AGA TAC CTG TAC CGA GCG GAG GGG AGG GGT TGG TTC CTC TTT GGG GGC GGC
 G   L   N   S   S   M   D   M   A   R   L   P   S   P   T   K   E   K   P   P   P 2210              2220              2230              2240              2250              2260
        *                 *                 *                 *                 *                 *
CCC CCT CCC GGT GGG GGT AAA GAC CTG TTC TAT GTG AGC CGG CCA CCA CTG GCC CGG TCC TCC
GGG GGA GGG CCA CCC CCA TTT CTG GAC AAG ATA CAC TCG GCC GGT GGT GAC CGG GCC AGG AGG
 P   P   P   G   G   G   K   D   L   F   Y   V   S   R   P   P   L   A   R   S   S 2270              2280              2290              2300              2310              2320              2330
  *                 *                 *                 *                 *                 *                 *
CCA GCA TAC TGC ACG AGC AGC TCG GAC ATC ACA GAG CCG GAG CAG AAG ATG CTG AGT GTC AAC
GGT CGT ATG ACG TGC TCG TCG AGC CTG TAG TGT CTC GGC CTC GTC TTC TAC GAC TCA CAG TTG
 P   A   Y   C   T   S   S   S   D   I   T   E   P   E   Q   K   M   L   S   V   N 2340              2350              2360              2370              2380              2390
              *                 *                 *                 *                 *                 *
AAG AGT GTG TCC ATG CTG GAC CTG CAG GGC GAC GGG CCT GGG GGC CGC CTT AAC AGC AGT AGT
TTC TCA CAC AGG TAC GAC CTG GAC GTC CCG CTG CCC GGA CCC CCG GCG GAA TTG TCG TCA TCA
 K   S   V   S   M   L   D   L   Q   G   D   G   P   G   G   R   L   N   S   S   S 2400              2410              2420              2430              2440              2450
        *                 *                 *                 *                 *                 *
GTT TCC AAC CTG GCA GCT GTT GGG GAC CTG TTG CAC TCA AGC CAG GCT TCA CTG ACA GCA GCC
CAA AGG TTG GAC CGT CGA CAA CCC CTG GAC AAC GTG AGT TCG GTC CGA AGT GAC TGT CGT CGG
 V   S   N   L   A   A   V   G   D   L   L   H   S   S   Q   A   S   L   T   A   A 2460              2470              2480              2490              2500              2510              2520
        *                 *                 *                 *                 *                 *                 *
TTG GGG TTG CGG CCT GCA CCT GCC GGG CGC CTC TCC CAA GGG AGT GGC TCT TCC ATC ACA GCA
AAC CCC AAC GCC GGA CGT GGA CGG CCC GCG GAG AGG GTT CCC TCA CCG AGA AGG TAG TGT CGT
 L   G   L   R   P   A   P   A   G   R   L   S   Q   G   S   G   S   S   I   T   A 2530              2540              2550              12560             2570              2580
              *                 *                 *                 *                 *                 *
GCC GGC ATG CGC CTC AGC CAG ATG GGT GTC ACT ACG GAT GGT GTC CCC GCC CAG CAA CTG CGC
CGG CCG TAC GCG GAG TCG GTC TAC CCA CAG TGA TGC CTA CCA CAG GGG CGG GTC GTT GAC GCG
 A   G   M   R   L   S   Q   M   G   V   T   T   D   G   V   P   A   Q   Q   L   R
```

FIGURE 2D

```
       2590            2600            2610             2620           2630            2640
ATC  CCT CTT TCC TTC CAG AAC CCT CTC TTC CAT ATG GCT GCC GAT GGA CCA GGG CCC CCA GCA
TAG  GGA GAA AGG AAG GTC TTG GGA GAG AAG GTA TAC CGA CGG CTA CCT GGT CCC GGG GGT CGT
 I    P   L   S   F   Q   N   P   L   F   H   M   A   A   D   G   P   G   P   P   A 2650            2660            2670             2680           2690            2700
GGC CAT GGA GGG AGC AGT GGC CAT GGT CCA CCT TCC TCC CAT CAC CAC CAC CAC CAC CAT CAC
CCG GTA CCT CCC TCG TCA CCG GTA CCA GGT GGA AGG AGG GTA GTG GTG GTG GTG GTG GTA GTG
 G   H   G   G   S   S   G   H   G   P   P   S   S   H   H   H   H   H   H   H   H 2710            2720            2730             2740           2750            2760             2770
CAT CAC CGA GGG GGA GAA CCC CCA GGG GAC ACT TTT GCC CCG TTC CAT GGC TAT AGC AAG AGC
GTA GTG GCT CCC CCT CTT GGG GGT CCC CTG TGA AAA CGG GGC AAG GTA CCG ATA TCG TTC TCG
 H   H   R   G   G   E   P   P   G   D   T   F   A   P   F   H   G   Y   S   K   S 2780            2790            2800             2810           2820            2830
GAG GAC CTC TCT ACA GGG GTC CCT AAG CCC CCT GCG GCC TCC ATC CTT CAC AGC CAC AGC TAC
CTC CTG GAG AGA TGT CCC CAG GGA TTC GGG GGA CGC CGG AGG TAG GAA GTG TCG GTG TCG ATG
 E   D   L   S   T   G   V   P   K   P   P   A   A   S   I   L   H   S   H   S   Y 2840            2850            2860             2870           2880            2890
AGT GAT GAG TTT GGA CCC TCT GGT ACT GAT TTT ACC CGT CGG CAG CTC TCA CTT CAG GAC AAC
TCA CTA CTC AAA CCT GGG AGA CCA TGA CTA AAA TGG GCA GCC GTC GAG AGT GAA GTC CTG TTG
 S   D   E   F   G   P   S   G   T   D   F   T   R   R   Q   L   S   L   Q   D   N 2900           2910            2920            2930             2940           2950            2960
CTA CAG CAC ATG CTC TCC CCG CCC CAG ATC ACC ATC GGT CCC CAG AGG CCA GCT CCC TCA GGG
GAT GTC GTG TAC GAG AGG GGC GGG GTC TAG TGG TAG CCA GGG GTC TCC GGT CGA GGG AGT CCC
 L   Q   H   M   L   S   P   P   Q   I   T   I   G   P   Q   R   P   A   P   S   G 2970            2980            2990             3000           3010            3020
CCA GGA GGG GGC AGT GGT GGG GGC AGT GGT GGG GGC GGT GGG GGC CAG CCA CCT CCC TTG CAG
GGT CCT CCC CCG TCA CCA CCC CCG TCA CCA CCC CCG CCA CCC CCG GTC GGT GGA GGG AAC GTC
 P   G   G   G   S   G   G   G   S   G   G   G   G   G   Q   P   P   P   L   Q 3030            3040            3050             3060           3070            3080
AGG GGC AAA TCT CAG CAG TTG ACA GTG AGT GCT GCC CAG AAA CCC CGG CCG TCC AGC GGG AAC
TCC CCG TTT AGA GTC GTC AAC TGT CAC TCA CGA CGG GTC TTT GGG GCC GGC AGG TCG CCC TTG
 R   G   K   S   Q   Q   L   T   V   S   A   A   Q   K   P   R   P   S   S   G   N 3090            3100             3110             3120            3130             3140            3150
CTA TTG CAG TCC CCG GAA CCA AGT TAT GGT CCT GCC CGT CCA CGG CAA CAG AGC CTC AGC AAA
GAT AAC GTC AGG GGC CTT GGT TCA ATA CCA GGA CGG GCA GGT GCC GTT GTC TCG GAG TCG TTT
 L   L   Q   S   P   E   P   S   Y   G   P   A   R   P   R   Q   Q   S   L   S   K 3160            3170            3180             3190           3200            3210
GAG GGC AGC ATT GGG GGC AGC GGG GGC AGC GGT GGC GGA GGG GGT GGG GGG CTC AAG CCC TCC
CTC CCG TCG TAA CCC CCG TCG CCC CCG TCG CCA CCG CCT CCC CCA CCC CCC GAG TTC GGG AGG
 E   G   S   I   G   G   S   G   G   S   G   G   G   G   G   L   K   P   S 3220            3230            3240             3250           3260            3270
ATC ACC AAG CAG CAT TCC CAG ACT CCA TCC ACG CTG AAC CCC ACG ATG CCG GCC TCG GAG CGG
TAG TGG TTC GTC GTA AGG GTC TGA GGT AGG TGC GAC TTG GGG TGC TAC GGC CGG AGC CTC GCC
 I   T   K   Q   H   S   Q   T   P   S   T   L   N   P   T   M   P   A   S   E   R
```

FIGURE 2E

```
      3280           3290           3300           3310           3320           3330
ACT GTA GCC TGG GTG TCC AAT ATG CCT CAC CTG TCC GCT GAC ATC GAG AGT GCA CAC ATT GAG
TGA CAT CGG ACC CAC AGG TTA TAC GGA GTG GAC AGG CGA CTG TAG CTC TCA CGT GTG TAA CTC
 T   V   A   W   V   S   N   M   P   H   L   S   A   D   I   E   S   A   H   I   E 3340           3350           3360           3370           3380           3390           3400
CGG GAA GAG TAC AAG CTG AAG GAG TAC TCG AAG TCC ATG GAC GAG AGC CGA CTG GAC AGG GTG
GCC CTT CTC ATG TTC GAC TTC CTC ATG AGC TTC AGG TAC CTG CTC TCG GCT GAC CTG TCC CAC
 R   E   E   Y   K   L   K   E   Y   S   K   S   M   D   E   S   R   L   D   R   V 3410           3420           3430           3440           3450           3460
AAG GAG TAC GAG GAG GAG ATC CAC TCA CTG AAG GAA AGG CTA CAC ATG TCC AAC CGG AAG CTG
TTC CTC ATG CTC CTC CTC TAG GTG AGT GAC TTC CTT TCC GAT GTG TAC AGG TTG GCC TTC GAC
 K   E   Y   E   E   E   I   H   S   L   K   E   R   L   H   M   S   N   R   K   L 3470           3480           3490           3500           3510           3520
GAA GAG TAC GAG CGG AGG CTG CTG TCC CAG GAA GAG CAG ACC AGC AAG ATC CTG ATG CAG TAC
CTT CTC ATG CTC GCC TCC GAC GAC AGG GTC CTT CTC GTC TGG TCG TTC TAG GAC TAC GTC ATG
 E   E   Y   E   R   R   L   L   S   Q   E   E   Q   T   S   K   I   L   M   Q   Y 3530           3540           3550           3560           3570           3580           3590
CAA GCC CGC CTG GAG CAG AGC GAG AAG CGC TTG AGG CAG CAG CAG GTG GAG AAG GAC TCC CAG
GTT CGG GCG GAC CTC GTC TCG CTC TTC GCG AAC TCC GTC GTC GTC CAC CTC TTC CTG AGG GTC
 Q   A   R   L   E   Q   S   E   K   R   L   R   Q   Q   Q   V   E   K   D   S   Q 3600           3610           3620           3630           3640           3650
ATC AAG AGC ATC ATT GGC AGG CTG ATG CTG GTG GAG GAG GAG CTG CGC CGG GAC CAC CCC GCC
TAG TTC TCG TAG TAA CCG TCC GAC TAC GAC CAC CTC CTC CTC GAC GCG GCC CTG GTG GGG CGG
 I   K   S   I   I   G   R   L   M   L   V   E   E   E   L   R   R   D   H   P   A 3660           3670           3680           3690           3700           3710
ATG GCT GAG CCG CTG CCT GAA CCC AAG AAG AGG CTG CTC GAC GCT CAG AGA GGC AGC TTC CCC
TAC CGA CTC GGC GAC GGA CTT GGG TTC TTC TCC GAC GAG CTG CGA GTC TCT CCG TCG AAG GGG
 M   A   E   P   L   P   E   P   K   K   R   L   L   D   A   Q   R   G   S   F   P 3720           3730           3740           3750           3760           3770           3780
CCT TGG GTC CAA CAA ACC CGC GTG TGA CGC TGG CCC CAC CTT GGA ACG GCC TGG CCC CCC CAG
GGA ACC CAG GTT GTT TGG GCG CAC ACT GCG ACC GGG GTG GAA CCT TGC CGG ACC GGG GGG GTC
 P   W   V   Q   Q   T   *   R   V   R   W   P   H   L   G   T   A   W   P   P   Q 3790           3800           3810           3820           3830           3840
CCC CAC CCC CCC CAC CCC GGC TGC AGA TCA CAG AGA ACG GCG AGT TCC GGA ACA CCG CAG ACC
GGG GTG GGG GGG GTG GGG CCG ACG TCT AGT GTC TCT TGC CGC TCA AGG CCT TGT GGC GTC TGG
 P   H   P   P   H   P   G   C   R   S   Q   R   T   A   S   S   G   T   P   Q   T 3850           3860           3870           3880           3890           3900
ACT AGC CCA CCC AGC ATC ACA GAC CTC CTT CCC TGT GCA CCC TAC CCC GGC CCA CCC AGC GTC
TGA TCG GGT GGG TCG TAG TGT CTG GAG GAA GGG ACA CGT GGG ATG GGG CCG GGT GGG TCG CAG
 T   S   P   P   S   I   T   D   L   L   P   C   A   P   Y   P   G   P   P   S   V
```

FIGURE 2F

```
    3910            3920            3930            3940            3950            3960
      *               *               *               *               *               *
ACA GAC CTC CTT CCC AGT GCA CCC GAC CCT GGA ACA TCA CCA ACC ACC AGG ACT GGA CGT CAC
TGT CTG GAG GAA GGG TCA CGT GGG CTG GGA CCT TGT AGT GGT TGG TGG TCC TGA CCT GCA GTG
 T   D   L   L   P   S   A   P   D   P   G   T   S   P   T   T   R   T   G   R   H 3970            3980            3990            4000            4010            4020            4030
      *               *               *               *               *               *               *
CAA GGG ACA GCG GGA TTG TCT CCC TTA ACG CCT CCT TGG GGC ACC CAT CTG TCA ACC CCA CTG
GTT CCC TGT CGC CCT AAC AGA GGG AAT TGC GGA GGA ACC CCG TGG GTA GAC AGT TGG GGT GAC
 Q   G   T   A   G   L   S   P   L   T   P   P   W   G   T   H   L   S   T   P   L 4040            4050            4060            4070            4080            4090
          *               *               *               *               *               *
CTC CAT TCC AGG AGG GAG AGT GGG ACC CTC AGC TGC CCT CTC ACC CCA GGA CAC CAC CTA CCC
GAG GTA AGG TCC TCC CTC TCA CCC TGG GAG TCG ACG GGA GAG TGG GGT CCT GTG GTG GAT GGG
 L   H   S   R   R   E   S   G   T   L   S   C   P   L   T   P   G   H   H   L   P 4100            4110            4120            4130
      *               *               *               *
CAC ACA GAC CCC TTC ACT CTG GGG TGC TAT CCC CAT CCT
GTG TGT CTG GGG AAG TGA GAC CCC ACG ATA GGG GTA GGA
 H   T   D   P   F   T   L   G   C   Y   P   H   P
```

FIGURE 2G

```
              10           20           30           40           50           60
              *            *            *            *            *            *
TAG GGA GAG ACT GAG CTG CCC CAA GCA CCC CAT TTC CCA TTT GCT CCC CAG CAA GGC TTC CTG
ATC CCT CTC TGA CTC GAC GGG GTT CGT GGG GTA AAG GGT AAA CGA GGG GTC GTT CCG AAG GAC
 *   G   E   T   E   L   P   Q   A   P   H   F   P   F   A   P   Q   Q   G   F   L 70           80           90          100          110          120
              *            *            *            *            *            *
AGC CGG AGG CTA AAA AGC TCC ATC AAA CGT ACA AAG TCA CAA CCC AAA CTT GAC CGG ACC AGC
TCG GCC TCC GAT TTT TCG AGG TAG TTT GCA TGT TTC AGT GTT GGG TTT GAA CTG GCC TGG TCG
 S   R   R   L   K   S   S   I   K   R   T   K   S   Q   P   K   L   D   R   T   S 130          140          150          160          170          180
          *            *            *            *            *            *
AGC TTT CGA CAG ATC CTG CCT CGC TTC CGA AGT GCT GAC CAT GAC CGG GCC CGG CTG ATG CAG
TCG AAA GCT GTC TAG GAC GGA GCG AAG GCT TCA CGA CTG GTA CTG GCC CGG GCC GAC TAC GTC
 S   F   R   Q   I   L   P   R   F   R   S   A   D   H   D   R   A   R   L   M   Q 190          200          210          220          230          240          250
     *            *            *            *            *            *            *
AGC TTC AAG GAG TCT CAC TCC CAT GAG TCC CTG CTG AGT CCC AGC AGT GCT GCT GAG GCC CTG
TCG AAG TTC CTC AGA GTG AGG GTA CTC AGG GAC GAC TCA GGG TCG TCA CGA CGA CTC CGG GAC
 S   F   K   E   S   H   S   H   E   S   L   L   S   P   S   S   A   A   E   A   L 260          270          280          290          300          310
          *            *            *            *            *            *
GAG CTC AAC CTG GAT GAA GAC TCC ATT ATC AAG CCA GTA CAC AGC TCC ATC CTG GGC CAG GAG
CTC GAG TTG GAC CTA CTT CTG AGG TAA TAG TTC GGT CAT GTG TCG AGG TAG GAC CCG GTC CTC
 E   L   N   L   D   E   D   S   I   I   K   P   V   H   S   S   I   L   G   Q   E 320          330          340          350          360          370
          *            *            *            *            *            *
TTC TGC TTT GAG GTA ACA ACA TCG TCT GGG ACA AAA TGT TTT GCC TGT CGG TCT GCA GCC GAA
AAG ACG AAA CTC CAT TGT TGT AGC AGA CCC TGT TTT ACA AAA CGG ACA GCC AGA CGT CGG CTT
 F   C   F   E   V   T   T   S   S   G   T   K   C   F   A   C   R   S   A   A   E 380          390          400          410          420          430          440
     *            *            *            *            *            *            *
AGG GAC AAA TGG ATT GAG AAT CTA CAG AGG GCT GTG AAA CCC AAC AAG GAC AAC AGC CGC CGG
TCC CTG TTT ACC TAA CTC TTA GAT GTC TCC CGA CAC TTT GGG TTG TTC CTG TTG TCG GCG GCC
 R   D   K   W   I   E   N   L   Q   R   A   V   K   P   N   K   D   N   S   R   R 450          460          470          480          490          500
          *            *            *            *            *            *
GTA GAT AAC GTG CTG AAA CTA TGG ATC ATA GAA GCT CGA GAG CTG CCC CCC AAG AAG CGA TAT
CAT CTA TTG CAC GAC TTT GAT ACC TAG TAT CTT CGA GCT CTC GAC GGG GGG TTC TTC GCT ATA
 V   D   N   V   L   K   L   W   I   I   E   A   R   E   L   P   P   K   K   R   Y 510          520          530          540          550          560
          *            *            *            *            *            *
TAC TGC GAG TTA TGC CTG GAC GAC ATG CTC TAT GCA CGG ACC ACT TCC AAG CCC CGC TCA GCC
ATG ACG CTC AAT ACG GAC CTG CTG TAC GAG ATA CGT GCC TGG TGA AGG TTC GGG GCG AGT CGG
 Y   C   E   L   C   L   D   D   M   L   Y   A   R   T   T   S   K   P   R   S   A 570          580          590          600          610          620          630
     *            *            *            *            *            *            *
TCA GGA GAC ACT GTC TTT TGG GGC GAG CAC TTC GAG TTT AAC AAC CTG CCT GCT GTC CGG GCG
AGT CCT CTG TGA CAG AAA ACC CCG CTC GTG AAG CTC AAA TTG TTG GAC GGA CGA CAG GCC CGC
 S   G   D   T   V   F   W   G   E   H   F   E   F   N   N   L   P   A   V   R   A
```

FIGURE 3A

```
       640         650         660         670         680         690
        *           *           *           *           *           *
CTG CGG CTG CAT CTG TAC CGT GAC TCG GAC AAA AAG CGG AAG AAG GAC AAG GCA GGC TAC GTT
GAC GCC GAC GTA GAC ATG GCA CTG AGC CTG TTT TTC GCC TTC TTC CTG TTC CGT CCG ATG CAA
 L   R   L   H   L   Y   R   D   S   D   K   K   R   K   K   D   K   A   G   Y   V 700         710         720         730         740         750
        *           *           *           *           *           *
GGC CTG GTG ACT GTT CCA GTG GCC ACC CTG GCT GGG CGC CAC TTC ACA GAG CAG TGG TAC CCC
CCG GAC CAC TGA CAA GGT CAC CGG TGG GAC CGA CCC GCG GTG AAG TGT CTC GTC ACC ATG GGG
 G   L   V   T   V   P   V   A   T   L   A   G   R   H   F   T   E   Q   W   Y   P 780         790         800         810         820         830
        *           *           *           *           *           *
GTG ACC CTG CCA ACA GGA AGT GGG GGC TCT GGG GGT ATG GGC TCG GGG GGA GGA GGG GGG TCA
CAC TGG GAC GGT TGT CCT TCA CCC CCG AGA CCC CCA TAC CCG AGC CCC CCT CCT CCC CCC AGT
 V   T   L   P   T   G   S   G   G   S   G   G   M   G   S   G   G   G   G   G   S 820         830         840         850         860         870         880
    *           *           *           *           *           *           *
GGG GGC GGC TCA GGG GGC AAA GGG AAA GGA GGC TGT CCT GCT GTG CGG CTG AAG GCC CGT TAC
CCC CCG CCG AGT CCC CCG TTT CCC TTT CCT CCG ACA GGA CGA CAC GCC GAC TTC CGG GCA ATG
 G   G   G   S   G   G   K   G   K   G   G   C   P   A   V   R   L   K   A   R   Y 890         900         910         920         930         940
        *           *           *           *           *           *
CAG ACA ATG AGT ATC CTG CCC ATG GAG CTA TAT AAG GAG TTT GCA GAA TAT GTG ACC AAC CAC
GTC TGT TAC TCA TAG GAC GGG TAC CTC GAT ATA TTC CTC AAA CGT CTT ATA CAC TGG TTG GTG
 Q   T   M   S   I   L   P   M   E   L   Y   K   E   F   A   E   Y   V   T   N   H 950         960         970         980         990        1000
        *           *           *           *           *           *
TAC CGC ATG CTG TGT GCC GTG CTG GAG CCC GCC CTC AAT GTC AAG GGC AAG GAG GAG GTC GCT
ATG GCG TAC GAC ACA CGG CAC GAC CTC GGG CGG GAG TTA CAG TTC CCG TTC CTC CTC CAG CGA
 Y   R   M   L   C   A   V   L   E   P   A   L   N   V   K   G   K   E   E   V   A 1010        1020        1030        1040        1050        1060        1070
    *           *           *           *           *           *           *
AGT GCA CTG GTT CAC ATC CTG CAA AGC ACA GGC AAG GCC AAG GAC TTC CTT TCA GAC ATG GCC
TCA CGT GAC CAA GTG TAG GAC GTT TCG TGT CCG TTC CGG TTC CTG AAG GAA AGT CTG TAC CGG
 S   A   L   V   H   I   L   Q   S   T   G   K   A   K   D   F   L   S   D   M   A 1080        1090        1100        1110        1120        1130
        *           *           *           *           *           *
ATG TCA GAG GTA GAC CGG TTC ATG GAG CGG GAA CAC CTC ATA TTC CGC GAG AAC ACG CTC GCC
TAC AGT CTC CAT CTG GCC AAG TAC CTC GCC CTT GTG GAG TAT AAG GCG CTC TTG TGC GAG CGG
 M   S   E   V   D   R   F   M   E   R   E   H   L   I   F   R   E   N   T   L   A 1140        1150        1160        1170        1180        1190
        *           *           *           *           *           *
ACT AAA GCC ATA GAA GAG TAT ATG AGA CTG ATT GGC CAG AAA TAC CTC AAG GAT GCC ATT GGG
TGA TTT CGG TAT CTT CTC ATA TAC TCT GAC TAA CCG GTC TTT ATG GAG TTC CTA CGG TAA CCC
 T   K   A   I   E   E   Y   M   R   L   I   G   Q   K   Y   L   K   D   A   I   G 1200        1210        1220        1230        1240        1250        1260
    *           *           *           *           *           *           *
GAG TTC ATC CGG GCT CTG TAT GAA TCT GAG GAG AAC TGT GAA GTA GAC CCC ATC AAG TGC ACA
CTC AAG TAG GCC CGA GAC ATA CTT AGA CTC CTC TTG ACA CTT CAT CTG GGG TAG TTC ACG TGT
 E   F   I   R   A   L   Y   E   S   E   E   N   C   E   V   D   P   I   K   C   T
```

FIGURE 3B

```
      1270        1280        1290        1300        1310        1320
       *           *           *           *           *           *
GCG TCC AGT CTG GCA GAG CAC CAG GCC AAC CTG CGG ATG TGC TGT GAG TTG GCC CTG TGC AAG
CGC AGG TCA GAC CGT CTC GTG GTC CGG TTG GAC GCC TAC ACG ACA CTC AAC CGG GAC ACG TTC
 A   S   S   L   A   E   H   Q   A   N   L   R   M   C   C   E   L   A   L   C   K 1330        1340        1350        1360        1370        1380
       *           *           *           *           *           *
GTG GTC AAC TCC CAT TGC GTG TTC CCG AGG GAG CTG AAG GAG GTG TTT GCA TCA TGG CGG CTG
CAC CAG TTG AGG GTA ACG CAC AAG GGC TCC CTC GAC TTC CTC CAC AAA CGT AGT ACC GCC GAC
 V   V   N   S   H   C   V   F   P   R   E   L   K   E   V   F   A   S   W   R   L 1390        1400        1410        1420        1430        1440
       *           *           *           *           *           *
CGC TGT GCA GAG CGG GGC CGG GAG GAC ATT GCT GAC AGG CTG ATC AGC GCC TCG CTC TTC CTG
GCG ACA CGT CTC GCC CCG GCC CTC CTG TAA CGA CTG TCC GAC TAG TCG CGG AGC GAG AAG GAC
 R   C   A   E   R   G   R   E   D   I   A   D   R   L   I   S   A   S   L   F   L 1450        1460        1470        1480        1490        1500        1510
   *           *           *           *           *           *           *
CGC TTC CTC TGC CCG GCC ATC ATG TCG CCC AGT CTG TTT GGA CTG ATG CAG GAG TAC CCA GAT
GCG AAG GAG ACG GGC CGG TAG TAC AGC GGG TCA GAC AAA CCT GAC TAC GTC CTC ATG GGT CTA
 R   F   L   C   P   A   I   M   S   P   S   L   F   G   L   M   Q   E   Y   P   D 1520        1530        1540        1550        1560        1570
       *           *           *           *           *           *
GAG CAG ACC TCA CGA ACC CTC ACC CTC ATC GCC AAG GTT ATC CAG AAC CTG GCC AAC TTT TCC
CTC GTC TGG AGT GCT TGG GAG TGG GAG TAG CGG TTC CAA TAG GTC TTG GAC CGG TTG AAA AGG
 E   Q   T   S   R   T   L   T   L   I   A   K   V   I   Q   N   L   A   N   F   S 1580        1590        1600        1610        1620        1630
       *           *           *           *           *           *
AAG TTT ACC TCA AAG GAG GAC TTC CTG GGC TTC ATG AAC GAG TTT CTG GAG CTG GAA TGG GGT
TTC AAA TGG AGT TTC CTC CTG AAG GAC CCG AAG TAC TTG CTC AAA GAC CTC GAC CTT ACC CCA
 K   F   T   S   K   E   D   F   L   G   F   M   N   E   F   L   E   L   E   W   G 1640        1650        1660        1670        1680        1690        1700
       *           *           *           *           *           *           *
TCT ATG CAG CAA TTC TTG TAT GAG ATA TCC AAC CTG GAC ACA CTG ACC AAC AGC AGC AGT TTT
AGA TAC GTC GTT AAG AAC ATA CTC TAT AGG TTG GAC CTG TGT GAC TGG TTG TCG TCG TCA AAA
 S   M   Q   Q   F   L   Y   E   I   S   N   L   D   T   L   T   N   S   S   S   F 1710        1720        1730        1740        1750        1760
       *           *           *           *           *           *
GAG GGC TAC ATA GAC TTG GGC CGC GAG CTC TCC ACA CTT CAC GCC CTG CTC TGG GAG GTG CTG
CTC CCG ATG TAT CTG AAC CCG GCG CTC GAG AGG TGT GAA GTG CGG GAC GAG ACC CTC CAC GAC
 E   G   Y   I   D   L   G   R   E   L   S   T   L   H   A   L   L   W   E   V   L 1770        1780        1790        1800        1810        1820
       *           *           *           *           *           *
CCC CAG CTC AGC AAG GAA GCC CTC CTG AAG CTG GGC CCG CTG CCC CGG CTC CTC AGC GAC ATC
GGG GTC GAG TCG TTC CTT CGG GAG GAC TTC GAC CCG GGC GAC GGG GCC GAG GAG TCG CTG TAG
 P   Q   L   S   K   E   A   L   L   K   L   G   P   L   P   R   L   L   S   D   I 1830        1840        1850        1860        1870        1880        1890
   *           *           *           *           *           *           *
AGC ACA GCC CTG AGG AAC CCT AAC ATC CAA AGG CAG CCG AGC CGC CAG AGC GAG CGC GCT CGG
TCG TGT CGG GAC TCC TTG GGA TTG TAG GTT TCC GTC GGC TCG GCG GTC TCG CTC GCG CGA GCC
 S   T   A   L   R   N   P   N   I   Q   R   Q   P   S   R   Q   S   E   R   A   R
```

FIGURE 3C

```
        1900            1910            1920            1930            1940            1950
          •               •               •               •               •               •
TCT CAG CCC ATG GTG CTG CGC GGG CCG TCA GCC GAA ATG CAG GGC TAC ATG ATG CGG GAC CTC
AGA GTC GGG TAC CAC GAC GCG CCC GGC AGT CGG CTT TAC GTC CCG ATG TAC TAC GCC CTG GAG
 S   Q   P   M   V   L   R   G   P   S   A   E   M   Q   G   Y   M   M   R   D   L 1960            1970            1980            1990            2000            2010
          •               •               •               •               •               •
AAC AGC TCC ATC GAC CTT CAG TCC TTC ATG GCT CGA GGC CTC AAC AGC TCT ATG GAC ATG GCT
TTG TCG AGG TAG CTG GAA GTC AGG AAG TAC CGA GCT CCG GAG TTG TCG AGA TAC CTG TAC CGA
 N   S   S   I   D   L   Q   S   F   M   A   R   G   L   N   S   S   M   D   M   A 2020            2030            2040            2050            2060            2070
          •               •               •               •               •               •
CGC CTC CCC TCC CCA ACC AAG GAG AAA CCC CCG CCG CCC CCT CCC GGT GGG GGT AAA GAC CTG
GCG GAG GGG AGG GGT TGG TTC CTC TTT GGG GGC GGC GGG GGA GGG CCA CCC CCA TTT CTG GAC
 R   L   P   S   P   T   K   E   K   P   P   P   P   P   P   G   G   G   K   D   L 2080            2090            2100            2110            2120            2130            2140
          •               •               •               •               •               •               •
TTC TAT GTG AGC CGG CCA CCA CTG GCC CGG TCC TCC CCA GCA TAC TGC ACG AGC AGC TCG GAC
AAG ATA CAC TCG GCC GGT GGT GAC CGG GCC AGG AGG GGT CGT ATG ACG TGC TCG TCG AGC CTG
 F   Y   V   S   R   P   P   L   A   R   S   S   P   A   Y   C   T   S   S   S   D 2150            2160            2170            2180            2190            2200
          •               •               •               •               •               •
ATC ACA GAG CCG GAG CAG AAG ATG CTG AGT GTC AAC AAG AGT GTG TCC ATG CTG GAC CTG CAG
TAG TGT CTC GGC CTC GTC TTC TAC GAC TCA CAG TTG TTC TCA CAC AGG TAC GAC CTG GAC GTC
 I   T   E   P   E   Q   K   M   L   S   V   N   K   S   V   S   M   L   D   L   Q 2210            2220            2230            2240            2250            2260
          •               •               •               •               •               •
GGC GAC GGG CCT GGG GGC CGC CTT AAC AGC AGT AGT GTT TCC AAC CTG GCA GCT GTT GGG GAC
CCG CTG CCC GGA CCC CCG GCG GAA TTG TCG TCA TCA CAA AGG TTG GAC CGT CGA CAA CCC CTG
 G   D   G   P   G   G   R   L   N   S   S   S   V   S   N   L   A   A   V   G   D 2270            2280            2290            2300            2310            2320            2330
          •               •               •               •               •               •               •
CTG TTG CAC TCA AGC CAG GCT TCA CTG ACA GCA GCC TTG GGG TTG CGG CCT GCA CCT GCC GGG
GAC AAC GTG AGT TCG GTC CGA AGT GAC TGT CGT CGG AAC CCC AAC GCC GGA CGT GGA CGG CCC
 L   L   H   S   S   Q   A   S   L   T   A   A   L   G   L   R   P   A   P   A   G 2340            2350            2360            2370            2380            2390
          •               •               •               •               •               •
CGC CTC TCC CAA GGG AGT GGC TCT TCC ATC ACA GCA GCC GGC ATG CGC CTC AGC CAG ATG GGT
GCG GAG AGG GTT CCC TCA CCG AGA AGG TAG TGT CGT CGG CCG TAC GCG GAG TCG GTC TAC CCA
 R   L   S   Q   G   S   G   S   S   I   T   A   A   G   M   R   L   S   Q   M   G 2400            2410            2420            2430            2440            2450
          •               •               •               •               •               •
GTC ACT ACG GAT GGT GTC CCC GCC CAG CAA CTG CGC ATC CCT CTT TCC TTC CAG AAC CCT CTC
CAG TGA TGC CTA CCA CAG GGG CGG GTC GTT GAC GCG TAG GGA GAA AGG AAG GTC TTG GGA GAG
 V   T   T   D   G   V   P   A   Q   Q   L   R   I   P   L   S   F   Q   N   P   L 2460            2470            2480            2490            2500            2510            2520
          •               •               •               •               •               •               •
TTC CAT ATG GCT GCC GAT GGA CCA GGG CCC CCA GCA GGC CAT GGA GGG AGC AGT GGC CAT GGT
AAG GTA TAC CGA CGG CTA CCT GGT CCC GGG GGT CGT CCG GTA CCT CCC TCG TCA CCG GTA CCA
 F   H   M   A   A   D   G   P   G   P   P   A   G   H   G   G   S   S   G   H   G
```

FIGURE 3D

```
       2530           2540           2550           12560          2570           2580
        •              •              •              •              •              •
CCA CCT TCC TCC CAT CAC CAC CAC CAC CAC CAT CAC CAT CAC CGA GGG GGA GAA CCC CCA GGG
GGT GGA AGG AGG GTA GTG GTG GTG GTG GTG GTA GTG GTA GTG GCT CCC CCT CTT GGG GGT CCC
 P   P   S   S   H   H   H   H   H   H   H   H   H   H   R   G   G   E   P   P   G 2590           2600           2610           2620           2630           2640
        •              •              •              •              •              •
GAC ACT TTT GCC CCG TTC CAT GGC TAT AGC AAG AGC GAG GAC CTC TCT ACA GGG GTC CCT AAG
CTG TGA AAA CGG GGC AAG GTA CCG ATA TCG TTC TCG CTC CTG GAG AGA TGT CCC CAG GGA TTC
 D   T   F   A   P   F   H   G   Y   S   K   S   E   D   L   S   T   G   V   P   K 2650           2660           2670           2680           2690           2700
        •              •              •              •              •              •
CCC CCT GCG GCC TCC ATC CTT CAC AGC CAC AGC TAC AGT GAT GAG TTT GGA CCC TCT GGT ACT
GGG GGA CGC CGG AGG TAG GAA GTG TCG GTG TCG ATG TCA CTA CTC AAA CCT GGG AGA CCA TGA
 P   P   A   A   S   I   L   H   S   H   S   Y   S   D   E   F   G   P   S   G   T 2710       2720       2730       2740       2750       2760       2770
     •          •          ▼          •          •          •          *
GAT TTT ACC CGT CGG CAG CTC TCA CTT CAG GAC AAC CTA CAG CAC ATG CTC TCC CCG CCC CAG
CTA AAA TGG GCA GCC GTC GAG AGT GAA GTC CTG TTG GAT GTC GTG TAC GAG AGG GGC GGG GTC
 D   F   T   R   R   Q   L   S   L   Q   D   N   L   Q   H   M   L   S   P   P   Q 2780           2790           2800           2810           2820           2830
           •              •              •              •              •              •
ATC ACC ATC GGT CCC CAG AGG CCA GCT CCC TCA GGG CCA GGA GGG GGC AGT GGT GGG GGC AGT
TAG TGG TAG CCA GGG GTC TCC GGT CGA GGG AGT CCC GGT CCT CCC CCG TCA CCA CCC CCG TCA
 I   T   I   G   P   Q   R   P   A   P   S   G   P   G   G   S   G   G   G   S 2840           2850           2860           2870           2880           2890
        •              •              •              •              •              •
GGT GGG GGC GGT GGG GGC CAG CCA CCT CCC TTG CAG AGG GGC AAA TCT CAG CAG TTG ACA GTG
CCA CCC CCG CCA CCC CCG GTC GGT GGA GGG AAC GTC TCC CCG TTT AGA GTC GTC AAC TGT CAC
 G   G   G   G   G   G   Q   P   P   P   L   Q   R   G   K   S   Q   Q   L   T   V 2900           2910           2920           2930           2940           2950           2960
        •              •              •              •              •              •              •
AGT GCT GCC CAG AAA CCC CGG CCG TCC AGC GGG AAC CTA TTG CAG TCC CCG GAA CCA AGT TAT
TCA CGA CGG GTC TTT GGG GCC GGC AGG TCG CCC TTG GAT AAC GTC AGG GGC CTT GGT TCA ATA
 S   A   A   Q   K   P   R   P   S   S   G   N   L   L   Q   S   P   E   P   S   Y 2970           2980           2990           3000           3010           3020
           •              •              •              •              •              •
GGT CCT GCC CGT CCA CGG CAA CAG AGC CTC AGC AAA GAG GGC AGC ATT GGG GGC AGC GGG GGC
CCA GGA CGG GCA GGT GCC GTT GTC TCG GAG TCG TTT CTC CCG TCG TAA CCC CCG TCG CCC CCG
 G   P   A   R   P   R   Q   Q   S   L   S   K   E   G   S   I   G   G   S   G   G 3030           3040           3050           3060           3070           3080
        •              •              •              •              •              •
AGC GGT GGC GGA GGG GGT GGG GGG CTC AAG CCC TCC ATC ACC AAG CAG CAT TCC CAG ACT CCA
TCG CCA CCG CCT CCC CCA CCC CCC GAG TTC GGG AGG TAG TGG TTC GTC GTA AGG GTC TGA GGT
 S   G   G   G   G   G   G   G   L   K   P   S   I   T   K   Q   H   S   Q   T   P 3090       3100       3110       3120       3130       3140       3150
     •          •          •          •          •          •          •
TCC ACG CTG AAC CCC ACG ATG CCG GCC TCG GAG CGG ACT GTA GCC TGG GTG TCC AAT ATG CCT
AGG TGC GAC TTG GGG TGC TAC GGC CGG AGC CTC GCC TGA CAT CGG ACC CAC AGG TTA TAC GGA
 S   T   L   N   P   T   M   P   A   S   E   R   T   V   A   W   V   S   N   M   P
```

FIGURE 3E

```
      3160            3170            3180            3190            3200            3210
        •               •               •               •               •               •
CAC CTG TCC GCT GAC ATC GAG AGT GCA CAC ATT GAG CGG GAA GAG TAC AAG CTG AAG GAG TAC
GTG GAC AGG CGA CTG TAG CTC TCA CGT GTG TAA CTC GCC CTT CTC ATG TTC GAC TTC CTC ATG
 H   L   S   A   D   I   E   S   A   H   I   E   R   E   E   Y   K   L   K   E   Y 3220            3230            3240            3250            3260            3270
        •               •               •               •               •               •
TCG AAG TCC ATG GAC GAG AGC CGA CTG GAC AGG GTG AAG GAG TAC GAG GAG GAG ATC CAC TCA
AGC TTC AGG TAC CTG CTC TCG GCT GAC CTG TCC CAC TTC CTC ATG CTC CTC CTC TAG GTG AGT
 S   K   S   M   D   E   S   R   L   D   R   V   K   E   Y   E   E   E   I   H   S 3280            3290            3300            3310            3320            3330
        •               •               •               •               •               •
CTG AAG GAA AGG CTA CAC ATG TCC AAC CGG AAG CTG GAA GAG TAC GAG CGG AGG CTG CTG TCC
GAC TTC CTT TCC GAT GTG TAC AGG TTG GCC TTC GAC CTT CTC ATG CTC GCC TCC GAC GAC AGG
 L   K   E   R   L   H   M   S   N   R   K   L   E   E   Y   E   R   R   L   L   S 3340           3350            3360            3370            3380            3390           3400
   •              •               •               •               •               •              •
CAG GAA GAG CAG ACC AGC AAG ATC CTG ATG CAG TAC CAA GCC CGC CTG GAG CAG AGC GAG AAG
GTC CTT CTC GTC TGG TCG TTC TAG GAC TAC GTC ATG GTT CGG GCG GAC CTC GTC TCG CTC TTC
 Q   E   E   Q   T   S   K   I   L   M   Q   Y   Q   A   R   L   E   Q   S   E   K 3410            3420            3430            3440            3450            3460
        •               •               •               •               •               •
CGC TTG AGG CAG CAG CAG GTG GAG AAG GAC TCC CAG ATC AAG AGC ATC ATT GGC AGG CTG ATG
GCG AAC TCC GTC GTC GTC CAC CTC TTC CTG AGG GTC TAG TTC TCG TAG TAA CCG TCC GAC TAC
 R   L   R   Q   Q   Q   V   E   K   D   S   Q   I   K   S   I   I   G   R   L   M 3470            3480            3490            3500            3510            3520
        •               •               •               •               •               •
CTG GTG GAG GAG GAG CTG CGC CGG GAC CAC CCC GCC ATG GCT GAG CCG CTG CCT GAA CCC AAG
GAC CAC CTC CTC CTC GAC GCG GCC CTG GTG GGG CGG TAC CGA CTC GGC GAC GGA CTT GGG TTC
 L   V   E   E   E   L   R   R   D   H   P   A   M   A   E   P   L   P   E   P   K 3530           3540            3550            3560            3570            3580           3590
   •              •               •               •               •               •              •
AAG AGG CTG CTC GAC GCT CAG AGA GGC AGC TTC CCC CCT TGG GTC CAA CAA ACC CGC GTG TGA
TTC TCC GAC GAG CTG CGA GTC TCT CCG TCG AAG GGG GGA ACC CAG GTT GTT TGG GCG CAC ACT
 K   R   L   L   D   A   Q   R   G   S   F   P   P   W   V   Q   Q   T   R   V   *

3600            3610            3620            3630            3640            3650
              •               •               •               •               •               •
      CGC TGG CCC CAC CTT GGA ACG GCC TGG CCC CCC CAG CCC CAC CCC CCC CAC CCC GGC TGC AGA
      GCG ACC GGG GTG GAA CCT TGC CGG ACC GGG GGG GTC GGG GTG GGG GGG GTG GGG CCG ACG TCT
       R   W   P   H   L   G   T   A   W   P   P   Q   P   H   P   P   H   P   G   C   R 3660            3670            3680            3690            3700            3710
              •               •               •               •               •               •
      TCA CAG AGA ACG GCG AGT TCC GGA ACA CCG CAG ACC ACT AGC CCA CCC AGC ATC ACA GAC CTC
      AGT GTC TCT TGC CGC TCA AGG CCT TGT GGC GTC TGG TGA TCG GGT GGG TCG TAG TGT CTG GAG
       S   Q   R   T   A   S   S   G   T   P   Q   T   T   S   P   P   S   I   T   D   L 3720           3730            3740            3750            3760            3770           3780
   •              •               •               •               •               •              •
CTT CCC TGT GCA CCC TAC CCC GGC CCA CCC AGC GTC ACA GAC CTC CTT CCC AGT GCA CCC GAC
GAA GGG ACA CGT GGG ATG GGG CCG GGT GGG TCG CAG TGT CTG GAG GAA GGG TCA CGT GGG CTG
 L   P   C   A   P   Y   P   G   P   P   S   V   T   D   L   L   P   S   A   P   D
```

FIGURE 3F

```
         3790           3800            3810             3820            3830             3840
          *              *               *                *               *                *
CCT GGA ACA TCA CCA ACC ACC AGG ACT GGA CGT CAC CAA GGG ACA GCG GGA TTG TCT CCC TTA
GGA CCT TGT AGT GGT TGG TGG TCC TGA CCT GCA GTG GTT CCC TGT CGC CCT AAC AGA GGG AAT
 P   G   T   S   P   T   T   R   T   G   R   H   Q   G   T   A   G   L   S   P   L 3850           3860            3870             3880            3890             3900
          *              *               *                *               *                *
ACG CCT CCT TGG GGC ACC CAT CTG TCA ACC CCA CTG CTC CAT TCC AGG AGG GAG AGT GGG ACC
TGC GGA GGA ACC CCG TGG GTA GAC AGT TGG GGT GAC GAG GTA AGG TCC TCC CTC TCA CCC TGG
 T   P   P   W   G   T   H   L   S   T   P   L   L   H   S   R   R   E   S   G   T 3910           3920            3930             3940            3950             3960
          *              *               *                *               *                *
CTC AGC TGC CCT CTC ACC CCA GGA CAC CAC CTA CCC CAC ACA GAC CCC TTC ACT CTG GGG TGC
GAG TCG ACG GGA GAG TGG GGT CCT GTG GTG GAT GGG GTG TGT CTG GGG AAG TGA GAC CCC ACG
 L   S   C   P   L   T   P   G   H   H   L   P   H   T   D   P   F   T   L   G   C 3970           3980
 *              *
TAT CCC CAT CCT
ATA GGG GTA GGA
 Y   P   H   P
```

FIGURE 3F

| | | |
|---|---|---|
| 1 | MQSFKESHSHESLLSPSSAAEALELNLDEDSIIKPVHSSILGQEFCFEVTTSSGTKCFAC | 60 |
| 61 | RSAAERDKWIENLQRAVKPNKDNSRRVDNVLKLWIIEARELPPKKRYYCELCLDDMLYAR | 120 |
| 121 | TTSKPRSASGDTVPWGEHFBFNNLPAVRALRLHLYRDSDKKRKKDKAGYVGLVTVPVATL | 180 |
| 181 | AGRHFTEQWYPVTLPTGSGGSGGMGSGGGGGSGGGSGGKGKGGCPAVRLKARYQTMSILP | 240 |
| 241 | MELYKEFAEYVTNHYRMLCAVLEPALNVKGKEEVASALVHILQSTGKAKDFLSDMAMSEV | 300 |
| 301 | DRFMEREHLIFRENTLATKAIEEYMRLIGQKYLKDAIGEFIRALYESEENCEVDPIKCTA | 360 |
| 361 | SSLAEHQANLRMCCELALCKVVNSHCVFPRELKEVFASWRLRCAERGREDIADRLISASL | 420 |
| 421 | FLRFLCPAIMSPSLFGLMQEYPDEQTSRTLTLIAKVIQNLANFSKFTSKEDFLGFMNEFL | 480 |
| 481 | ELEWGSMQQFLYEISNLDTLTNSSSFEGYIDLGRELSTLHALLWEVLPQLSKEALLKLGP | 540 |
| 541 | LPRLLSDISTALRNPNIQRQPSRQSERARSQPMVLRGPSAEMQGYMMRDLNSSIDLQSFM | 600 |
| 601 | ARGLNSSMDMARLPSPTKEKPPPPPPGGGKDLFYVSRPPLARSSPAYCTSSSDITEPEQK | 660 |
| 661 | MLSVNKSVSMLDLQGDGPGGRLNSSSVSNLAAVGDLLHSSQASLTAALGLRPAPAGRLSQ | 720 |
| 721 | GSGSSITAAGMRLSQMGVTTDGVPAQQLRIPLSFQNPLFHMAADGPGPPAGHGGSSGHGP | 780 |
| 781 | PSSHHHHHHHHHHRGGEPPGDTFAPFHGYSKSEDLSTGVPKPPAASILHSHSYSDEFGPS | 840 |
| 841 | GTDFTRRQLSLQDNLQHMLSPPQITIGPQRPAPSGPGGGSGGGSGGGGGQPPPLQRGKS | 900 |
| 901 | QQLTVSAAQKPRPSSGNLLQSPEPSYGPARPRQQSLSKEGSIGGSGGSGGGGGGLKPSI | 960 |
| 961 | TKQHSQTPSTLNPTMPASERTVAWVSNMPHLSADIESAHIEREEYKLKEYSKSMDESRLD | 1020 |
| 1021 | RVKEYEEEIHSLKERLHMSNRKLEEYERRLLSQEEQTSKILMQYQARLEQSEKRLRQQQV | 1080 |
| 1081 | EKDSQIKSIIGRLMLVEEELRRDHPAMAEPLPEPKKRLLDAQRGSFPPWVQQTRV | 1135 |

FIGURE 4A

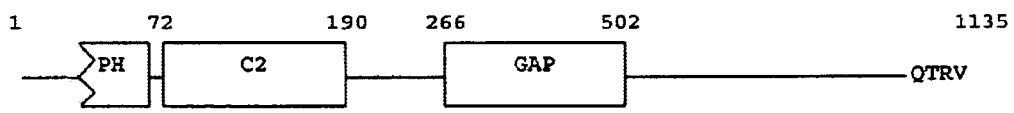

FIGURE 4B

```
                           +   + +
GAPSYN  286  GKAKDFLSDMAMSEVDRFMEREHLIFRENTLATKAIEEYMRLIGQKYLKDAIGEFIRALYE   347
rn GAP   755  KLESLLLCTLNDREIS-MEDEATTLFRATTLASTLMEQYMKATATQFVHHALKDSILKIME   815
hs NF1  1251  HLLYQLLWNMFSKEVE-LADSMQTLFRGNSLASKIMTFCFKVYGATYLQKLL-DPLLRIVI   1311

GAPSYN  348  SEE-----NCEVDPIKCTAS-SLAEHQANLRMCCELALCKVVNSHCVFPRELKEVFASWRLR   403
rn GAP   816  SKQ-----SCELSPSKLEKNEDVNTNLAHLLSILSELVEKIFMASEILPPTLRYIYGCLQKS   872
hs NF1  1312  TSSDWQHVSFEVDPTRLEPSESLEENQRNLLQMTEKFFHAIISSSSEFPPQLRSVCHCLYQV   1372

++      +                                       +
GAPSYN  404  CAER--GREDIADRLISASLFLRFLCPAIMSPSLFGLMQEYPDEQTSRTLTLIAKVIQNLAN   463
rn GAP   873  VQHKWPTNNTMRTRVVSGFVFLRLICPAILNPRMFNIISDSPSPIAARTLTLVAKSVQNLAN   934
hs NF1  1373  VSQRFPQNSIG---AVGSAMFLRFINPAIVSPYEAGILDKKPPPRIERGLKLMSKILQSIAN   1430

++
GAPSYN  464  FSKFTSKEDFLGFMNEFLELE-WGSMQQFLYEISNLDTLT                         502
rn GAP   935  LVEFGAKEPYMEGVNPFIKSN-KHRMIMFLDELGNVPELP                         973
hs NF1  1431  HVLF-TKEEHMRPFNDFVKSNFDAARRFFLDIASDCPTSD                         1469
```

FIGURE 4C

PLECKSTRIN HOMOLOGY (PH) DOMAIN ALIGNMENT

```
SynGAP-a  162   FKESHSHESL  LP SSAA...  .....EALEL  NLD........  ...EDSIKK   192
Hs  p120  471   FYKNIVKKGY  LLKKGKG...  ..KRWKNLYF  ILEGSDAQLI   YFESEKRATK  515
Dm  GAP1  759   PVLLKEGEGL  MTKYPTSRKR  FGRQFKQRHF  RLTT..HSLS   YAKSK..GKQ  804
Hs  Plec    1   MEPKRIREGY  LVKKGSV....  FNTWKPMWV  VLLE..DGIE   FYKKK.SDN    44

SynGAP-a  193   P..........  ....VHSSIL  GQ.EFCFEVT  TSSGTKC...   ..FACRSAAE  223
Hs  p120  516   PKGLIDLSVC  SVYVVHDSLF  GR.PNCFQIV  VQHFSEEHYI   FYFAGETPEQ  564
Dm  GAP1  805   PICDIPLQEI  ASVEQLKDKS  FKMQNCFKIV  HNDRS.....   LIVQTTNCVE  849
Hs  Plec   45   PKGMIPLKGS  TLTSPCQDFG  KR.MFVFKIT  TTKQQ....D   HFFQAAFLEE   88

SynGAP-a  224   RDKWIENLQR  AVKPNKDNSR  243
Hs  p120  565   AEDWMKGLQA  FCNLRKSSPG  584
Dm  GAP1  850   EREWFDLLHK  ICLMNSIRMQ  869
Hs  Plec   89   RDAWVRDINK  AIKCIEGGQK  108
```

FIGURE 5

C2 DOMAIN ALIGNMENT

```
SynGAP-a   245  ..VDNVLKLW  ..IIEARELP  ....PKKRY.  YCELCL....  DDMLYARTTS  281
Hs  p120   592  ..QVSSLVLH  ..IEEAHKLP  ...VKHFTNP  YCNIYL....  NSVQVAKTH.  629
Rn  Syt II 151  DYDFQANQLT  VGVLQAAELP  ALDMGGTSDP  YVKVFLLPD.  .KKKKYETKV  198
Bt  Rab 3A 411  LYDQDNSSLK  CTIIKAKGLK  PMDSNGLADP  YVKLHLLPGA  SKSNKLRTKT  460

SynGAP-a   282  KPRSASGDTV  FWGEHFEFNN  LP.AVRALRL  HLYRD.SDKK  RKKDKAGYVG  329
Hs  p120   630  ...AREGQNP  VWSEEFVFDD  LPPDINRFEI  TL....SNKT  .KKSKDPDIL  671
Rn  Syt II 199  ...HRKTLNP  AFNETFTFKV  ..PYQELGGK  TLVMAIYDFD  RF.SKHDIIG  242
Bt  Rab 3A 462  ...LRNTRNP  IWNETLVYHG  I.TDEDMQRK  TLRISVCDED  KF.GHNEFIG  505

SynGAP-a   330  LVTVPVAT..  ..........  .LAGRHFTEQ  WY.PVT.LPT  354
Hs  p120   672  FMRCQLSR..  ..........  .LQKGHATDE  WFLLSSHIPL  698
Rn  Syt II 243  EVKVPMNTVD  ..........  .L..GQPIEE  WRDLQG..G.  266
Bt  Rab 3A 506  ETRFSLKKLK  PNQRK.NFNI  CL..ERVIPM  KRAGTTGSAR  542
```

FIGURE 6

GAPSYN

GAPSYN

SYNAPTOPHYSIN

OVERLAP

GAPSYN (BLOCK)

SYNAPTOPHYSIN

SEQUENCE LISTING

```
<160> NUMBER OF SEQ ID NOS: 24

<210> SEQ ID NO 1
<211> LENGTH: 4272
<212> TYPE: DNA
<213> ORGANISM: Unknown Organism
<220> FEATURE:
<223> OTHER INFORMATION: Description of Unknown Organism: mammalian
      SYNGAP-A
<220> FEATURE:
<221> NAME/KEY: CDS
<222> LOCATION: (1)..(3879)
<220> FEATURE:
<221> NAME/KEY: CDS
<222> LOCATION: (3883)..(4272)

<400> SEQUENCE: 1 atg tcc tat gcc ccc ttc aga gat gta cgg gga ccc cct atg cac cga        48
Met Ser Tyr Ala Pro Phe Arg Asp Val Arg Gly Pro Pro Met His Arg
 1               5                  10                  15 acc caa tac gtt cat tcc ccg tat gac cgt ccc ggt tgg aac ccc cgg        96
Thr Gln Tyr Val His Ser Pro Tyr Asp Arg Pro Gly Trp Asn Pro Arg
                20                  25                  30 ttc tgc atc atc tct ggg aac cag ctg ctc atg ctg gat gag gat gag       144
Phe Cys Ile Ile Ser Gly Asn Gln Leu Leu Met Leu Asp Glu Asp Glu
            35                  40                  45 ata cac ccc ctt ctg atc cgc gac cgg agg agc gag tcc agc cga aac       192
Ile His Pro Leu Leu Ile Arg Asp Arg Arg Ser Glu Ser Ser Arg Asn
        50                  55                  60 aaa ctg ctg aga cgc acc gtc tct gtg cca gtg gag ggg cgg ccc cac       240
Lys Leu Leu Arg Arg Thr Val Ser Val Pro Val Glu Gly Arg Pro His
 65                  70                  75                  80 ggc gag cat gaa tac cac ttg ggt cgc tcg agg agg aag agt gtc ccc       288
Gly Glu His Glu Tyr His Leu Gly Arg Ser Arg Arg Lys Ser Val Pro
                85                  90                  95 ggg ggg aaa cag tac agc atg gaa gcc gcc ccc gct gcg ccc ttc cgg       336
Gly Gly Lys Gln Tyr Ser Met Glu Ala Ala Pro Ala Ala Pro Phe Arg
            100                 105                 110 ccc tcg caa ggc ttc ctg agc cgg agg cta aaa agc tcc atc aaa cgt       384
Pro Ser Gln Gly Phe Leu Ser Arg Arg Leu Lys Ser Ser Ile Lys Arg
        115                 120                 125 aca aag tca caa ccc aaa ctt gac cgg acc agc agc ttt cga cag atc       432
Thr Lys Ser Gln Pro Lys Leu Asp Arg Thr Ser Ser Phe Arg Gln Ile
    130                 135                 140 ctg cct cgc ttc cga agt gct gac cat gac cgg gcc cgg ctg atg cag       480
Leu Pro Arg Phe Arg Ser Ala Asp His Asp Arg Ala Arg Leu Met Gln
145                 150                 155                 160 agc ttc aag gag tct cac tcc cat gag tcc ctg ctg agt ccc agc agt       528
```

```
Ser Phe Lys Glu Ser His Ser His Glu Ser Leu Leu Ser Pro Ser Ser
            165                 170                 175 gct gct gag gcc ctg gag ctc aac ctg gat gaa gac tcc att atc aag          576
Ala Ala Glu Ala Leu Glu Leu Asn Leu Asp Glu Asp Ser Ile Ile Lys
        180                 185                 190 cca gta cac agc tcc atc ctg ggc cag gag ttc tgc ttt gag gta aca          624
Pro Val His Ser Ser Ile Leu Gly Gln Glu Phe Cys Phe Glu Val Thr
            195                 200                 205 aca tcg tct ggg aca aaa tgt ttt gcc tgt cgg tct gca gcc gaa agg          672
Thr Ser Ser Gly Thr Lys Cys Phe Ala Cys Arg Ser Ala Ala Glu Arg
    210                 215                 220 gac aaa tgg att gag aat cta cag agg gct gtg aaa ccc aac aag gac          720
Asp Lys Trp Ile Glu Asn Leu Gln Arg Ala Val Lys Pro Asn Lys Asp
225                 230                 235                 240 aac agc cgc cgg gta gat aac gtg ctg aaa cta tgg atc ata gaa gct          768
Asn Ser Arg Arg Val Asp Asn Val Leu Lys Leu Trp Ile Ile Glu Ala
                245                 250                 255 cga gag ctg ccc ccc aag aag cga tat tac tgc gag tta tgc ctg gac          816
Arg Glu Leu Pro Pro Lys Lys Arg Tyr Tyr Cys Glu Leu Cys Leu Asp
            260                 265                 270 gac atg ctc tat gca cgg acc act tcc aag ccc cgc tca gcc tca gga          864
Asp Met Leu Tyr Ala Arg Thr Thr Ser Lys Pro Arg Ser Ala Ser Gly
        275                 280                 285 gac act gtc ttt tgg ggc gag cac ttc gag ttt aac aac ctg cct gct          912
Asp Thr Val Phe Trp Gly Glu His Phe Glu Phe Asn Asn Leu Pro Ala
    290                 295                 300 gtc cgg gcg ctg cgg ctg cat ctg tac cgt gac tcg gac aaa aag cgg          960
Val Arg Ala Leu Arg Leu His Leu Tyr Arg Asp Ser Asp Lys Lys Arg
305                 310                 315                 320 aag aag gac aag gca ggc tac gtt ggc ctg gtg act gtt cca gtg gcc         1008
Lys Lys Asp Lys Ala Gly Tyr Val Gly Leu Val Thr Val Pro Val Ala
                325                 330                 335 acc ctg gct ggg cgc cac ttc aca gag cag tgg tac ccc gtg acc ctg         1056
Thr Leu Ala Gly Arg His Phe Thr Glu Gln Trp Tyr Pro Val Thr Leu
            340                 345                 350 cca aca gga agt ggg ggc tct ggg ggt atg ggc tcg ggg gga gga ggg         1104
Pro Thr Gly Ser Gly Gly Ser Gly Gly Met Gly Ser Gly Gly Gly Gly
        355                 360                 365 ggg tca ggg ggc ggc tca ggg ggc aaa ggg aaa gga ggc tgt cct gct         1152
Gly Ser Gly Gly Gly Ser Gly Gly Lys Gly Lys Gly Gly Cys Pro Ala
    370                 375                 380 gtg cgg ctg aag gcc cgt tac cag aca atg agt atc ctg ccc atg gag         1200
Val Arg Leu Lys Ala Arg Tyr Gln Thr Met Ser Ile Leu Pro Met Glu
385                 390                 395                 400 cta tat aag gag ttt gca gaa tat gtg acc aac cac tac cgc atg ctg         1248
Leu Tyr Lys Glu Phe Ala Glu Tyr Val Thr Asn His Tyr Arg Met Leu
                405                 410                 415 tgt gcc gtg ctg gag ccc gcc ctc aat gtc aag ggc aag gag gag gtc         1296
Cys Ala Val Leu Glu Pro Ala Leu Asn Val Lys Gly Lys Glu Glu Val
            420                 425                 430 gct agt gca ctg gtt cac atc ctg caa agc aca ggc aag gcc aag gac         1344
Ala Ser Ala Leu Val His Ile Leu Gln Ser Thr Gly Lys Ala Lys Asp
        435                 440                 445 ttc ctt tca gac atg gcc atg tca gag gta gac cgg ttc atg gag cgg         1392
Phe Leu Ser Asp Met Ala Met Ser Glu Val Asp Arg Phe Met Glu Arg
    450                 455                 460 gaa cac ctc ata ttc cgc gag aac acg ctc gcc act aaa gcc ata gaa         1440
Glu His Leu Ile Phe Arg Glu Asn Thr Leu Ala Thr Lys Ala Ile Glu
465                 470                 475                 480
```

-continued

| | | |
|---|---|---|
| gag tat atg aga ctg att ggc cag aaa tac ctc aag gat gcc att ggg<br>Glu Tyr Met Arg Leu Ile Gly Gln Lys Tyr Leu Lys Asp Ala Ile Gly<br>485                      490                        495 | 1488 |
| gag ttc atc cgg gct ctg tat gaa tct gag gag aac tgt gaa gta gac<br>Glu Phe Ile Arg Ala Leu Tyr Glu Ser Glu Glu Asn Cys Glu Val Asp<br>500                      505                      510 | 1536 |
| ccc atc aag tgc aca gcg tcc agt ctg gca gag cac cag gcc aac ctg<br>Pro Ile Lys Cys Thr Ala Ser Ser Leu Ala Glu His Gln Ala Asn Leu<br>515                      520                      525 | 1584 |
| cgg atg tgc tgt gag ttg gcc ctg tgc aag gtg gtc aac tcc cat tgc<br>Arg Met Cys Cys Glu Leu Ala Leu Cys Lys Val Val Asn Ser His Cys<br>530                      535                      540 | 1632 |
| gtg ttc ccg agg gag ctg aag gag gtg ttt gca tca tgg cgg ctg cgc<br>Val Phe Pro Arg Glu Leu Lys Glu Val Phe Ala Ser Trp Arg Leu Arg<br>545                      550                      555                      560 | 1680 |
| tgt gca gag cgg ggc cgg gag gac att gct gac agg ctg atc agc gcc<br>Cys Ala Glu Arg Gly Arg Glu Asp Ile Ala Asp Arg Leu Ile Ser Ala<br>565                      570                      575 | 1728 |
| tcg ctc ttc ctg cgc ttc ctc tgc ccg gcc atc atg tcg ccc agt ctg<br>Ser Leu Phe Leu Arg Phe Leu Cys Pro Ala Ile Met Ser Pro Ser Leu<br>580                      585                      590 | 1776 |
| ttt gga ctg atg cag gag tac cca gat gag cag acc tca cga acc ctc<br>Phe Gly Leu Met Gln Glu Tyr Pro Asp Glu Gln Thr Ser Arg Thr Leu<br>595                      600                      605 | 1824 |
| acc ctc atc gcc aag gtt atc cag aac ctg gcc aac ttt tcc aag ttt<br>Thr Leu Ile Ala Lys Val Ile Gln Asn Leu Ala Asn Phe Ser Lys Phe<br>610                      615                      620 | 1872 |
| acc tca aag gag gac ttc ctg ggc ttc atg aac gag ttt ctg gag ctg<br>Thr Ser Lys Glu Asp Phe Leu Gly Phe Met Asn Glu Phe Leu Glu Leu<br>625                      630                      635                      640 | 1920 |
| gag tgg ggt tct atg cag caa ttc ttg tat gag ata tcc aac ctg gac<br>Glu Trp Gly Ser Met Gln Gln Phe Leu Tyr Glu Ile Ser Asn Leu Asp<br>645                      650                      655 | 1968 |
| aca ctg acc aac agc agc agt ttt gag ggc tac ata gac ttg ggc cgc<br>Thr Leu Thr Asn Ser Ser Ser Phe Glu Gly Tyr Ile Asp Leu Gly Arg<br>660                      665                      670 | 2016 |
| gag ctc tcc aca ctt cac gcc ctg ctc tgg gag gtg ctg ccc cag ctc<br>Glu Leu Ser Thr Leu His Ala Leu Leu Trp Glu Val Leu Pro Gln Leu<br>675                      680                      685 | 2064 |
| agc aag gaa gcc ctc ctg aag ctg ggc ccg ctg ccc cgg ctc ctc agc<br>Ser Lys Glu Ala Leu Leu Lys Leu Gly Pro Leu Pro Arg Leu Leu Ser<br>690                      695                      700 | 2112 |
| gac atc agc aca gcc ctg agg aac cct aac atc caa agg cag ccg agc<br>Asp Ile Ser Thr Ala Leu Arg Asn Pro Asn Ile Gln Arg Gln Pro Ser<br>705                      710                      715                      720 | 2160 |
| cgc cag agc gag cgc gct cgg tct cag ccc atg gtg ctg cgc ggg ccg<br>Arg Gln Ser Glu Arg Ala Arg Ser Gln Pro Met Val Leu Arg Gly Pro<br>725                      730                      735 | 2208 |
| tca gcc gag atg cag ggc tac atg atg cgg gac ctc aac agc tcc atc<br>Ser Ala Glu Met Gln Gly Tyr Met Met Arg Asp Leu Asn Ser Ser Ile<br>740                      745                      750 | 2256 |
| gac ctt cag tcc ttc atg gct cga ggc ctc aac agc tct atg gac atg<br>Asp Leu Gln Ser Phe Met Ala Arg Gly Leu Asn Ser Ser Met Asp Met<br>755                      760                      765 | 2304 |
| gct cgc ctc ccc tcc cca acc aag gag aaa ccc ccg ccg ccc cct ccc<br>Ala Arg Leu Pro Ser Pro Thr Lys Glu Lys Pro Pro Pro Pro Pro Pro<br>770                      775                      780 | 2352 |
| ggt ggg ggt aaa gac ctg ttc tat gtg agc cgg cca cca ctg gcc cgg<br>Gly Gly Gly Lys Asp Leu Phe Tyr Val Ser Arg Pro Pro Leu Ala Arg<br>785                      790                      795                      800 | 2400 |

-continued

| | |
|---|---|
| tcc tcc cca gca tac tgc acg agc agc tcg gac atc aca gag ccg gag<br>Ser Ser Pro Ala Tyr Cys Thr Ser Ser Ser Asp Ile Thr Glu Pro Glu<br>805                               810                         815 | 2448 |
| cag aag atg ctg agt gtc aac aag agt gtg tcc atg ctg gac ctg cag<br>Gln Lys Met Leu Ser Val Asn Lys Ser Val Ser Met Leu Asp Leu Gln<br>      820                         825                       830 | 2496 |
| ggc gac ggg cct ggg ggc cgc ctt aac agc agt agt gtt tcc aac ctg<br>Gly Asp Gly Pro Gly Gly Arg Leu Asn Ser Ser Ser Val Ser Asn Leu<br>          835                       840                     845 | 2544 |
| gca gct gtt ggg gac ctg ttg cac tca agc cag gct tca ctg aca gca<br>Ala Ala Val Gly Asp Leu Leu His Ser Ser Gln Ala Ser Leu Thr Ala<br>850                               855                       860 | 2592 |
| gcc ttg ggg ttg cgg cct gca cct gcc ggg cgc ctc tcc caa ggg agt<br>Ala Leu Gly Leu Arg Pro Ala Pro Ala Gly Arg Leu Ser Gln Gly Ser<br>865                               870                     875                     880 | 2640 |
| ggc tct tcc atc aca gca gcc ggc atg cgc ctc agc cag atg ggt gtc<br>Gly Ser Ser Ile Thr Ala Ala Gly Met Arg Leu Ser Gln Met Gly Val<br>                  885                     890                     895 | 2688 |
| act acg gat ggt gtc ccc gcc cag caa ctg cgc atc cct ctt tcc ttc<br>Thr Thr Asp Gly Val Pro Ala Gln Gln Leu Arg Ile Pro Leu Ser Phe<br>          900                       905                       910 | 2736 |
| cag aac cct ctc ttc cat atg gct gcc gat gga cca ggg ccc cca gca<br>Gln Asn Pro Leu Phe His Met Ala Ala Asp Gly Pro Gly Pro Pro Ala<br>                 915                     920                     925 | 2784 |
| ggc cat gga ggg agc agt ggc cat ggt cca cct tcc tcc cat cac cac<br>Gly His Gly Gly Ser Ser Gly His Gly Pro Pro Ser Ser His His His<br>930                             935                     940 | 2832 |
| cac cac cac cat cac cat cac cga ggg gga gaa ccc cca ggg gac act<br>His His His His His His His Arg Gly Gly Glu Pro Pro Gly Asp Thr<br>945                             950                     955                     960 | 2880 |
| ttt gcc ccg ttc cat ggc tat agc aag agc gag gac ctc tct aca ggg<br>Phe Ala Pro Phe His Gly Tyr Ser Lys Ser Glu Asp Leu Ser Thr Gly<br>                 965                     970                     975 | 2928 |
| gtc cct aag ccc cct gcg gcc tcc atc ctt cac agc cac agc tac agt<br>Val Pro Lys Pro Pro Ala Ala Ser Ile Leu His Ser His Ser Tyr Ser<br>          980                       985                     990 | 2976 |
| gat gag ttt gga ccc tct ggt act gat ttt acc cgt cgg cag ctc tca<br>Asp Glu Phe Gly Pro Ser Gly Thr Asp Phe Thr Arg Arg Gln Leu Ser<br>          995                     1000                   1005 | 3024 |
| ctt cag gac aac cta cag cac atg ctc tcc ccg ccc cag atc acc atc<br>Leu Gln Asp Asn Leu Gln His Met Leu Ser Pro Pro Gln Ile Thr Ile<br>1010                           1015                    1020 | 3072 |
| ggt ccc cag agg cca gct ccc tca ggg cca gga ggg ggc agt ggt ggg<br>Gly Pro Gln Arg Pro Ala Pro Ser Gly Pro Gly Gly Gly Ser Gly Gly<br>1025                         1030                    1035                    1040 | 3120 |
| ggc agt ggt ggg ggc ggt ggg ggc cag cca cct ccc ttg cag agg ggc<br>Gly Ser Gly Gly Gly Gly Gly Gly Gln Pro Pro Pro Leu Gln Arg Gly<br>                 1045                    1050                    1055 | 3168 |
| aaa tct cag cag ttg aca gtg agt gct gcc cag aaa ccc cgg ccg tcc<br>Lys Ser Gln Gln Leu Thr Val Ser Ala Ala Gln Lys Pro Arg Pro Ser<br>1060                           1065                    1070 | 3216 |
| agc ggg aac cta ttg cag tcc ccg gaa cca agt tat ggt cct gcc cgt<br>Ser Gly Asn Leu Leu Gln Ser Pro Glu Pro Ser Tyr Gly Pro Ala Arg<br>                 1075                    1080                    1085 | 3264 |
| cca cgg caa cag agc ctc agc aaa gag ggc agc att ggg ggc agc ggg<br>Pro Arg Gln Gln Ser Leu Ser Lys Glu Gly Ser Ile Gly Gly Ser Gly<br>1090                           1095                    1100 | 3312 |
| ggc agc ggt ggc gga ggg ggt ggg ggg ctc aag ccc tcc atc acc aag<br>Gly Ser Gly Gly Gly Gly Gly Gly Gly Leu Lys Pro Ser Ile Thr Lys | 3360 |

-continued

```
                1105                1110                1115                1120
cag cat tcc cag act cca tcc acg ctg aac ccc acg atg ccg gcc tcg        3408
Gln His Ser Gln Thr Pro Ser Thr Leu Asn Pro Thr Met Pro Ala Ser
                1125                1130                1135 gag cgg act gta gcc tgg gtg tcc aat atg cct cac ctg tcc gct gac        3456
Glu Arg Thr Val Ala Trp Val Ser Asn Met Pro His Leu Ser Ala Asp
        1140                1145                1150 atc gag agt gca cac att gag cgg gaa gag tac aag ctg aag gag tac        3504
Ile Glu Ser Ala His Ile Glu Arg Glu Glu Tyr Lys Leu Lys Glu Tyr
        1155                1160                1165 tcg aag tcc atg gac gag agc cga ctg gac agg gtg aag gag tac gag        3552
Ser Lys Ser Met Asp Glu Ser Arg Leu Asp Arg Val Lys Glu Tyr Glu
        1170                1175                1180 gag gag atc cac tca ctg aag gaa agg cta cac atg tcc aac cgg aag        3600
Glu Glu Ile His Ser Leu Lys Glu Arg Leu His Met Ser Asn Arg Lys
1185                1190                1195                1200 ctg gaa gag tac gag cgg agg ctg ctg tcc cag gaa gag cag acc agc        3648
Leu Glu Glu Tyr Glu Arg Arg Leu Leu Ser Gln Glu Glu Gln Thr Ser
                1205                1210                1215 aag atc ctg atg cag tac caa gcc cgc ctg gag cag agc gag aag cgc        3696
Lys Ile Leu Met Gln Tyr Gln Ala Arg Leu Glu Gln Ser Glu Lys Arg
        1220                1225                1230 ttg agg cag cag cag gtg gag aag gac tcc cag atc aag agc atc att        3744
Leu Arg Gln Gln Gln Val Glu Lys Asp Ser Gln Ile Lys Ser Ile Ile
        1235                1240                1245 ggc agg ctg atg ctg gtg gag gag gag ctg cgc cgg gac cac ccc gcc        3792
Gly Arg Leu Met Leu Val Glu Glu Glu Leu Arg Arg Asp His Pro Ala
        1250                1255                1260 atg gct gag ccg ctg cct gaa ccc aag aag agg ctg ctc gac gct cag        3840
Met Ala Glu Pro Leu Pro Glu Pro Lys Lys Arg Leu Leu Asp Ala Gln
1265                1270                1275                1280 aga ggc agc ttc ccc cct tgg gtc caa caa acc cgc gtg tga cgc tgg        3888
Arg Gly Ser Phe Pro Pro Trp Val Gln Gln Thr Arg Val     Arg Trp
                1285                1290                    1295 ccc cac ctt gga acg gcc tgg ccc ccc cag ccc cac ccc ccc cac ccc        3936
Pro His Leu Gly Thr Ala Trp Pro Pro Gln Pro His Pro Pro His Pro
                1300                1305                1310 ggc tgc aga tca cag aga acg gcg agt tcc gga aca ccg cag acc act        3984
Gly Cys Arg Ser Gln Arg Thr Ala Ser Ser Gly Thr Pro Gln Thr Thr
        1315                1320                1325 agc cca ccc agc atc aca gac ctc ctt ccc tgt gca ccc tac ccc ggc        4032
Ser Pro Pro Ser Ile Thr Asp Leu Leu Pro Cys Ala Pro Tyr Pro Gly
1330                1335                1340 cca ccc agc gtc aca gac ctc ctt ccc agt gca ccc gac cct gga aca        4080
Pro Pro Ser Val Thr Asp Leu Leu Pro Ser Ala Pro Asp Pro Gly Thr
        1345                1350                1355 tca cca acc acc agg act gga cgt cac caa ggg aca gcg gga ttg tct        4128
Ser Pro Thr Thr Arg Thr Gly Arg His Gln Gly Thr Ala Gly Leu Ser
1360                1365                1370                1375 ccc tta acg cct cct tgg ggc acc cat ctg tca acc cca ctg ctc cat        4176
Pro Leu Thr Pro Pro Trp Gly Thr His Leu Ser Thr Pro Leu Leu His
        1380                1385                1390 tcc agg agg gag agt ggg acc ctc agc tgc cct ctc acc cca gga cac        4224
Ser Arg Arg Glu Ser Gly Thr Leu Ser Cys Pro Leu Thr Pro Gly His
        1395                1400                1405 cac cta ccc cac aca gac ccc ttc act ctg ggg tgc tat ccc cat cct        4272
His Leu Pro His Thr Asp Pro Phe Thr Leu Gly Cys Tyr Pro His Pro
        1410                1415                1420
```

-continued

```
<210> SEQ ID NO 2
<211> LENGTH: 1423
<212> TYPE: PRT
<213> ORGANISM: Unknown Organism
<220> FEATURE:
<223> OTHER INFORMATION: Description of Unknown Organism: mammalian
      SYNGAP-A

<400> SEQUENCE: 2

Met Ser Tyr Ala Pro Phe Arg Asp Val Arg Gly Pro Pro Met His Arg
  1               5                  10                  15

Thr Gln Tyr Val His Ser Pro Tyr Asp Arg Pro Gly Trp Asn Pro Arg
             20                  25                  30

Phe Cys Ile Ile Ser Gly Asn Gln Leu Leu Met Leu Asp Glu Asp Glu
         35                  40                  45

Ile His Pro Leu Leu Ile Arg Asp Arg Arg Ser Glu Ser Ser Arg Asn
     50                  55                  60

Lys Leu Leu Arg Arg Thr Val Ser Val Pro Val Glu Gly Arg Pro His
 65                  70                  75                  80

Gly Glu His Glu Tyr His Leu Gly Arg Ser Arg Arg Lys Ser Val Pro
                 85                  90                  95

Gly Gly Lys Gln Tyr Ser Met Glu Ala Ala Pro Ala Ala Pro Phe Arg
            100                 105                 110

Pro Ser Gln Gly Phe Leu Ser Arg Arg Leu Lys Ser Ser Ile Lys Arg
        115                 120                 125

Thr Lys Ser Gln Pro Lys Leu Asp Arg Thr Ser Ser Phe Arg Gln Ile
    130                 135                 140

Leu Pro Arg Phe Arg Ser Ala Asp His Asp Arg Ala Arg Leu Met Gln
145                 150                 155                 160

Ser Phe Lys Glu Ser His Ser His Glu Ser Leu Leu Ser Pro Ser Ser
                165                 170                 175

Ala Ala Glu Ala Leu Glu Leu Asn Leu Asp Glu Asp Ser Ile Ile Lys
            180                 185                 190

Pro Val His Ser Ser Ile Leu Gly Gln Glu Phe Cys Phe Glu Val Thr
        195                 200                 205

Thr Ser Ser Gly Thr Lys Cys Phe Ala Cys Arg Ser Ala Ala Glu Arg
    210                 215                 220

Asp Lys Trp Ile Glu Asn Leu Gln Arg Ala Val Lys Pro Asn Lys Asp
225                 230                 235                 240

Asn Ser Arg Arg Val Asp Asn Val Leu Lys Leu Trp Ile Ile Glu Ala
                245                 250                 255

Arg Glu Leu Pro Pro Lys Lys Arg Tyr Tyr Cys Glu Leu Cys Leu Asp
            260                 265                 270

Asp Met Leu Tyr Ala Arg Thr Thr Ser Lys Pro Arg Ser Ala Ser Gly
        275                 280                 285

Asp Thr Val Phe Trp Gly Glu His Phe Glu Phe Asn Asn Leu Pro Ala
    290                 295                 300

Val Arg Ala Leu Arg Leu His Leu Tyr Arg Asp Ser Asp Lys Lys Arg
305                 310                 315                 320

Lys Lys Asp Lys Ala Gly Tyr Val Gly Leu Val Thr Val Pro Val Ala
                325                 330                 335

Thr Leu Ala Gly Arg His Phe Thr Glu Gln Trp Tyr Pro Val Thr Leu
            340                 345                 350

Pro Thr Gly Ser Gly Gly Ser Gly Gly Met Gly Ser Gly Gly Gly Gly
        355                 360                 365
```

```
Gly Ser Gly Gly Gly Ser Gly Lys Gly Lys Gly Cys Pro Ala
    370                 375             380

Val Arg Leu Lys Ala Arg Tyr Gln Thr Met Ser Ile Leu Pro Met Glu
385                 390                 395                 400

Leu Tyr Lys Glu Phe Ala Glu Tyr Val Thr Asn His Tyr Arg Met Leu
                405                 410                 415

Cys Ala Val Leu Glu Pro Ala Leu Asn Val Lys Gly Lys Glu Glu Val
            420                 425                 430

Ala Ser Ala Leu Val His Ile Leu Gln Ser Thr Gly Lys Ala Lys Asp
        435                 440                 445

Phe Leu Ser Asp Met Ala Met Ser Glu Val Asp Arg Phe Met Glu Arg
    450                 455                 460

Glu His Leu Ile Phe Arg Glu Asn Thr Leu Ala Thr Lys Ala Ile Glu
465                 470                 475                 480

Glu Tyr Met Arg Leu Ile Gly Gln Lys Tyr Leu Lys Asp Ala Ile Gly
                485                 490                 495

Glu Phe Ile Arg Ala Leu Tyr Glu Ser Glu Asn Cys Glu Val Asp
            500                 505                 510

Pro Ile Lys Cys Thr Ala Ser Ser Leu Ala Glu His Gln Ala Asn Leu
    515                 520                 525

Arg Met Cys Cys Glu Leu Ala Leu Cys Lys Val Val Asn Ser His Cys
530                 535                 540

Val Phe Pro Arg Glu Leu Lys Glu Val Phe Ala Ser Trp Arg Leu Arg
545                 550                 555                 560

Cys Ala Glu Arg Gly Arg Glu Asp Ile Ala Asp Arg Leu Ile Ser Ala
                565                 570                 575

Ser Leu Phe Leu Arg Phe Leu Cys Pro Ala Ile Met Ser Pro Ser Leu
            580                 585                 590

Phe Gly Leu Met Gln Glu Tyr Pro Asp Glu Gln Thr Ser Arg Thr Leu
        595                 600                 605

Thr Leu Ile Ala Lys Val Ile Gln Asn Leu Ala Asn Phe Ser Lys Phe
    610                 615                 620

Thr Ser Lys Glu Asp Phe Leu Gly Phe Met Asn Glu Phe Leu Glu Leu
625                 630                 635                 640

Glu Trp Gly Ser Met Gln Gln Phe Leu Tyr Glu Ile Ser Asn Leu Asp
                645                 650                 655

Thr Leu Thr Asn Ser Ser Ser Phe Glu Gly Tyr Ile Asp Leu Gly Arg
            660                 665                 670

Glu Leu Ser Thr Leu His Ala Leu Leu Trp Glu Val Leu Pro Gln Leu
        675                 680                 685

Ser Lys Glu Ala Leu Leu Lys Leu Gly Pro Leu Pro Arg Leu Leu Ser
    690                 695                 700

Asp Ile Ser Thr Ala Leu Arg Asn Pro Asn Ile Gln Arg Gln Pro Ser
705                 710                 715                 720

Arg Gln Ser Glu Arg Ala Arg Ser Gln Pro Met Val Leu Arg Gly Pro
                725                 730                 735

Ser Ala Glu Met Gln Gly Tyr Met Met Arg Asp Leu Asn Ser Ser Ile
            740                 745                 750

Asp Leu Gln Ser Phe Met Ala Arg Gly Leu Asn Ser Ser Met Asp Met
        755                 760                 765

Ala Arg Leu Pro Ser Pro Thr Lys Glu Lys Pro Pro Pro Pro Pro
    770                 775                 780

Gly Gly Gly Lys Asp Leu Phe Tyr Val Ser Arg Pro Pro Leu Ala Arg
```

-continued

```
            785                 790                 795                 800

Ser Ser Pro Ala Tyr Cys Thr Ser Ser Ser Asp Ile Thr Glu Pro Glu
                    805                 810                 815

Gln Lys Met Leu Ser Val Asn Lys Ser Val Ser Met Leu Asp Leu Gln
                820                 825                 830

Gly Asp Gly Pro Gly Gly Arg Leu Asn Ser Ser Val Ser Asn Leu
            835                 840                 845

Ala Ala Val Gly Asp Leu Leu His Ser Ser Gln Ala Ser Leu Thr Ala
        850                 855                 860

Ala Leu Gly Leu Arg Pro Ala Pro Ala Gly Arg Leu Ser Gln Gly Ser
865                 870                 875                 880

Gly Ser Ser Ile Thr Ala Ala Gly Met Arg Leu Ser Gln Met Gly Val
                885                 890                 895

Thr Thr Asp Gly Val Pro Ala Gln Gln Leu Arg Ile Pro Leu Ser Phe
                900                 905                 910

Gln Asn Pro Leu Phe His Met Ala Ala Asp Gly Pro Gly Pro Pro Ala
            915                 920                 925

Gly His Gly Gly Ser Ser Gly His Gly Pro Ser Ser His His His
        930                 935                 940

His His His His His His His Arg Gly Gly Glu Pro Pro Gly Asp Thr
945                 950                 955                 960

Phe Ala Pro Phe His Gly Tyr Ser Lys Ser Glu Asp Leu Ser Thr Gly
                965                 970                 975

Val Pro Lys Pro Pro Ala Ala Ser Ile Leu His Ser His Ser Tyr Ser
                980                 985                 990

Asp Glu Phe Gly Pro Ser Gly Thr Asp Phe Thr Arg Arg Gln Leu Ser
            995                 1000                1005

Leu Gln Asp Asn Leu Gln His Met Leu Ser Pro Pro Gln Ile Thr Ile
        1010                1015                1020

Gly Pro Gln Arg Pro Ala Pro Ser Gly Pro Gly Gly Ser Gly Gly
1025                1030                1035                1040

Gly Ser Gly Gly Gly Gly Gly Gln Pro Pro Leu Gln Arg Gly
                1045                1050                1055

Lys Ser Gln Gln Leu Thr Val Ser Ala Ala Gln Lys Pro Arg Pro Ser
                1060                1065                1070

Ser Gly Asn Leu Leu Gln Ser Pro Glu Pro Ser Tyr Gly Pro Ala Arg
            1075                1080                1085

Pro Arg Gln Gln Ser Leu Ser Lys Glu Gly Ser Ile Gly Gly Ser Gly
        1090                1095                1100

Gly Ser Gly Gly Gly Gly Gly Gly Leu Lys Pro Ser Ile Thr Lys
1105                1110                1115                1120

Gln His Ser Gln Thr Pro Ser Thr Leu Asn Pro Thr Met Pro Ala Ser
                1125                1130                1135

Glu Arg Thr Val Ala Trp Val Ser Asn Met Pro His Leu Ser Ala Asp
                1140                1145                1150

Ile Glu Ser Ala His Ile Glu Arg Glu Glu Tyr Lys Leu Lys Glu Tyr
            1155                1160                1165

Ser Lys Ser Met Asp Glu Ser Arg Leu Asp Arg Val Lys Glu Tyr Glu
        1170                1175                1180

Glu Glu Ile His Ser Leu Lys Glu Arg Leu His Met Ser Asn Arg Lys
1185                1190                1195                1200

Leu Glu Glu Tyr Glu Arg Arg Leu Leu Ser Gln Glu Gln Thr Ser
                1205                1210                1215
```

-continued

```
Lys Ile Leu Met Gln Tyr Gln Ala Arg Leu Glu Gln Ser Glu Lys Arg
        1220                1225                1230

Leu Arg Gln Gln Gln Val Glu Lys Asp Ser Gln Ile Lys Ser Ile Ile
    1235                1240                1245

Gly Arg Leu Met Leu Val Glu Glu Leu Arg Arg Asp His Pro Ala
        1250                1255                1260

Met Ala Glu Pro Leu Pro Glu Pro Lys Lys Arg Leu Leu Asp Ala Gln
1265                1270                1275                1280

Arg Gly Ser Phe Pro Pro Trp Val Gln Gln Thr Arg Val Arg Trp Pro
            1285                1290                1295

His Leu Gly Thr Ala Trp Pro Pro Gln Pro His Pro Pro His Pro Gly
        1300                1305                1310

Cys Arg Ser Gln Arg Thr Ala Ser Ser Gly Thr Pro Gln Thr Thr Ser
        1315                1320                1325

Pro Pro Ser Ile Thr Asp Leu Leu Pro Cys Ala Pro Tyr Pro Gly Pro
        1330                1335                1340

Pro Ser Val Thr Asp Leu Leu Pro Ser Ala Pro Asp Pro Gly Thr Ser
1345                1350                1355                1360

Pro Thr Thr Arg Thr Gly Arg His Gln Gly Thr Ala Gly Leu Ser Pro
            1365                1370                1375

Leu Thr Pro Pro Trp Gly Thr His Leu Ser Thr Pro Leu Leu His Ser
        1380                1385                1390

Arg Arg Glu Ser Gly Thr Leu Ser Cys Pro Leu Thr Pro Gly His His
            1395                1400                1405

Leu Pro His Thr Asp Pro Phe Thr Leu Gly Cys Tyr Pro His Pro
        1410                1415                1420

<210> SEQ ID NO 3
<211> LENGTH: 4134
<212> TYPE: DNA
<213> ORGANISM: Unknown Organism
<220> FEATURE:
<223> OTHER INFORMATION: Description of Unknown Organism: mammalian
      SYNGAP-B
<220> FEATURE:
<221> NAME/KEY: CDS
<222> LOCATION: (4)..(3741)
<220> FEATURE:
<221> NAME/KEY: CDS
<222> LOCATION: (3745)..(4134)

<400> SEQUENCE: 3 taa ggc ccc cca ccc cga ccc cgt cag ggg gct ccg gtt cag gtt cct      48
    Gly Pro Pro Pro Arg Pro Arg Gln Gly Ala Pro Val Gln Val Pro
    1               5                   10                  15 tgc ccc ctc ctt ccc acc gcc agc ctc tcc gcc gcc gct gct ctt cct      96
Cys Pro Leu Leu Pro Thr Ala Ser Leu Ser Ala Ala Ala Ala Leu Pro
            20                  25                  30 gct gct ttc cgg ggg aat acc act tgg gtc gct cga gga gga aga gtg     144
Ala Ala Phe Arg Gly Asn Thr Thr Trp Val Ala Arg Gly Gly Arg Val
        35                  40                  45 tcc ccg ggg ggg aaa cag tac agc atg gaa gcc gcc ccc gct gcg ccc     192
Ser Pro Gly Gly Lys Gln Tyr Ser Met Glu Ala Ala Pro Ala Ala Pro
    50                  55                  60 ttc cgg ccc tcg caa ggc ttc ctg agc cgg agg cta aaa agc tcc atc     240
Phe Arg Pro Ser Gln Gly Phe Leu Ser Arg Arg Leu Lys Ser Ser Ile
65                  70                  75 aaa cgt aca aag tca caa ccc aaa ctt gac cgg acc agc agc ttt cga     288
Lys Arg Thr Lys Ser Gln Pro Lys Leu Asp Arg Thr Ser Ser Phe Arg
```

```
         80                  85                  90                  95
cag atc ctg cct cgc ttc cga agt gct gac cat gac cgg gcc cgg ctg      336
Gln Ile Leu Pro Arg Phe Arg Ser Ala Asp His Asp Arg Ala Arg Leu
            100                 105                 110 atg cag agc ttc aag gag tct cac tcc cat gag tcc ctg ctg agt ccc      384
Met Gln Ser Phe Lys Glu Ser His Ser His Glu Ser Leu Leu Ser Pro
            115                 120                 125 agc agt gct gct gag gcc ctg gag ctc aac ctg gat gaa gac tcc att      432
Ser Ser Ala Ala Glu Ala Leu Glu Leu Asn Leu Asp Glu Asp Ser Ile
            130                 135                 140 atc aag cca gta cac agc tcc atc ctg ggc cag gag ttc tgc ttt gag      480
Ile Lys Pro Val His Ser Ser Ile Leu Gly Gln Glu Phe Cys Phe Glu
            145                 150                 155 gta aca aca tcg tct ggg aca aaa tgt ttt gcc tgt cgg tct gca gcc      528
Val Thr Thr Ser Ser Gly Thr Lys Cys Phe Ala Cys Arg Ser Ala Ala
160                 165                 170                 175 gaa agg gac aaa tgg att gag aat cta cag agg gct gtg aaa ccc aac      576
Glu Arg Asp Lys Trp Ile Glu Asn Leu Gln Arg Ala Val Lys Pro Asn
            180                 185                 190 aag gac aac agc cgc cgg gta gat aac gtg ctg aaa cta tgg atc ata      624
Lys Asp Asn Ser Arg Arg Val Asp Asn Val Leu Lys Leu Trp Ile Ile
            195                 200                 205 gaa gct cga gag ctg ccc ccc aag aag cga tat tac tgc gag tta tgc      672
Glu Ala Arg Glu Leu Pro Pro Lys Lys Arg Tyr Tyr Cys Glu Leu Cys
            210                 215                 220 ctg gac gac atg ctc tat gca cgg acc act tcc aag ccc cgc tca gcc      720
Leu Asp Asp Met Leu Tyr Ala Arg Thr Thr Ser Lys Pro Arg Ser Ala
225                 230                 235 tca gga gac act gtc ttt tgg ggc gag cac ttc gag ttt aac aac ctg      768
Ser Gly Asp Thr Val Phe Trp Gly Glu His Phe Glu Phe Asn Asn Leu
240                 245                 250                 255 cct gct gtc cgg gcg ctg cgg ctg cat ctg tac cgt gac tcg gac aaa      816
Pro Ala Val Arg Ala Leu Arg Leu His Leu Tyr Arg Asp Ser Asp Lys
            260                 265                 270 aag cgg aag aag gac aag gca ggc tac gtt ggc ctg gtg act gtt cca      864
Lys Arg Lys Lys Asp Lys Ala Gly Tyr Val Gly Leu Val Thr Val Pro
            275                 280                 285 gtg gcc acc ctg gct ggg cgc cac ttc aca gag cag tgg tac ccc gtg      912
Val Ala Thr Leu Ala Gly Arg His Phe Thr Glu Gln Trp Tyr Pro Val
            290                 295                 300 acc ctg cca aca gga agt ggg ggc tct ggg ggt atg ggc tcg ggg gga      960
Thr Leu Pro Thr Gly Ser Gly Gly Ser Gly Gly Met Gly Ser Gly Gly
            305                 310                 315 gga ggg ggg tca ggg ggc ggc tca ggg ggc aaa ggg aaa gga ggc tgt     1008
Gly Gly Gly Ser Gly Gly Gly Ser Gly Gly Lys Gly Lys Gly Gly Cys
320                 325                 330                 335 cct gct gtg cgg ctg aag gcc cgt tac cag aca atg agt atc ctg ccc     1056
Pro Ala Val Arg Leu Lys Ala Arg Tyr Gln Thr Met Ser Ile Leu Pro
            340                 345                 350 atg gag cta tat aag gag ttt gca gaa tat gtg acc aac cac tac cgc     1104
Met Glu Leu Tyr Lys Glu Phe Ala Glu Tyr Val Thr Asn His Tyr Arg
            355                 360                 365 atg ctg tgt gcc gtg ctg gag ccc gcc ctc aat gtc aag ggc aag gag     1152
Met Leu Cys Ala Val Leu Glu Pro Ala Leu Asn Val Lys Gly Lys Glu
            370                 375                 380 gag gtc gct agt gca ctg gtt cac atc ctg caa agc aca ggc aag gcc     1200
Glu Val Ala Ser Ala Leu Val His Ile Leu Gln Ser Thr Gly Lys Ala
385                 390                 395 aag gac ttc ctt tca gac atg gcc atg tca gag gta gac cgg ttc atg     1248
```

-continued

```
Lys Asp Phe Leu Ser Asp Met Ala Met Ser Glu Val Asp Arg Phe Met
400                 405                 410                 415 gag cgg gaa cac ctc ata ttc cgc gag aac acg ctc gcc act aaa gcc    1296
Glu Arg Glu His Leu Ile Phe Arg Glu Asn Thr Leu Ala Thr Lys Ala
                420                 425                 430 ata gaa gag tat atg aga ctg att ggc cag aaa tac ctc aag gat gcc    1344
Ile Glu Glu Tyr Met Arg Leu Ile Gly Gln Lys Tyr Leu Lys Asp Ala
            435                 440                 445 att ggg gag ttc atc cgg gct ctg tat gaa tct gag gag aac tgt gaa    1392
Ile Gly Glu Phe Ile Arg Ala Leu Tyr Glu Ser Glu Glu Asn Cys Glu
        450                 455                 460 gta gac ccc atc aag tgc aca gcg tcc agt ctg gca gag cac cag gcc    1440
Val Asp Pro Ile Lys Cys Thr Ala Ser Ser Leu Ala Glu His Gln Ala 465                 470                 475 aac ctg cgg atg tgc tgt gag ttg gcc ctg tgc aag gtg gtc aac tcc    1488
Asn Leu Arg Met Cys Cys Glu Leu Ala Leu Cys Lys Val Val Asn Ser
480                 485                 490                 495 cat tgc gtg ttc ccg agg gag ctg aag gag gtg ttt gca tca tgg cgg    1536
His Cys Val Phe Pro Arg Glu Leu Lys Glu Val Phe Ala Ser Trp Arg
                500                 505                 510 ctg cgc tgt gca gag cgg ggc cgg gag gac att gct gac agg ctg atc    1584
Leu Arg Cys Ala Glu Arg Gly Arg Glu Asp Ile Ala Asp Arg Leu Ile
            515                 520                 525 agc gcc tcg ctc ttc ctg cgc ttc ctc tgc ccg gcc atc atg tcg ccc    1632
Ser Ala Ser Leu Phe Leu Arg Phe Leu Cys Pro Ala Ile Met Ser Pro
        530                 535                 540 agt ctg ttt gga ctg atg cag gag tac cca gat gag cag acc tca cga    1680
Ser Leu Phe Gly Leu Met Gln Glu Tyr Pro Asp Glu Gln Thr Ser Arg
    545                 550                 555 acc ctc acc ctc atc gcc aag gtt atc cag aac ctg gcc aac ttt tcc    1728
Thr Leu Thr Leu Ile Ala Lys Val Ile Gln Asn Leu Ala Asn Phe Ser
560                 565                 570                 575 aag ttt acc tca aag gag gac ttc ctg ggc ttc atg aac gag ttt ctg    1776
Lys Phe Thr Ser Lys Glu Asp Phe Leu Gly Phe Met Asn Glu Phe Leu
                580                 585                 590 gag ctg gag tgg ggt tct atg cag caa ttc ttg tat gag ata tcc aac    1824
Glu Leu Glu Trp Gly Ser Met Gln Gln Phe Leu Tyr Glu Ile Ser Asn
            595                 600                 605 ctg gac aca ctg acc aac agc agc agt ttt gag ggc tac ata gac ttg    1872
Leu Asp Thr Leu Thr Asn Ser Ser Ser Phe Glu Gly Tyr Ile Asp Leu
        610                 615                 620 ggc cgc gag ctc tcc aca ctt cac gcc ctg ctc tgg gag gtg ctg ccc    1920
Gly Arg Glu Leu Ser Thr Leu His Ala Leu Leu Trp Glu Val Leu Pro
    625                 630                 635 cag ctc agc aag gaa gcc ctc ctg aag ctg ggc ccg ctg ccc cgg ctc    1968
Gln Leu Ser Lys Glu Ala Leu Leu Lys Leu Gly Pro Leu Pro Arg Leu
640                 645                 650                 655 ctc agc gac atc agc aca gcc ctg agg aac cct aac atc caa agg cag    2016
Leu Ser Asp Ile Ser Thr Ala Leu Arg Asn Pro Asn Ile Gln Arg Gln
                660                 665                 670 ccg agc cgc cag agc gag cgc gct cgg tct cag ccc atg gtg ctg cgc    2064
Pro Ser Arg Gln Ser Glu Arg Ala Arg Ser Gln Pro Met Val Leu Arg
            675                 680                 685 ggg ccg tca gcc gag atg cag ggc tac atg atg cgg gac ctc aac agc    2112
Gly Pro Ser Ala Glu Met Gln Gly Tyr Met Met Arg Asp Leu Asn Ser
        690                 695                 700 tcc atc gac ctt cag tcc ttc atg gct cga ggc ctc aac agc tct atg    2160
Ser Ile Asp Leu Gln Ser Phe Met Ala Arg Gly Leu Asn Ser Ser Met
    705                 710                 715
```

-continued

```
gac atg gct cgc ctc ccc tcc cca acc aag gag aaa ccc ccg ccg ccc      2208
Asp Met Ala Arg Leu Pro Ser Pro Thr Lys Glu Lys Pro Pro Pro Pro
720                 725                 730                 735 cct ccc ggt ggg ggt aaa gac ctg ttc tat gtg agc cgg cca cca ctg      2256
Pro Pro Gly Gly Gly Lys Asp Leu Phe Tyr Val Ser Arg Pro Pro Leu
                740                 745                 750 gcc cgg tcc tcc cca gca tac tgc acg agc agc tcg gac atc aca gag      2304
Ala Arg Ser Ser Pro Ala Tyr Cys Thr Ser Ser Ser Asp Ile Thr Glu
            755                 760                 765 ccg gag cag aag atg ctg agt gtc aac aag agt gtg tcc atg ctg gac      2352
Pro Glu Gln Lys Met Leu Ser Val Asn Lys Ser Val Ser Met Leu Asp
        770                 775                 780 ctg cag ggc gac ggg cct ggg ggc cgc ctt aac agc agt agt gtt tcc      2400
Leu Gln Gly Asp Gly Pro Gly Gly Arg Leu Asn Ser Ser Ser Val Ser
785                 790                 795 aac ctg gca gct gtt ggg gac ctg ttg cac tca agc cag gct tca ctg      2448
Asn Leu Ala Ala Val Gly Asp Leu Leu His Ser Ser Gln Ala Ser Leu
800                 805                 810                 815 aca gca gcc ttg ggg ttg cgg cct gca cct gcc ggg cgc ctc tcc caa      2496
Thr Ala Ala Leu Gly Leu Arg Pro Ala Pro Ala Gly Arg Leu Ser Gln
                820                 825                 830 ggg agt ggc tct tcc atc aca gca gcc ggc atg cgc ctc agc cag atg      2544
Gly Ser Gly Ser Ser Ile Thr Ala Ala Gly Met Arg Leu Ser Gln Met
            835                 840                 845 ggt gtc act acg gat ggt gtc ccc gcc cag caa ctg cgc atc cct ctt      2592
Gly Val Thr Thr Asp Gly Val Pro Ala Gln Gln Leu Arg Ile Pro Leu
        850                 855                 860 tcc ttc cag aac cct ctc ttc cat atg gct gcc gat gga cca ggg ccc      2640
Ser Phe Gln Asn Pro Leu Phe His Met Ala Ala Asp Gly Pro Gly Pro
865                 870                 875 cca gca ggc cat gga ggg agc agt ggc cat ggt cca cct tcc tcc cat      2688
Pro Ala Gly His Gly Gly Ser Ser Gly His Gly Pro Pro Ser Ser His
880                 885                 890                 895 cac cac cac cac cac cat cac cat cac cga ggg gga gaa ccc cca ggg      2736
His His His His His His His His His Arg Gly Gly Glu Pro Pro Gly
                900                 905                 910 gac act ttt gcc ccg ttc cat ggc tat agc aag agc gag gac ctc tct      2784
Asp Thr Phe Ala Pro Phe His Gly Tyr Ser Lys Ser Glu Asp Leu Ser
            915                 920                 925 aca ggg gtc cct aag ccc cct gcg gcc tcc atc ctt cac agc cac agc      2832
Thr Gly Val Pro Lys Pro Pro Ala Ala Ser Ile Leu His Ser His Ser
        930                 935                 940 tac agt gat gag ttt gga ccc tct ggt act gat ttt acc cgt cgg cag      2880
Tyr Ser Asp Glu Phe Gly Pro Ser Gly Thr Asp Phe Thr Arg Arg Gln
945                 950                 955 ctc tca ctt cag gac aac cta cag cac atg ctc tcc ccg ccc cag atc      2928
Leu Ser Leu Gln Asp Asn Leu Gln His Met Leu Ser Pro Pro Gln Ile
960                 965                 970                 975 acc atc ggt ccc cag agg cca gct ccc tca ggg cca gga ggg ggc agt      2976
Thr Ile Gly Pro Gln Arg Pro Ala Pro Ser Gly Pro Gly Gly Gly Ser
                980                 985                 990 ggt ggg ggc agt ggt ggg ggc ggt ggg ggc cag cca cct ccc ttg cag      3024
Gly Gly Gly Ser Gly Gly Gly Gly Gly Gly Gln Pro Pro Pro Leu Gln
            995                 1000                1005 agg ggc aaa tct cag cag ttg aca gtg agt gct gcc cag aaa ccc cgg      3072
Arg Gly Lys Ser Gln Gln Leu Thr Val Ser Ala Ala Gln Lys Pro Arg
        1010                1015                1020 ccg tcc agc ggg aac cta ttg cag tcc ccg gaa cca agt tat ggt cct      3120
Pro Ser Ser Gly Asn Leu Leu Gln Ser Pro Glu Pro Ser Tyr Gly Pro
```

```
                                          -continued 1025                1030              1035 gcc cgt cca cgg caa cag agc ctc agc aaa gag ggc agc att ggg ggc      3168
Ala Arg Pro Arg Gln Gln Ser Leu Ser Lys Glu Gly Ser Ile Gly Gly
1040              1045              1050              1055 agc ggg ggc agc ggt ggc gga ggg ggt ggg ggg ctc aag ccc tcc atc      3216
Ser Gly Gly Ser Gly Gly Gly Gly Gly Gly Gly Leu Lys Pro Ser Ile
              1060              1065              1070 acc aag cag cat tcc cag act cca tcc acg ctg aac ccc acg atg ccg      3264
Thr Lys Gln His Ser Gln Thr Pro Ser Thr Leu Asn Pro Thr Met Pro
     1075              1080              1085 gcc tcg gag cgg act gta gcc tgg gtg tcc aat atg cct cac ctg tcc      3312
Ala Ser Glu Arg Thr Val Ala Trp Val Ser Asn Met Pro His Leu Ser
         1090              1095              1100 gct gac atc gag agt gca cac att gag cgg gaa gag tac aag ctg aag      3360
Ala Asp Ile Glu Ser Ala His Ile Glu Arg Glu Glu Tyr Lys Leu Lys
    1105              1110              1115 gag tac tcg aag tcc atg gac gag agc cga ctg gac agg gtg aag gag      3408
Glu Tyr Ser Lys Ser Met Asp Glu Ser Arg Leu Asp Arg Val Lys Glu
1120              1125              1130              1135 tac gag gag gag atc cac tca ctg aag gaa agg cta cac atg tcc aac      3456
Tyr Glu Glu Glu Ile His Ser Leu Lys Glu Arg Leu His Met Ser Asn
              1140              1145              1150 cgg aag ctg gaa gag tac gag cgg agg ctg ctg tcc cag gaa gag cag      3504
Arg Lys Leu Glu Glu Tyr Glu Arg Arg Leu Leu Ser Gln Glu Glu Gln
     1155              1160              1165 acc agc aag atc ctg atg cag tac caa gcc cgc ctg gag cag agc gag      3552
Thr Ser Lys Ile Leu Met Gln Tyr Gln Ala Arg Leu Glu Gln Ser Glu
         1170              1175              1180 aag cgc ttg agg cag cag cag gtg gag aag gac tcc cag atc aag agc      3600
Lys Arg Leu Arg Gln Gln Gln Val Glu Lys Asp Ser Gln Ile Lys Ser
    1185              1190              1195 atc att ggc agg ctg atg ctg gtg gag gag gag ctg cgc cgg gac cac      3648
Ile Ile Gly Arg Leu Met Leu Val Glu Glu Glu Leu Arg Arg Asp His
1200              1205              1210              1215 ccc gcc atg gct gag ccg ctg cct gaa ccc aag aag agg ctg ctc gac      3696
Pro Ala Met Ala Glu Pro Leu Pro Glu Pro Lys Lys Arg Leu Leu Asp
              1220              1225              1230 gct cag aga ggc agc ttc ccc cct tgg gtc caa caa acc cgc gtg           3741
Ala Gln Arg Gly Ser Phe Pro Pro Trp Val Gln Gln Thr Arg Val
     1235              1240              1245 tga cgc tgg ccc cac ctt gga acg gcc tgg ccc ccc cag ccc cac ccc      3789
    Arg Trp Pro His Leu Gly Thr Ala Trp Pro Pro Gln Pro His Pro
         1250              1255              1260 ccc cac ccc ggc tgc aga tca cag aga acg gcg agt tcc gga aca ccg      3837
Pro His Pro Gly Cys Arg Ser Gln Arg Thr Ala Ser Ser Gly Thr Pro
    1265              1270              1275 cag acc act agc cca ccc agc atc aca gac ctc ctt ccc tgt gca ccc      3885
Gln Thr Thr Ser Pro Pro Ser Ile Thr Asp Leu Leu Pro Cys Ala Pro
1280              1285              1290 tac ccc ggc cca ccc agc gtc aca gac ctc ctt ccc agt gca ccc gac      3933
Tyr Pro Gly Pro Pro Ser Val Thr Asp Leu Leu Pro Ser Ala Pro Asp
     1295              1300              1305 cct gga aca tca cca acc acc agg act gga cgt cac caa ggg aca gcg      3981
Pro Gly Thr Ser Pro Thr Thr Arg Thr Gly Arg His Gln Gly Thr Ala
1310              1315              1320              1325 gga ttg tct ccc tta acg cct cct tgg ggc acc cat ctg tca acc cca      4029
Gly Leu Ser Pro Leu Thr Pro Pro Trp Gly Thr His Leu Ser Thr Pro
              1330              1335              1340 ctg ctc cat tcc agg agg gag agt ggg acc ctc agc tgc cct ctc acc      4077
```

| | | | | | | | | | | | | | |
|---|---|---|---|---|---|---|---|---|---|---|---|---|---|
|Leu|Leu|His|Ser|Arg|Arg|Glu|Ser|Gly|Thr|Leu|Ser|Cys|Pro Leu Thr|
| | |1345| | | |1350| | | |1355| | | |

```
cca gga cac cac cta ccc cac aca gac ccc ttc act ctg ggg tgc tat      4125
Pro Gly His His Leu Pro His Thr Asp Pro Phe Thr Leu Gly Cys Tyr
        1360                1365                1370 ccc cat cct                                                          4134
Pro His Pro
    1375
```

<210> SEQ ID NO 4
<211> LENGTH: 1376
<212> TYPE: PRT
<213> ORGANISM: Unknown Organism
<220> FEATURE:
<223> OTHER INFORMATION: Description of Unknown Organism: mammalian SYNGAP-B

<400> SEQUENCE: 4

```
Gly Pro Pro Pro Arg Pro Arg Gln Gly Ala Pro Val Gln Val Pro Cys
 1               5                  10                  15

Pro Leu Leu Pro Thr Ala Ser Leu Ser Ala Ala Ala Leu Pro Ala
            20                  25                  30

Ala Phe Arg Gly Asn Thr Thr Trp Val Ala Arg Gly Gly Arg Val Ser
        35                  40                  45

Pro Gly Gly Lys Gln Tyr Ser Met Glu Ala Ala Pro Ala Ala Pro Phe
    50                  55                  60

Arg Pro Ser Gln Gly Phe Leu Ser Arg Arg Leu Lys Ser Ser Ile Lys
 65                  70                  75                  80

Arg Thr Lys Ser Gln Pro Lys Leu Asp Arg Thr Ser Ser Phe Arg Gln
                85                  90                  95

Ile Leu Pro Arg Phe Arg Ser Ala Asp His Asp Arg Ala Arg Leu Met
            100                 105                 110

Gln Ser Phe Lys Glu Ser His Ser His Glu Ser Leu Leu Ser Pro Ser
        115                 120                 125

Ser Ala Ala Glu Ala Leu Glu Leu Asn Leu Asp Glu Asp Ser Ile Ile
    130                 135                 140

Lys Pro Val His Ser Ser Ile Leu Gly Gln Glu Phe Cys Phe Glu Val
145                 150                 155                 160

Thr Thr Ser Ser Gly Thr Lys Cys Phe Ala Cys Arg Ser Ala Ala Glu
                165                 170                 175

Arg Asp Lys Trp Ile Glu Asn Leu Gln Arg Ala Val Lys Pro Asn Lys
            180                 185                 190

Asp Asn Ser Arg Arg Val Asp Asn Val Leu Lys Leu Trp Ile Ile Glu
        195                 200                 205

Ala Arg Glu Leu Pro Pro Lys Lys Arg Tyr Tyr Cys Glu Leu Cys Leu
    210                 215                 220

Asp Asp Met Leu Tyr Ala Arg Thr Thr Ser Lys Pro Arg Ser Ala Ser
225                 230                 235                 240

Gly Asp Thr Val Phe Trp Gly Glu His Phe Glu Phe Asn Asn Leu Pro
                245                 250                 255

Ala Val Arg Ala Leu Arg Leu His Leu Tyr Arg Asp Ser Asp Lys Lys
            260                 265                 270

Arg Lys Lys Asp Lys Ala Gly Tyr Val Gly Leu Val Thr Val Pro Val
        275                 280                 285

Ala Thr Leu Ala Gly Arg His Phe Thr Glu Gln Trp Tyr Pro Val Thr
    290                 295                 300
```

-continued

```
Leu Pro Thr Gly Ser Gly Gly Ser Gly Met Gly Ser Gly Gly Gly
305                 310                 315                 320

Gly Gly Ser Gly Gly Gly Ser Gly Gly Lys Gly Lys Gly Gly Cys Pro
            325                 330                 335

Ala Val Arg Leu Lys Ala Arg Tyr Gln Thr Met Ser Ile Leu Pro Met
            340                 345                 350

Glu Leu Tyr Lys Glu Phe Ala Glu Tyr Val Thr Asn His Tyr Arg Met
            355                 360                 365

Leu Cys Ala Val Leu Glu Pro Ala Leu Asn Val Lys Gly Lys Glu Glu
    370                 375                 380

Val Ala Ser Ala Leu Val His Ile Leu Gln Ser Thr Gly Lys Ala Lys
385                 390                 395                 400

Asp Phe Leu Ser Asp Met Ala Met Ser Glu Val Asp Arg Phe Met Glu
            405                 410                 415

Arg Glu His Leu Ile Phe Arg Glu Asn Thr Leu Ala Thr Lys Ala Ile
            420                 425                 430

Glu Glu Tyr Met Arg Leu Ile Gly Gln Lys Tyr Leu Lys Asp Ala Ile
            435                 440                 445

Gly Glu Phe Ile Arg Ala Leu Tyr Glu Ser Glu Glu Asn Cys Glu Val
    450                 455                 460

Asp Pro Ile Lys Cys Thr Ala Ser Ser Leu Ala Glu His Gln Ala Asn
465                 470                 475                 480

Leu Arg Met Cys Cys Glu Leu Ala Leu Cys Lys Val Val Asn Ser His
            485                 490                 495

Cys Val Phe Pro Arg Glu Leu Lys Glu Val Phe Ala Ser Trp Arg Leu
            500                 505                 510

Arg Cys Ala Glu Arg Gly Arg Glu Asp Ile Ala Asp Arg Leu Ile Ser
            515                 520                 525

Ala Ser Leu Phe Leu Arg Phe Leu Cys Pro Ala Ile Met Ser Pro Ser
            530                 535                 540

Leu Phe Gly Leu Met Gln Glu Tyr Pro Asp Glu Gln Thr Ser Arg Thr
545                 550                 555                 560

Leu Thr Leu Ile Ala Lys Val Ile Gln Asn Leu Ala Asn Phe Ser Lys
            565                 570                 575

Phe Thr Ser Lys Glu Asp Phe Leu Gly Phe Met Asn Glu Phe Leu Glu
            580                 585                 590

Leu Glu Trp Gly Ser Met Gln Gln Phe Leu Tyr Glu Ile Ser Asn Leu
            595                 600                 605

Asp Thr Leu Thr Asn Ser Ser Ser Phe Glu Gly Tyr Ile Asp Leu Gly
    610                 615                 620

Arg Glu Leu Ser Thr Leu His Ala Leu Leu Trp Glu Val Leu Pro Gln
625                 630                 635                 640

Leu Ser Lys Glu Ala Leu Leu Lys Leu Gly Pro Leu Pro Arg Leu Leu
            645                 650                 655

Ser Asp Ile Ser Thr Ala Leu Arg Asn Pro Asn Ile Gln Arg Gln Pro
            660                 665                 670

Ser Arg Gln Ser Glu Arg Ala Arg Ser Gln Pro Met Val Leu Arg Gly
            675                 680                 685

Pro Ser Ala Glu Met Gln Gly Tyr Met Met Arg Asp Leu Asn Ser Ser
    690                 695                 700

Ile Asp Leu Gln Ser Phe Met Ala Arg Gly Leu Asn Ser Ser Met Asp
705                 710                 715                 720

Met Ala Arg Leu Pro Ser Pro Thr Lys Glu Lys Pro Pro Pro Pro
```

-continued

```
                725                 730                 735
Pro Gly Gly Lys Asp Leu Phe Tyr Val Ser Arg Pro Pro Leu Ala
            740                 745                 750
Arg Ser Ser Pro Ala Tyr Cys Thr Ser Ser Asp Ile Thr Glu Pro
            755                 760                 765
Glu Gln Lys Met Leu Ser Val Asn Lys Ser Val Ser Met Leu Asp Leu
            770                 775                 780
Gln Gly Asp Gly Pro Gly Gly Arg Leu Asn Ser Ser Val Ser Asn
785             790                 795                 800
Leu Ala Ala Val Gly Asp Leu Leu His Ser Ser Gln Ala Ser Leu Thr
                805                 810                 815
Ala Ala Leu Gly Leu Arg Pro Ala Pro Ala Gly Arg Leu Ser Gln Gly
            820                 825                 830
Ser Gly Ser Ser Ile Thr Ala Ala Gly Met Arg Leu Ser Gln Met Gly
            835                 840                 845
Val Thr Thr Asp Gly Val Pro Ala Gln Gln Leu Arg Ile Pro Leu Ser
    850                 855                 860
Phe Gln Asn Pro Leu Phe His Met Ala Ala Asp Gly Pro Gly Pro Pro
865                 870                 875                 880
Ala Gly His Gly Gly Ser Ser Gly His Gly Pro Pro Ser Ser His His
            885                 890                 895
His His His His His His His Arg Gly Gly Glu Pro Pro Gly Asp
            900                 905                 910
Thr Phe Ala Pro Phe His Gly Tyr Ser Lys Ser Glu Asp Leu Ser Thr
            915                 920                 925
Gly Val Pro Lys Pro Pro Ala Ala Ser Ile Leu His Ser His Ser Tyr
            930                 935                 940
Ser Asp Glu Phe Gly Pro Ser Gly Thr Asp Phe Thr Arg Arg Gln Leu
945                 950                 955                 960
Ser Leu Gln Asp Asn Leu Gln His Met Leu Ser Pro Gln Ile Thr
                965                 970                 975
Ile Gly Pro Gln Arg Pro Ala Pro Ser Gly Pro Gly Gly Ser Gly
            980                 985                 990
Gly Gly Ser Gly Gly Gly Gly Gly Gln Pro Pro Leu Gln Arg
            995                 1000                1005
Gly Lys Ser Gln Gln Leu Thr Val Ser Ala Ala Gln Lys Pro Arg Pro
    1010                1015                1020
Ser Ser Gly Asn Leu Leu Gln Ser Pro Glu Pro Ser Tyr Gly Pro Ala
1025                1030                1035                1040
Arg Pro Arg Gln Gln Ser Leu Ser Lys Glu Gly Ser Ile Gly Gly Ser
            1045                1050                1055
Gly Gly Ser Gly Gly Gly Gly Gly Gly Leu Lys Pro Ser Ile Thr
            1060                1065                1070
Lys Gln His Ser Gln Thr Pro Ser Thr Leu Asn Pro Thr Met Pro Ala
            1075                1080                1085
Ser Glu Arg Thr Val Ala Trp Val Ser Asn Met Pro His Leu Ser Ala
            1090                1095                1100
Asp Ile Glu Ser Ala His Ile Glu Arg Glu Glu Tyr Lys Leu Lys Glu
1105                1110                1115                1120
Tyr Ser Lys Ser Met Asp Glu Ser Arg Leu Asp Arg Val Lys Glu Tyr
                1125                1130                1135
Glu Glu Glu Ile His Ser Leu Lys Glu Arg Leu His Met Ser Asn Arg
            1140                1145                1150
```

```
Lys Leu Glu Glu Tyr Glu Arg Arg Leu Leu Ser Gln Glu Glu Gln Thr
        1155                1160                1165

Ser Lys Ile Leu Met Gln Tyr Gln Ala Arg Leu Glu Gln Ser Glu Lys
        1170                1175                1180

Arg Leu Arg Gln Gln Gln Val Glu Lys Asp Ser Gln Ile Lys Ser Ile
1185                1190                1195                1200

Ile Gly Arg Leu Met Leu Val Glu Glu Leu Arg Arg Asp His Pro
        1205                1210                1215

Ala Met Ala Glu Pro Leu Pro Glu Pro Lys Lys Arg Leu Leu Asp Ala
        1220                1225                1230

Gln Arg Gly Ser Phe Pro Pro Trp Val Gln Gln Thr Arg Val Arg Trp
        1235                1240                1245

Pro His Leu Gly Thr Ala Trp Pro Pro Gln Pro His Pro Pro His Pro
        1250                1255                1260

Gly Cys Arg Ser Gln Arg Thr Ala Ser Ser Gly Thr Pro Gln Thr Thr
1265                1270                1275                1280

Ser Pro Pro Ser Ile Thr Asp Leu Leu Pro Cys Ala Pro Tyr Pro Gly
        1285                1290                1295

Pro Pro Ser Val Thr Asp Leu Leu Pro Ser Ala Pro Asp Pro Gly Thr
        1300                1305                1310

Ser Pro Thr Thr Arg Thr Gly Arg His Gln Gly Thr Ala Gly Leu Ser
        1315                1320                1325

Pro Leu Thr Pro Pro Trp Gly Thr His Leu Ser Thr Pro Leu Leu His
        1330                1335                1340

Ser Arg Arg Glu Ser Gly Thr Leu Ser Cys Pro Leu Thr Pro Gly His
1345                1350                1355                1360

His Leu Pro His Thr Asp Pro Phe Thr Leu Gly Cys Tyr Pro His Pro
        1365                1370                1375

<210> SEQ ID NO 5
<211> LENGTH: 3981
<212> TYPE: DNA
<213> ORGANISM: Unknown Organism
<220> FEATURE:
<223> OTHER INFORMATION: Description of Unknown Organism: mammalian
      SYNGAP-C
<220> FEATURE:
<221> NAME/KEY: CDS
<222> LOCATION: (4)..(3588)
<220> FEATURE:
<221> NAME/KEY: CDS
<222> LOCATION: (3592)..(3981)

<400> SEQUENCE: 5 tag gga gag act gag ctg ccc caa gca ccc cat ttc cca ttt gct ccc      48
    Gly Glu Thr Glu Leu Pro Gln Ala Pro His Phe Pro Phe Ala Pro
    1               5                   10                  15 cag caa ggc ttc ctg agc cgg agg cta aaa agc tcc atc aaa cgt aca      96
Gln Gln Gly Phe Leu Ser Arg Arg Leu Lys Ser Ser Ile Lys Arg Thr
            20                  25                  30 aag tca caa ccc aaa ctt gac cgg acc agc agc ttt cga cag atc ctg    144
Lys Ser Gln Pro Lys Leu Asp Arg Thr Ser Ser Phe Arg Gln Ile Leu
        35                  40                  45 cct cgc ttc cga agt gct gac cat gac cgg gcc cgg ctg atg cag agc    192
Pro Arg Phe Arg Ser Ala Asp His Asp Arg Ala Arg Leu Met Gln Ser
    50                  55                  60 ttc aag gag tct cac tcc cat gag tcc ctg ctg agt ccc agc agt gct    240
Phe Lys Glu Ser His Ser His Glu Ser Leu Leu Ser Pro Ser Ser Ala
65                  70                  75
```

```
                                                            -continued gct gag gcc ctg gag ctc aac ctg gat gaa gac tcc att atc aag cca    288
Ala Glu Ala Leu Glu Leu Asn Leu Asp Glu Asp Ser Ile Ile Lys Pro
80              85                  90                  95 gta cac agc tcc atc ctg ggc cag gag ttc tgc ttt gag gta aca aca    336
Val His Ser Ser Ile Leu Gly Gln Glu Phe Cys Phe Glu Val Thr Thr
                100                 105                 110 tcg tct ggg aca aaa tgt ttt gcc tgt cgg tct gca gcc gaa agg gac    384
Ser Ser Gly Thr Lys Cys Phe Ala Cys Arg Ser Ala Ala Glu Arg Asp
            115                 120                 125 aaa tgg att gag aat cta cag agg gct gtg aaa ccc aac aag gac aac    432
Lys Trp Ile Glu Asn Leu Gln Arg Ala Val Lys Pro Asn Lys Asp Asn
        130                 135                 140 agc cgc cgg gta gat aac gtg ctg aaa cta tgg atc ata gaa gct cga    480
Ser Arg Arg Val Asp Asn Val Leu Lys Leu Trp Ile Ile Glu Ala Arg
    145                 150                 155 gag ctg ccc ccc aag aag cga tat tac tgc gag tta tgc ctg gac gac    528
Glu Leu Pro Pro Lys Lys Arg Tyr Tyr Cys Glu Leu Cys Leu Asp Asp
160                 165                 170                 175 atg ctc tat gca cgg acc act tcc aag ccc cgc tca gcc tca gga gac    576
Met Leu Tyr Ala Arg Thr Thr Ser Lys Pro Arg Ser Ala Ser Gly Asp
            180                 185                 190 act gtc ttt tgg ggc gag cac ttc gag ttt aac aac ctg cct gct gtc    624
Thr Val Phe Trp Gly Glu His Phe Glu Phe Asn Asn Leu Pro Ala Val
        195                 200                 205 cgg gcg ctg cgg ctg cat ctg tac cgt gac tcg gac aaa aag cgg aag    672
Arg Ala Leu Arg Leu His Leu Tyr Arg Asp Ser Asp Lys Lys Arg Lys
    210                 215                 220 aag gac aag gca ggc tac gtt ggc ctg gtg act gtt cca gtg gcc acc    720
Lys Asp Lys Ala Gly Tyr Val Gly Leu Val Thr Val Pro Val Ala Thr
225                 230                 235 ctg gct ggg cgc cac ttc aca gag cag tgg tac ccc gtg acc ctg cca    768
Leu Ala Gly Arg His Phe Thr Glu Gln Trp Tyr Pro Val Thr Leu Pro
240                 245                 250                 255 aca gga agt ggg ggc tct ggg ggt atg ggc tcg ggg gga gga ggg ggg    816
Thr Gly Ser Gly Gly Ser Gly Gly Met Gly Ser Gly Gly Gly Gly Gly
            260                 265                 270 tca ggg ggc ggc tca ggg ggc aaa ggg aaa gga ggc tgt cct gct gtg    864
Ser Gly Gly Gly Ser Gly Gly Lys Gly Lys Gly Gly Cys Pro Ala Val
        275                 280                 285 cgg ctg aag gcc cgt tac cag aca atg agt atc ctg ccc atg gag cta    912
Arg Leu Lys Ala Arg Tyr Gln Thr Met Ser Ile Leu Pro Met Glu Leu
    290                 295                 300 tat aag gag ttt gca gaa tat gtg acc aac cac tac cgc atg ctg tgt    960
Tyr Lys Glu Phe Ala Glu Tyr Val Thr Asn His Tyr Arg Met Leu Cys
305                 310                 315 gcc gtg ctg gag ccc gcc ctc aat gtc aag ggc aag gag gag gtc gct   1008
Ala Val Leu Glu Pro Ala Leu Asn Val Lys Gly Lys Glu Glu Val Ala
320                 325                 330                 335 agt gca ctg gtt cac atc ctg caa agc aca ggc aag gcc aag gac ttc   1056
Ser Ala Leu Val His Ile Leu Gln Ser Thr Gly Lys Ala Lys Asp Phe
            340                 345                 350 ctt tca gac atg gcc atg tca gag gta gac cgg ttc atg gag cgg gaa   1104
Leu Ser Asp Met Ala Met Ser Glu Val Asp Arg Phe Met Glu Arg Glu
        355                 360                 365 cac ctc ata ttc cgc gag aac acg ctc gcc act aaa gcc ata gaa gag   1152
His Leu Ile Phe Arg Glu Asn Thr Leu Ala Thr Lys Ala Ile Glu Glu
    370                 375                 380 tat atg aga ctg att ggc cag aaa tac ctc aag gat gcc att ggg gag   1200
Tyr Met Arg Leu Ile Gly Gln Lys Tyr Leu Lys Asp Ala Ile Gly Glu
```

```
         385                 390                 395
ttc atc cgg gct ctg tat gaa tct gag gag aac tgt gaa gta gac ccc     1248
Phe Ile Arg Ala Leu Tyr Glu Ser Glu Glu Asn Cys Glu Val Asp Pro
400                 405                 410                 415 atc aag tgc aca gcg tcc agt ctg gca gag cac cag gcc aac ctg cgg     1296
Ile Lys Cys Thr Ala Ser Ser Leu Ala Glu His Gln Ala Asn Leu Arg
                420                 425                 430 atg tgc tgt gag ttg gcc ctg tgc aag gtg gtc aac tcc cat tgc gtg     1344
Met Cys Cys Glu Leu Ala Leu Cys Lys Val Val Asn Ser His Cys Val
            435                 440                 445 ttc ccg agg gag ctg aag gag gtg ttt gca tca tgg cgg ctg cgc tgt     1392
Phe Pro Arg Glu Leu Lys Glu Val Phe Ala Ser Trp Arg Leu Arg Cys
        450                 455                 460 gca gag cgg ggc cgg gag gac att gct gac agg ctg atc agc gcc tcg     1440
Ala Glu Arg Gly Arg Glu Asp Ile Ala Asp Arg Leu Ile Ser Ala Ser
    465                 470                 475 ctc ttc ctg cgc ttc ctc tgc ccg gcc atc atg tcg ccc agt ctg ttt     1488
Leu Phe Leu Arg Phe Leu Cys Pro Ala Ile Met Ser Pro Ser Leu Phe
480                 485                 490                 495 gga ctg atg cag gag tac cca gat gag cag acc tca cga acc ctc acc     1536
Gly Leu Met Gln Glu Tyr Pro Asp Glu Gln Thr Ser Arg Thr Leu Thr
                500                 505                 510 ctc atc gcc aag gtt atc cag aac ctg gcc aac ttt tcc aag ttt acc     1584
Leu Ile Ala Lys Val Ile Gln Asn Leu Ala Asn Phe Ser Lys Phe Thr
            515                 520                 525 tca aag gag gac ttc ctg ggc ttc atg aac gag ttt ctg gag ctg gaa     1632
Ser Lys Glu Asp Phe Leu Gly Phe Met Asn Glu Phe Leu Glu Leu Glu
        530                 535                 540 tgg ggt tct atg cag caa ttc ttg tat gag ata tcc aac ctg gac aca     1680
Trp Gly Ser Met Gln Gln Phe Leu Tyr Glu Ile Ser Asn Leu Asp Thr
    545                 550                 555 ctg acc aac agc agc agt ttt gag ggc tac ata gac ttg ggc cgc gag     1728
Leu Thr Asn Ser Ser Ser Phe Glu Gly Tyr Ile Asp Leu Gly Arg Glu
560                 565                 570                 575 ctc tcc aca ctt cac gcc ctg ctc tgg gag gtg ctg ccc cag ctc agc     1776
Leu Ser Thr Leu His Ala Leu Leu Trp Glu Val Leu Pro Gln Leu Ser
                580                 585                 590 aag gaa gcc ctc ctg aag ctg ggc ccg ctg ccc cgg ctc ctc agc gac     1824
Lys Glu Ala Leu Leu Lys Leu Gly Pro Leu Pro Arg Leu Leu Ser Asp
            595                 600                 605 atc agc aca gcc ctg agg aac cct aac atc caa agg cag ccg agc cgc     1872
Ile Ser Thr Ala Leu Arg Asn Pro Asn Ile Gln Arg Gln Pro Ser Arg
        610                 615                 620 cag agc gag cgc gct cgg tct cag ccc atg gtg ctg cgc ggg ccg tca     1920
Gln Ser Glu Arg Ala Arg Ser Gln Pro Met Val Leu Arg Gly Pro Ser
    625                 630                 635 gcc gaa atg cag ggc tac atg atg cgg gac ctc aac agc tcc atc gac     1968
Ala Glu Met Gln Gly Tyr Met Met Arg Asp Leu Asn Ser Ser Ile Asp
640                 645                 650                 655 ctt cag tcc ttc atg gct cga ggc ctc aac agc tct atg gac atg gct     2016
Leu Gln Ser Phe Met Ala Arg Gly Leu Asn Ser Ser Met Asp Met Ala
                660                 665                 670 cgc ctc ccc tcc cca acc aag gag aaa ccc ccg ccg ccc cct ccc ggt     2064
Arg Leu Pro Ser Pro Thr Lys Glu Lys Pro Pro Pro Pro Pro Pro Gly
            675                 680                 685 ggg ggt aaa gac ctg ttc tat gtg agc cgg cca cca ctg gcc cgg tcc     2112
Gly Gly Lys Asp Leu Phe Tyr Val Ser Arg Pro Pro Leu Ala Arg Ser
        690                 695                 700 tcc cca gca tac tgc acg agc agc tcg gac atc aca gag ccg gag cag     2160
```

-continued

```
Ser Pro Ala Tyr Cys Thr Ser Ser Asp Ile Thr Glu Pro Glu Gln
    705                 710                 715 aag atg ctg agt gtc aac aag agt gtg tcc atg ctg gac ctg cag ggc        2208
Lys Met Leu Ser Val Asn Lys Ser Val Ser Met Leu Asp Leu Gln Gly
720                 725                 730                 735 gac ggg cct ggg ggc cgc ctt aac agc agt agt gtt tcc aac ctg gca        2256
Asp Gly Pro Gly Gly Arg Leu Asn Ser Ser Ser Val Ser Asn Leu Ala
                740                 745                 750 gct gtt ggg gac ctg ttg cac tca agc cag gct tca ctg aca gca gcc        2304
Ala Val Gly Asp Leu Leu His Ser Ser Gln Ala Ser Leu Thr Ala Ala
            755                 760                 765 ttg ggg ttg cgg cct gca cct gcc ggg cgc ctc tcc caa ggg agt ggc        2352
Leu Gly Leu Arg Pro Ala Pro Ala Gly Arg Leu Ser Gln Gly Ser Gly
        770                 775                 780 tct tcc atc aca gca gcc ggc atg cgc ctc agc cag atg ggt gtc act        2400
Ser Ser Ile Thr Ala Ala Gly Met Arg Leu Ser Gln Met Gly Val Thr
785                 790                 795 acg gat ggt gtc ccc gcc cag caa ctg cgc atc cct ctt tcc ttc cag        2448
Thr Asp Gly Val Pro Ala Gln Gln Leu Arg Ile Pro Leu Ser Phe Gln
800                 805                 810                 815 aac cct ctc ttc cat atg gct gcc gat gga cca ggg ccc cca gca ggc        2496
Asn Pro Leu Phe His Met Ala Ala Asp Gly Pro Gly Pro Pro Ala Gly
                820                 825                 830 cat gga ggg agc agt ggc cat ggt cca cct tcc tcc cat cac cac cac        2544
His Gly Gly Ser Ser Gly His Gly Pro Pro Ser Ser His His His His
            835                 840                 845 cac cac cat cac cat cac cga ggg gga gaa ccc cca ggg gac act ttt        2592
His His His His His His Arg Gly Gly Glu Pro Pro Gly Asp Thr Phe
        850                 855                 860 gcc ccg ttc cat ggc tat agc aag agc gag gac ctc tct aca ggg gtc        2640
Ala Pro Phe His Gly Tyr Ser Lys Ser Glu Asp Leu Ser Thr Gly Val
865                 870                 875 cct aag ccc cct gcg gcc tcc atc ctt cac agc cac agc tac agt gat        2688
Pro Lys Pro Pro Ala Ala Ser Ile Leu His Ser His Ser Tyr Ser Asp
880                 885                 890                 895 gag ttt gga ccc tct ggt act gat ttt acc cgt cgg cag ctc tca ctt        2736
Glu Phe Gly Pro Ser Gly Thr Asp Phe Thr Arg Arg Gln Leu Ser Leu
                900                 905                 910 cag gac aac cta cag cac atg ctc tcc ccg ccc cag atc acc atc ggt        2784
Gln Asp Asn Leu Gln His Met Leu Ser Pro Pro Gln Ile Thr Ile Gly
            915                 920                 925 ccc cag agg cca gct ccc tca ggg cca gga ggg ggc agt ggt ggg ggc        2832
Pro Gln Arg Pro Ala Pro Ser Gly Pro Gly Gly Gly Ser Gly Gly Gly
        930                 935                 940 agt ggt ggg ggc ggt ggg ggc cag cca cct ccc ttg cag agg ggc aaa        2880
Ser Gly Gly Gly Gly Gly Gln Pro Pro Pro Leu Gln Arg Gly Lys
945                 950                 955 tct cag cag ttg aca gtg agt gct gcc cag aaa ccc cgg ccg tcc agc        2928
Ser Gln Gln Leu Thr Val Ser Ala Ala Gln Lys Pro Arg Pro Ser Ser
960                 965                 970                 975 ggg aac cta ttg cag tcc ccg gaa cca agt tat ggt cct gcc cgt cca        2976
Gly Asn Leu Leu Gln Ser Pro Glu Pro Ser Tyr Gly Pro Ala Arg Pro
                980                 985                 990 cgg caa cag agc ctc agc aaa gag ggc agc att ggg ggc agc ggg ggc        3024
Arg Gln Gln Ser Leu Ser Lys Glu Gly Ser Ile Gly Gly Ser Gly Gly
            995                 1000                1005 agc ggt ggc gga ggg ggt ggg ggg ctc aag ccc tcc atc acc aag cag        3072
Ser Gly Gly Gly Gly Gly Gly Leu Lys Pro Ser Ile Thr Lys Gln
        1010                1015                1020
```

```
cat tcc cag act cca tcc acg ctg aac ccc acg atg ccg gcc tcg gag    3120
His Ser Gln Thr Pro Ser Thr Leu Asn Pro Thr Met Pro Ala Ser Glu
    1025                1030                1035 cgg act gta gcc tgg gtg tcc aat atg cct cac ctg tcc gct gac atc    3168
Arg Thr Val Ala Trp Val Ser Asn Met Pro His Leu Ser Ala Asp Ile
1040                1045                1050                1055 gag agt gca cac att gag cgg gaa gag tac aag ctg aag gag tac tcg    3216
Glu Ser Ala His Ile Glu Arg Glu Glu Tyr Lys Leu Lys Glu Tyr Ser
                1060                1065                1070 aag tcc atg gac gag agc cga ctg gac agg gtg aag gag tac gag gag    3264
Lys Ser Met Asp Glu Ser Arg Leu Asp Arg Val Lys Glu Tyr Glu Glu
            1075                1080                1085 gag atc cac tca ctg aag gaa agg cta cac atg tcc aac cgg aag ctg    3312
Glu Ile His Ser Leu Lys Glu Arg Leu His Met Ser Asn Arg Lys Leu
        1090                1095                1100 gaa gag tac gag cgg agg ctg ctg tcc cag gaa gag cag acc agc aag    3360
Glu Glu Tyr Glu Arg Arg Leu Leu Ser Gln Glu Glu Gln Thr Ser Lys
    1105                1110                1115 atc ctg atg cag tac caa gcc cgc ctg gag cag agc gag aag cgc ttg    3408
Ile Leu Met Gln Tyr Gln Ala Arg Leu Glu Gln Ser Glu Lys Arg Leu
1120                1125                1130                1135 agg cag cag cag gtg gag aag gac tcc cag atc aag agc atc att ggc    3456
Arg Gln Gln Gln Val Glu Lys Asp Ser Gln Ile Lys Ser Ile Ile Gly
                1140                1145                1150 agg ctg atg ctg gtg gag gag gag ctg cgc cgg gac cac ccc gcc atg    3504
Arg Leu Met Leu Val Glu Glu Glu Leu Arg Arg Asp His Pro Ala Met
            1155                1160                1165 gct gag ccg ctg cct gaa ccc aag aag agg ctc ctc gac gct cag aga    3552
Ala Glu Pro Leu Pro Glu Pro Lys Lys Arg Leu Leu Asp Ala Gln Arg
        1170                1175                1180 ggc agc ttc ccc cct tgg gtc caa caa acc cgc gtg tga cgc tgg ccc    3600
Gly Ser Phe Pro Pro Trp Val Gln Gln Thr Arg Val     Arg Trp Pro
    1185                1190                1195 cac ctt gga acg gcc tgg ccc ccc cag ccc cac ccc ccc cac ccc ggc    3648
His Leu Gly Thr Ala Trp Pro Pro Gln Pro His Pro Pro His Pro Gly
1200                1205                1210 tgc aga tca cag aga acg gcg agt tcc gga aca ccg cag acc act agc    3696
Cys Arg Ser Gln Arg Thr Ala Ser Ser Gly Thr Pro Gln Thr Thr Ser
1215                1220                1225                1230 cca ccc agc atc aca gac ctc ctt ccc tgt gca ccc tac ccc ggc cca    3744
Pro Pro Ser Ile Thr Asp Leu Leu Pro Cys Ala Pro Tyr Pro Gly Pro
                1235                1240                1245 ccc agc gtc aca gac ctc ctt ccc agt gca ccc gac cct gga aca tca    3792
Pro Ser Val Thr Asp Leu Leu Pro Ser Ala Pro Asp Pro Gly Thr Ser
            1250                1255                1260 cca acc acc agg act gga cgt cac caa ggg aca gcg gga ttg tct ccc    3840
Pro Thr Thr Arg Thr Gly Arg His Gln Gly Thr Ala Gly Leu Ser Pro
        1265                1270                1275 tta acg cct cct tgg ggc acc cat ctg tca acc cca ctg ctc cat tcc    3888
Leu Thr Pro Pro Trp Gly Thr His Leu Ser Thr Pro Leu Leu His Ser
    1280                1285                1290 agg agg gag agt ggg acc ctc agc tgc cct ctc acc cca gga cac cac    3936
Arg Arg Glu Ser Gly Thr Leu Ser Cys Pro Leu Thr Pro Gly His His
1295                1300                1305                1310 cta ccc cac aca gac ccc ttc act ctg ggg tgc tat ccc cat cct        3981
Leu Pro His Thr Asp Pro Phe Thr Leu Gly Cys Tyr Pro His Pro
                1315                1320                1325

<210> SEQ ID NO 6
<211> LENGTH: 1325
```

```
<212> TYPE: PRT
<213> ORGANISM: Unknown Organism
<220> FEATURE:
<223> OTHER INFORMATION: Description of Unknown Organism: mammalian
      SYNGAP-C

<400> SEQUENCE: 6
```

| | | | | | | | | | | | | | | |
|---|---|---|---|---|---|---|---|---|---|---|---|---|---|---|
| Gly | Glu | Thr | Glu | Leu | Pro | Gln | Ala | Pro | His | Phe | Pro | Phe | Ala | Pro | Gln |
| 1 | | | | 5 | | | | | 10 | | | | | 15 | |

| | | | | | | | | | | | | | | |
|---|---|---|---|---|---|---|---|---|---|---|---|---|---|---|
| Gln | Gly | Phe | Leu | Ser | Arg | Arg | Leu | Lys | Ser | Ser | Ile | Lys | Arg | Thr | Lys |
| | | | 20 | | | | | 25 | | | | | 30 | | |

| Ser | Gln | Pro | Lys | Leu | Asp | Arg | Thr | Ser | Ser | Phe | Arg | Gln | Ile | Leu | Pro |
|---|---|---|---|---|---|---|---|---|---|---|---|---|---|---|---|
| | | 35 | | | | | 40 | | | | | 45 | | | |

| Arg | Phe | Arg | Ser | Ala | Asp | His | Asp | Arg | Ala | Arg | Leu | Met | Gln | Ser | Phe |
|---|---|---|---|---|---|---|---|---|---|---|---|---|---|---|---|
| | 50 | | | | | 55 | | | | | 60 | | | | |

| Lys | Glu | Ser | His | Ser | His | Glu | Ser | Leu | Leu | Ser | Pro | Ser | Ser | Ala | Ala |
|---|---|---|---|---|---|---|---|---|---|---|---|---|---|---|---|
| 65 | | | | | 70 | | | | | 75 | | | | | 80 |

| Glu | Ala | Leu | Glu | Leu | Asn | Leu | Asp | Glu | Asp | Ser | Ile | Ile | Lys | Pro | Val |
|---|---|---|---|---|---|---|---|---|---|---|---|---|---|---|---|
| | | | | 85 | | | | | 90 | | | | | 95 | |

| His | Ser | Ser | Ile | Leu | Gly | Gln | Glu | Phe | Cys | Phe | Glu | Val | Thr | Thr | Ser |
|---|---|---|---|---|---|---|---|---|---|---|---|---|---|---|---|
| | | | 100 | | | | | 105 | | | | | 110 | | |

| Ser | Gly | Thr | Lys | Cys | Phe | Ala | Cys | Arg | Ser | Ala | Ala | Glu | Arg | Asp | Lys |
|---|---|---|---|---|---|---|---|---|---|---|---|---|---|---|---|
| | | 115 | | | | | 120 | | | | | 125 | | | |

| Trp | Ile | Glu | Asn | Leu | Gln | Arg | Ala | Val | Lys | Pro | Asn | Lys | Asp | Asn | Ser |
|---|---|---|---|---|---|---|---|---|---|---|---|---|---|---|---|
| | 130 | | | | | 135 | | | | | 140 | | | | |

| Arg | Arg | Val | Asp | Asn | Val | Leu | Lys | Leu | Trp | Ile | Ile | Glu | Ala | Arg | Glu |
|---|---|---|---|---|---|---|---|---|---|---|---|---|---|---|---|
| 145 | | | | | 150 | | | | | 155 | | | | | 160 |

| Leu | Pro | Pro | Lys | Lys | Arg | Tyr | Tyr | Cys | Glu | Leu | Cys | Leu | Asp | Asp | Met |
|---|---|---|---|---|---|---|---|---|---|---|---|---|---|---|---|
| | | | | 165 | | | | | 170 | | | | | 175 | |

| Leu | Tyr | Ala | Arg | Thr | Thr | Ser | Lys | Pro | Arg | Ser | Ala | Ser | Gly | Asp | Thr |
|---|---|---|---|---|---|---|---|---|---|---|---|---|---|---|---|
| | | | 180 | | | | | 185 | | | | | 190 | | |

| Val | Phe | Trp | Gly | Glu | His | Phe | Glu | Phe | Asn | Asn | Leu | Pro | Ala | Val | Arg |
|---|---|---|---|---|---|---|---|---|---|---|---|---|---|---|---|
| | | 195 | | | | | 200 | | | | | 205 | | | |

| Ala | Leu | Arg | Leu | His | Leu | Tyr | Arg | Asp | Ser | Asp | Lys | Lys | Arg | Lys | Lys |
|---|---|---|---|---|---|---|---|---|---|---|---|---|---|---|---|
| | 210 | | | | | 215 | | | | | 220 | | | | |

| Asp | Lys | Ala | Gly | Tyr | Val | Gly | Leu | Val | Thr | Val | Pro | Val | Ala | Thr | Leu |
|---|---|---|---|---|---|---|---|---|---|---|---|---|---|---|---|
| 225 | | | | | 230 | | | | | 235 | | | | | 240 |

| Ala | Gly | Arg | His | Phe | Thr | Glu | Gln | Trp | Tyr | Pro | Val | Thr | Leu | Pro | Thr |
|---|---|---|---|---|---|---|---|---|---|---|---|---|---|---|---|
| | | | | 245 | | | | | 250 | | | | | 255 | |

| Gly | Ser | Gly | Gly | Ser | Gly | Gly | Met | Gly | Ser | Gly | Gly | Gly | Gly | Gly | Ser |
|---|---|---|---|---|---|---|---|---|---|---|---|---|---|---|---|
| | | | 260 | | | | | 265 | | | | | 270 | | |

| Gly | Gly | Gly | Ser | Gly | Gly | Lys | Gly | Lys | Gly | Gly | Cys | Pro | Ala | Val | Arg |
|---|---|---|---|---|---|---|---|---|---|---|---|---|---|---|---|
| | | 275 | | | | | 280 | | | | | 285 | | | |

| Leu | Lys | Ala | Arg | Tyr | Gln | Thr | Met | Ser | Ile | Leu | Pro | Met | Glu | Leu | Tyr |
|---|---|---|---|---|---|---|---|---|---|---|---|---|---|---|---|
| | 290 | | | | | 295 | | | | | 300 | | | | |

| Lys | Glu | Phe | Ala | Glu | Tyr | Val | Thr | Asn | His | Tyr | Arg | Met | Leu | Cys | Ala |
|---|---|---|---|---|---|---|---|---|---|---|---|---|---|---|---|
| 305 | | | | | 310 | | | | | 315 | | | | | 320 |

| Val | Leu | Glu | Pro | Ala | Leu | Asn | Val | Lys | Gly | Lys | Glu | Glu | Val | Ala | Ser |
|---|---|---|---|---|---|---|---|---|---|---|---|---|---|---|---|
| | | | | 325 | | | | | 330 | | | | | 335 | |

| Ala | Leu | Val | His | Ile | Leu | Gln | Ser | Thr | Gly | Lys | Ala | Lys | Asp | Phe | Leu |
|---|---|---|---|---|---|---|---|---|---|---|---|---|---|---|---|
| | | | 340 | | | | | 345 | | | | | 350 | | |

| Ser | Asp | Met | Ala | Met | Ser | Glu | Val | Asp | Arg | Phe | Met | Glu | Arg | Glu | His |
|---|---|---|---|---|---|---|---|---|---|---|---|---|---|---|---|
| | | 355 | | | | | 360 | | | | | 365 | | | |

| Leu | Ile | Phe | Arg | Glu | Asn | Thr | Leu | Ala | Thr | Lys | Ala | Ile | Glu | Glu | Tyr |
|---|---|---|---|---|---|---|---|---|---|---|---|---|---|---|---|
| | 370 | | | | | 375 | | | | | 380 | | | | |

-continued

```
Met Arg Leu Ile Gly Gln Lys Tyr Leu Lys Asp Ala Ile Gly Glu Phe
385                 390                 395                 400
Ile Arg Ala Leu Tyr Glu Ser Glu Asn Cys Glu Val Asp Pro Ile
            405                 410                 415
Lys Cys Thr Ala Ser Ser Leu Ala Glu His Gln Ala Asn Leu Arg Met
            420                 425                 430
Cys Cys Glu Leu Ala Leu Cys Lys Val Val Asn Ser His Cys Val Phe
            435                 440                 445
Pro Arg Glu Leu Lys Glu Val Phe Ala Ser Trp Arg Leu Arg Cys Ala
    450                 455                 460
Glu Arg Gly Arg Glu Asp Ile Ala Asp Arg Leu Ile Ser Ala Ser Leu
465                 470                 475                 480
Phe Leu Arg Phe Leu Cys Pro Ala Ile Met Ser Pro Ser Leu Phe Gly
                485                 490                 495
Leu Met Gln Glu Tyr Pro Asp Glu Gln Thr Ser Arg Thr Leu Thr Leu
            500                 505                 510
Ile Ala Lys Val Ile Gln Asn Leu Ala Asn Phe Ser Lys Phe Thr Ser
            515                 520                 525
Lys Glu Asp Phe Leu Gly Phe Met Asn Glu Phe Leu Glu Leu Glu Trp
    530                 535                 540
Gly Ser Met Gln Gln Phe Leu Tyr Glu Ile Ser Asn Leu Asp Thr Leu
545                 550                 555                 560
Thr Asn Ser Ser Ser Phe Glu Gly Tyr Ile Asp Leu Gly Arg Glu Leu
                565                 570                 575
Ser Thr Leu His Ala Leu Leu Trp Glu Val Leu Pro Gln Leu Ser Lys
            580                 585                 590
Glu Ala Leu Leu Lys Leu Gly Pro Leu Pro Arg Leu Leu Ser Asp Ile
    595                 600                 605
Ser Thr Ala Leu Arg Asn Pro Asn Ile Gln Arg Gln Pro Ser Arg Gln
            610                 615                 620
Ser Glu Arg Ala Arg Ser Gln Pro Met Val Leu Arg Gly Pro Ser Ala
625                 630                 635                 640
Glu Met Gln Gly Tyr Met Met Arg Asp Leu Asn Ser Ser Ile Asp Leu
                645                 650                 655
Gln Ser Phe Met Ala Arg Gly Leu Asn Ser Ser Met Asp Met Ala Arg
            660                 665                 670
Leu Pro Ser Pro Thr Lys Glu Lys Pro Pro Pro Pro Pro Gly Gly
            675                 680                 685
Gly Lys Asp Leu Phe Tyr Val Ser Arg Pro Pro Leu Ala Arg Ser Ser
    690                 695                 700
Pro Ala Tyr Cys Thr Ser Ser Ser Asp Ile Thr Glu Pro Glu Gln Lys
705                 710                 715                 720
Met Leu Ser Val Asn Lys Ser Val Ser Met Leu Asp Leu Gln Gly Asp
                725                 730                 735
Gly Pro Gly Gly Arg Leu Asn Ser Ser Ser Val Ser Asn Leu Ala Ala
            740                 745                 750
Val Gly Asp Leu Leu His Ser Ser Gln Ala Ser Leu Thr Ala Ala Leu
            755                 760                 765
Gly Leu Arg Pro Ala Pro Ala Gly Arg Leu Ser Gln Gly Ser Gly Ser
    770                 775                 780
Ser Ile Thr Ala Ala Gly Met Arg Leu Ser Gln Met Gly Val Thr Thr
785                 790                 795                 800
```

-continued

```
Asp Gly Val Pro Ala Gln Gln Leu Arg Ile Pro Leu Ser Phe Gln Asn
                805                 810                 815

Pro Leu Phe His Met Ala Ala Asp Gly Pro Pro Ala Gly His
        820                 825                 830

Gly Gly Ser Ser Gly His Gly Pro Ser Ser His His His His
        835                 840                 845

His His His His His Arg Gly Gly Glu Pro Pro Gly Asp Thr Phe Ala
    850                 855                 860

Pro Phe His Gly Tyr Ser Lys Ser Glu Asp Leu Ser Thr Gly Val Pro
865                 870                 875                 880

Lys Pro Pro Ala Ala Ser Ile Leu His Ser His Ser Tyr Ser Asp Glu
                885                 890                 895

Phe Gly Pro Ser Gly Thr Asp Phe Thr Arg Arg Gln Leu Ser Leu Gln
                900                 905                 910

Asp Asn Leu Gln His Met Leu Ser Pro Pro Gln Ile Thr Ile Gly Pro
            915                 920                 925

Gln Arg Pro Ala Pro Ser Gly Pro Gly Gly Ser Gly Gly Gly Ser
        930                 935                 940

Gly Gly Gly Gly Gly Gly Gln Pro Pro Leu Gln Arg Gly Lys Ser
945                 950                 955                 960

Gln Gln Leu Thr Val Ser Ala Ala Gln Lys Pro Arg Pro Ser Ser Gly
                965                 970                 975

Asn Leu Leu Gln Ser Pro Glu Pro Ser Tyr Gly Pro Ala Arg Pro Arg
            980                 985                 990

Gln Gln Ser Leu Ser Lys Glu Gly Ser Ile Gly Gly Ser Gly Ser
        995                 1000                1005

Gly Gly Gly Gly Gly Gly Leu Lys Pro Ser Ile Thr Lys Gln His
    1010                1015                1020

Ser Gln Thr Pro Ser Thr Leu Asn Pro Thr Met Pro Ala Ser Glu Arg
1025                1030                1035                1040

Thr Val Ala Trp Val Ser Asn Met Pro His Leu Ser Ala Asp Ile Glu
                1045                1050                1055

Ser Ala His Ile Glu Arg Glu Tyr Lys Leu Lys Glu Tyr Ser Lys
            1060                1065                1070

Ser Met Asp Glu Ser Arg Leu Asp Arg Val Lys Glu Tyr Glu Glu
        1075                1080                1085

Ile His Ser Leu Lys Glu Arg Leu His Met Ser Asn Arg Lys Leu Glu
    1090                1095                1100

Glu Tyr Glu Arg Arg Leu Leu Ser Gln Glu Glu Gln Thr Ser Lys Ile
1105                1110                1115                1120

Leu Met Gln Tyr Gln Ala Arg Leu Glu Gln Ser Glu Lys Arg Leu Arg
                1125                1130                1135

Gln Gln Gln Val Glu Lys Asp Ser Gln Ile Lys Ser Ile Ile Gly Arg
            1140                1145                1150

Leu Met Leu Val Glu Glu Glu Leu Arg Arg Asp His Pro Ala Met Ala
        1155                1160                1165

Glu Pro Leu Pro Glu Pro Lys Lys Arg Leu Leu Asp Ala Gln Arg Gly
    1170                1175                1180

Ser Phe Pro Pro Trp Val Gln Gln Thr Arg Val Arg Trp Pro His Leu
1185                1190                1195                1200

Gly Thr Ala Trp Pro Pro Gln Pro His Pro His Pro Gly Cys Arg
                1205                1210                1215

Ser Gln Arg Thr Ala Ser Ser Gly Thr Pro Gln Thr Thr Ser Pro Pro
```

```
                    1220              1225              1230
Ser Ile Thr Asp Leu Leu Pro Cys Ala Pro Tyr Pro Gly Pro Pro Ser
        1235                  1240              1245

Val Thr Asp Leu Leu Pro Ser Ala Pro Asp Pro Gly Thr Ser Pro Thr
    1250                  1255              1260

Thr Arg Thr Gly Arg His Gln Gly Thr Ala Gly Leu Ser Pro Leu Thr
1265              1270              1275              1280

Pro Pro Trp Gly Thr His Leu Ser Thr Pro Leu Leu His Ser Arg Arg
                1285              1290              1295

Glu Ser Gly Thr Leu Ser Cys Pro Leu Thr Pro Gly His His Leu Pro
                1300              1305              1310

His Thr Asp Pro Phe Thr Leu Gly Cys Tyr Pro His Pro
            1315              1320              1325

<210> SEQ ID NO 7
<211> LENGTH: 216
<212> TYPE: PRT
<213> ORGANISM: Unknown Organism
<220> FEATURE:
<223> OTHER INFORMATION: Description of Unknown Organism: mammalian
      SYNGAP-C

<400> SEQUENCE: 7

Gly Lys Ala Lys Asp Phe Leu Ser Asp Met Ala Met Ser Glu Val Asp
 1               5                  10                  15

Arg Phe Met Glu Arg Glu His Leu Ile Phe Arg Glu Asn Thr Leu Ala
                20                  25                  30

Thr Lys Ala Ile Glu Glu Tyr Met Arg Leu Ile Gly Gln Lys Tyr Leu
            35                  40                  45

Lys Asp Ala Ile Gly Glu Phe Ile Arg Ala Leu Tyr Glu Ser Glu Glu
 50                  55                  60

Asn Cys Glu Val Asp Pro Ile Lys Cys Thr Ala Ser Ser Leu Ala Glu
 65                  70                  75                  80

His Gln Ala Asn Leu Arg Met Cys Cys Glu Leu Ala Leu Cys Lys Val
                85                  90                  95

Val Asn Ser His Cys Val Phe Pro Arg Glu Leu Lys Glu Val Phe Ala
            100                 105                 110

Ser Trp Arg Leu Arg Cys Ala Glu Arg Gly Arg Glu Asp Ile Ala Asp
        115                 120                 125

Arg Leu Ile Ser Ala Ser Leu Phe Leu Arg Phe Leu Cys Pro Ala Ile
    130                 135                 140

Met Ser Pro Ser Leu Phe Gly Leu Met Gln Glu Tyr Pro Asp Glu Gln
145                 150                 155                 160

Thr Ser Arg Thr Leu Thr Leu Ile Ala Lys Val Ile Gln Asn Leu Ala
                165                 170                 175

Asn Phe Ser Lys Phe Thr Ser Lys Glu Asp Phe Leu Gly Phe Met Asn
            180                 185                 190

Glu Phe Leu Glu Leu Glu Trp Gly Ser Met Gln Gln Phe Leu Tyr Glu
        195                 200                 205

Ile Ser Asn Leu Asp Thr Leu Thr
    210                 215

<210> SEQ ID NO 8
<211> LENGTH: 218
<212> TYPE: PRT
<213> ORGANISM: Rattus norvegicus
```

-continued

```
<400> SEQUENCE: 8

Lys Leu Glu Ser Leu Leu Cys Thr Leu Asn Asp Arg Glu Ile Ser
 1               5                  10                  15

Met Glu Asp Glu Ala Thr Thr Leu Phe Arg Ala Thr Thr Leu Ala Ser
                20                  25                  30

Thr Leu Met Glu Gln Tyr Met Lys Ala Thr Ala Thr Gln Phe Val His
            35                  40                  45

His Ala Leu Lys Asp Ser Ile Leu Lys Ile Met Glu Val Gln His Lys
        50                  55                  60

Trp Pro Thr Asn Asn Thr Met Arg Thr Arg Val Val Ser Gly Phe Val
 65                  70                  75                  80

Phe Leu Arg Leu Ile Cys Pro Ala Ile Leu Asn Pro Arg Met Phe Asn
                85                  90                  95

Ile Ile Ser Asp Ser Pro Ser Pro Ile Ala Ala Arg Thr Leu Thr Leu
               100                 105                 110

Val Ala Lys Ser Val Gln Asn Leu Ala Asn Ser Lys Gln Ser Cys Glu
            115                 120                 125

Leu Ser Pro Ser Lys Leu Glu Lys Asn Glu Asp Val Asn Thr Asn Leu
        130                 135                 140

Ala His Leu Leu Ser Ile Leu Ser Glu Leu Val Glu Lys Ile Phe Met
145                 150                 155                 160

Ala Ser Glu Ile Leu Pro Pro Thr Leu Arg Tyr Ile Tyr Gly Cys Leu
                165                 170                 175

Gln Lys Ser Leu Val Glu Phe Gly Ala Lys Glu Pro Tyr Met Glu Gly
            180                 185                 190

Val Asn Pro Phe Ile Lys Ser Asn Lys His Arg Met Ile Met Phe Leu
        195                 200                 205

Asp Glu Leu Gly Asn Val Pro Glu Leu Pro
    210                 215

<210> SEQ ID NO 9
<211> LENGTH: 219
<212> TYPE: PRT
<213> ORGANISM: Homo sapiens

<400> SEQUENCE: 9

His Leu Leu Tyr Gln Leu Leu Trp Asn Met Phe Ser Lys Glu Val Glu
 1               5                  10                  15

Leu Ala Asp Ser Met Gln Thr Leu Phe Arg Gly Asn Ser Leu Ala Ser
                20                  25                  30

Lys Ile Met Thr Phe Cys Phe Lys Val Tyr Gly Ala Thr Tyr Leu Gln
            35                  40                  45

Lys Leu Leu Asp Pro Leu Leu Arg Ile Val Ile Thr Ser Ser Asp Trp
        50                  55                  60

Gln His Val Ser Phe Glu Val Asp Pro Thr Arg Leu Glu Pro Ser Glu
 65                  70                  75                  80

Ser Leu Glu Glu Asn Gln Arg Asn Leu Leu Gln Met Thr Glu Lys Phe
                85                  90                  95

Phe His Ala Ile Ile Ser Ser Ser Glu Phe Pro Pro Gln Leu Arg
               100                 105                 110

Ser Val Cys His Cys Leu Tyr Gln Val Val Ser Gln Arg Phe Pro Gln
            115                 120                 125

Asn Ser Ile Gly Ala Val Gly Ser Ala Met Phe Leu Arg Phe Ile Asn
        130                 135                 140
```

```
Pro Ala Ile Val Ser Pro Tyr Glu Ala Gly Ile Leu Asp Lys Lys Pro
145                 150                 155                 160

Pro Pro Arg Ile Glu Arg Gly Leu Lys Leu Met Ser Lys Ile Leu Gln
            165                 170                 175

Ser Ile Ala Asn His Val Leu Phe Thr Lys Glu His Met Arg Pro
        180                 185                 190

Phe Asn Asp Phe Val Lys Ser Asn Phe Asp Ala Ala Arg Arg Phe Phe
            195                 200                 205

Leu Asp Ile Ala Ser Asp Cys Pro Thr Ser Asp
    210                 215
```

<210> SEQ ID NO 10
<211> LENGTH: 82
<212> TYPE: PRT
<213> ORGANISM: Unknown Organism
<220> FEATURE:
<223> OTHER INFORMATION: Description of Unknown Organism: mammalian
      SYNGAP-A

<400> SEQUENCE: 10

```
Phe Lys Glu Ser His Ser His Glu Ser Leu Leu Ser Pro Ser Ser Ala
1               5                   10                  15

Ala Glu Ala Leu Glu Leu Asn Leu Asp Glu Asp Ser Ile Lys Lys Pro
            20                  25                  30

Val His Ser Ser Ile Leu Gly Gln Glu Phe Cys Phe Glu Val Thr Thr
        35                  40                  45

Ser Ser Gly Thr Lys Cys Phe Ala Cys Arg Ser Ala Ala Glu Arg Asp
    50                  55                  60

Lys Trp Ile Glu Asn Leu Gln Arg Ala Val Lys Pro Asn Lys Asp Asn
65                  70                  75                  80

Ser Arg
```

<210> SEQ ID NO 11
<211> LENGTH: 114
<212> TYPE: PRT
<213> ORGANISM: Homo sapiens

<400> SEQUENCE: 11

```
Phe Tyr Lys Asn Ile Val Lys Lys Gly Tyr Leu Leu Lys Lys Gly Lys
1               5                   10                  15

Gly Lys Arg Trp Lys Asn Leu Tyr Phe Ile Leu Glu Gly Ser Asp Ala
            20                  25                  30

Gln Leu Ile Tyr Phe Glu Ser Glu Lys Arg Ala Thr Lys Pro Lys Gly
        35                  40                  45

Leu Ile Asp Leu Ser Val Cys Ser Val Tyr Val Val His Asp Ser Leu
    50                  55                  60

Phe Gly Arg Pro Asn Cys Phe Gln Ile Val Val Gln His Phe Ser Glu
65                  70                  75                  80

Glu His Tyr Ile Phe Tyr Phe Ala Gly Glu Thr Pro Glu Gln Ala Glu
                85                  90                  95

Asp Trp Met Lys Gly Leu Gln Ala Phe Cys Asn Leu Arg Lys Ser Ser
            100                 105                 110

Pro Gly
```

<210> SEQ ID NO 12
<211> LENGTH: 111
<212> TYPE: PRT
<213> ORGANISM: Drosphila melanogaster -continued

```
<400> SEQUENCE: 12

Pro Val Leu Leu Lys Glu Gly Glu Gly Leu Met Thr Lys Tyr Pro Thr
  1               5                  10                  15

Ser Arg Lys Arg Phe Gly Arg Gln Phe Lys Gln Arg His Phe Arg Leu
             20                  25                  30

Thr Thr His Ser Leu Ser Tyr Ala Lys Ser Lys Gly Lys Gln Pro Ile
         35                  40                  45

Cys Asp Ile Pro Leu Gln Glu Ile Ala Ser Val Glu Gln Leu Lys Asp
     50                  55                  60

Lys Ser Phe Lys Met Gln Asn Cys Phe Lys Ile Val His Asn Asp Arg
 65                  70                  75                  80

Ser Leu Ile Val Gln Thr Thr Asn Cys Val Glu Glu Arg Glu Trp Phe
                 85                  90                  95

Asp Leu Leu His Lys Ile Cys Leu Met Asn Ser Ile Arg Met Gln
             100                 105                 110

<210> SEQ ID NO 13
<211> LENGTH: 108
<212> TYPE: PRT
<213> ORGANISM: Homo sapiens

<400> SEQUENCE: 13

Met Glu Pro Lys Arg Ile Arg Glu Gly Tyr Leu Val Lys Lys Gly Ser
  1               5                  10                  15

Val Phe Asn Thr Trp Lys Pro Met Trp Val Val Leu Leu Glu Asp Gly
             20                  25                  30

Ile Glu Phe Tyr Lys Lys Lys Ser Asp Asn Ser Pro Lys Gly Met Ile
         35                  40                  45

Pro Leu Lys Gly Ser Thr Leu Thr Ser Pro Cys Gln Asp Phe Gly Lys
     50                  55                  60

Arg Met Phe Val Phe Lys Ile Thr Thr Thr Lys Gln Gln Asp His Phe
 65                  70                  75                  80

Phe Gln Ala Ala Phe Leu Glu Glu Arg Asp Ala Trp Val Arg Asp Ile
                 85                  90                  95

Asn Lys Ala Ile Lys Cys Ile Glu Gly Gly Gln Lys
             100                 105

<210> SEQ ID NO 14
<211> LENGTH: 110
<212> TYPE: PRT
<213> ORGANISM: Unknown Organism
<220> FEATURE:
<223> OTHER INFORMATION: Description of Unknown Organism: mammalian
      SYNGAP-A

<400> SEQUENCE: 14

Val Asp Asn Val Leu Lys Leu Trp Ile Ile Glu Ala Arg Glu Leu Pro
  1               5                  10                  15

Pro Lys Lys Arg Tyr Tyr Cys Glu Leu Cys Leu Asp Asp Met Leu Tyr
             20                  25                  30

Ala Arg Thr Thr Ser Lys Pro Arg Ser Ala Ser Gly Asp Thr Val Phe
         35                  40                  45

Trp Gly Glu His Phe Glu Phe Asn Asn Leu Pro Ala Val Arg Ala Leu
     50                  55                  60

Arg Leu His Leu Tyr Arg Asp Ser Asp Lys Arg Lys Lys Asp Lys
 65                  70                  75                  80
```

```
Ala Gly Tyr Val Gly Leu Val Thr Val Pro Val Ala Thr Leu Ala Gly
                85                  90                  95

Arg His Phe Thr Glu Gln Trp Tyr Pro Val Thr Leu Pro Thr
            100                 105                 110

<210> SEQ ID NO 15
<211> LENGTH: 107
<212> TYPE: PRT
<213> ORGANISM: Homo sapiens

<400> SEQUENCE: 15

Gln Val Ser Ser Leu Val Leu His Ile Glu Glu Ala His Lys Leu Pro
1               5                   10                  15

Val Lys His Phe Thr Asn Pro Tyr Cys Asn Ile Tyr Leu Asn Ser Val
            20                  25                  30

Gln Val Ala Lys Thr His Ala Arg Glu Gly Gln Asn Pro Val Trp Ser
        35                  40                  45

Glu Glu Phe Val Phe Asp Asp Leu Pro Pro Asp Ile Asn Arg Phe Glu
    50                  55                  60

Ile Thr Leu Ser Asn Lys Thr Lys Ser Lys Asp Pro Asp Ile Leu
65                  70                  75                  80

Phe Met Arg Cys Gln Leu Ser Arg Leu Gln Lys Gly His Ala Thr Asp
                85                  90                  95

Glu Trp Phe Leu Leu Ser Ser His Ile Pro Leu
            100                 105

<210> SEQ ID NO 16
<211> LENGTH: 116
<212> TYPE: PRT
<213> ORGANISM: Rattus norvegicus

<400> SEQUENCE: 16

Asp Tyr Asp Phe Gln Ala Asn Gln Leu Thr Val Gly Val Leu Gln Ala
1               5                   10                  15

Ala Glu Leu Pro Ala Leu Asp Met Gly Gly Thr Ser Asp Pro Tyr Val
            20                  25                  30

Lys Val Phe Leu Leu Pro Asp Lys Lys Lys Tyr Glu Thr Lys Val
        35                  40                  45

His Arg Lys Thr Leu Asn Pro Ala Phe Asn Glu Thr Phe Thr Phe Lys
    50                  55                  60

Val Pro Tyr Gln Glu Leu Gly Gly Lys Thr Leu Val Met Ala Ile Tyr
65                  70                  75                  80

Asp Phe Asp Arg Phe Ser Lys His Asp Ile Ile Gly Glu Val Lys Val
                85                  90                  95

Pro Met Asn Thr Val Asp Leu Gly Gln Pro Ile Glu Glu Trp Arg Asp
            100                 105                 110

Leu Gln Gly Gly
        115

<210> SEQ ID NO 17
<211> LENGTH: 132
<212> TYPE: PRT
<213> ORGANISM: Bos taurus

<400> SEQUENCE: 17

Leu Tyr Asp Gln Asp Asn Ser Ser Leu Lys Cys Thr Ile Ile Lys Ala
1               5                   10                  15

Lys Gly Leu Lys Pro Met Asp Ser Asn Gly Leu Ala Asp Pro Tyr Val
```

-continued

```
                    20                  25                  30
Lys Leu His Leu Pro Gly Ala Ser Lys Ser Asn Lys Leu Arg Thr
         35                  40                  45
Lys Thr Leu Arg Asn Thr Arg Asn Pro Ile Trp Asn Glu Thr Leu Val
 50                  55                  60
Tyr His Gly Ile Thr Asp Glu Asp Met Gln Arg Lys Thr Leu Arg Ile
 65                  70                  75                  80
Ser Val Cys Asp Glu Asp Lys Phe Gly His Asn Glu Phe Ile Gly Glu
                 85                  90                  95
Thr Arg Phe Ser Leu Lys Lys Leu Lys Pro Asn Gln Arg Lys Asn Phe
            100                 105                 110
Asn Ile Cys Leu Glu Arg Val Ile Pro Met Lys Arg Ala Gly Thr Thr
         115                 120                 125
Gly Ser Ala Arg
        130
```

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
acgcgtcgac cagagagccc cgcaag                                          26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
gaagatctag gtctatactg ggccac                                          26

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

```
Lys Arg Leu Leu Asp Ala Gln Arg Gly Ser Phe Pro Pro Trp Val Gln
 1               5                  10                  15
Gln Thr Arg Val
            20
```

<210> SEQ ID NO 21
<211> LENGTH: 1135
<212> TYPE: PRT
<213> ORGANISM: Unknown Organism
<220> FEATURE:
<223> OTHER INFORMATION: Description of Unknown Organism: mammalian SYNGAP-C

<400> SEQUENCE: 21

```
Met Gln Ser Phe Lys Glu Ser His Ser His Glu Ser Leu Leu Ser Pro
 1               5                  10                  15
```

-continued

```
Ser Ser Ala Ala Glu Ala Leu Glu Leu Asn Leu Asp Glu Asp Ser Ile
         20                  25                  30
Ile Lys Pro Val His Ser Ser Ile Leu Gly Gln Glu Phe Cys Phe Glu
         35                  40                  45
Val Thr Thr Ser Ser Gly Thr Lys Cys Phe Ala Cys Arg Ser Ala Ala
         50                  55                  60
Glu Arg Asp Lys Trp Ile Glu Asn Leu Gln Arg Ala Val Lys Pro Asn
 65                  70                  75                  80
Lys Asp Asn Ser Arg Arg Val Asp Asn Val Leu Lys Leu Trp Ile Ile
                 85                  90                  95
Glu Ala Arg Glu Leu Pro Pro Lys Lys Arg Tyr Tyr Cys Glu Leu Cys
                100                 105                 110
Leu Asp Asp Met Leu Tyr Ala Arg Thr Thr Ser Lys Pro Arg Ser Ala
                115                 120                 125
Ser Gly Asp Thr Val Phe Trp Gly His Phe Glu Phe Asn Asn Leu
                130                 135                 140
Pro Ala Val Arg Ala Leu Arg Leu His Leu Tyr Arg Asp Ser Asp Lys
145                 150                 155                 160
Lys Arg Lys Lys Asp Lys Ala Gly Tyr Val Gly Leu Val Thr Val Pro
                165                 170                 175
Val Ala Thr Leu Ala Gly Arg His Phe Thr Glu Gln Trp Tyr Pro Val
                180                 185                 190
Thr Leu Pro Thr Gly Ser Gly Gly Ser Gly Gly Met Gly Ser Gly Gly
                195                 200                 205
Gly Gly Gly Ser Gly Gly Gly Ser Gly Gly Lys Gly Lys Gly Gly Cys
            210                 215                 220
Pro Ala Val Arg Leu Lys Ala Arg Tyr Gln Thr Met Ser Ile Leu Pro
225                 230                 235                 240
Met Glu Leu Tyr Lys Glu Phe Ala Glu Tyr Val Thr Asn His Tyr Arg
                245                 250                 255
Met Leu Cys Ala Val Leu Glu Pro Ala Leu Asn Val Lys Gly Lys Glu
                260                 265                 270
Glu Val Ala Ser Ala Leu Val His Ile Leu Gln Ser Thr Gly Lys Ala
            275                 280                 285
Lys Asp Phe Leu Ser Asp Met Ala Met Ser Glu Val Asp Arg Phe Met
290                 295                 300
Glu Arg Glu His Leu Ile Phe Arg Glu Asn Thr Leu Ala Thr Lys Ala
305                 310                 315                 320
Ile Glu Glu Tyr Met Arg Leu Ile Gly Gln Lys Tyr Leu Lys Asp Ala
                325                 330                 335
Ile Gly Glu Phe Ile Arg Ala Leu Tyr Glu Ser Glu Glu Asn Cys Glu
                340                 345                 350
Val Asp Pro Ile Lys Cys Thr Ala Ser Ser Leu Ala Glu His Gln Ala
                355                 360                 365
Asn Leu Arg Met Cys Cys Glu Leu Ala Leu Cys Lys Val Val Asn Ser
                370                 375                 380
His Cys Val Phe Pro Arg Glu Leu Lys Glu Val Phe Ala Ser Trp Arg
385                 390                 395                 400
Leu Arg Cys Ala Glu Arg Gly Arg Glu Asp Ile Ala Asp Arg Leu Ile
                405                 410                 415
Ser Ala Ser Leu Phe Leu Arg Phe Leu Cys Pro Ala Ile Met Ser Pro
                420                 425                 430
```

-continued

```
Ser Leu Phe Gly Leu Met Gln Glu Tyr Pro Asp Glu Gln Thr Ser Arg
        435                 440                 445

Thr Leu Thr Leu Ile Ala Lys Val Ile Gln Asn Leu Ala Asn Phe Ser
    450                 455                 460

Lys Phe Thr Ser Lys Glu Asp Phe Leu Gly Phe Met Asn Glu Phe Leu
465                 470                 475                 480

Glu Leu Glu Trp Gly Ser Met Gln Gln Phe Leu Tyr Glu Ile Ser Asn
                485                 490                 495

Leu Asp Thr Leu Thr Asn Ser Ser Phe Glu Gly Tyr Ile Asp Leu
                500                 505                 510

Gly Arg Glu Leu Ser Thr Leu His Ala Leu Leu Trp Glu Val Leu Pro
            515                 520                 525

Gln Leu Ser Lys Glu Ala Leu Leu Lys Leu Gly Pro Leu Pro Arg Leu
        530                 535                 540

Leu Ser Asp Ile Ser Thr Ala Leu Arg Asn Pro Asn Ile Gln Arg Gln
545                 550                 555                 560

Pro Ser Arg Gln Ser Glu Arg Ala Arg Ser Gln Pro Met Val Leu Arg
                565                 570                 575

Gly Pro Ser Ala Glu Met Gln Gly Tyr Met Met Arg Asp Leu Asn Ser
                580                 585                 590

Ser Ile Asp Leu Gln Ser Phe Met Ala Arg Gly Leu Asn Ser Ser Met
            595                 600                 605

Asp Met Ala Arg Leu Pro Ser Pro Thr Lys Glu Lys Pro Pro Pro Pro
        610                 615                 620

Pro Pro Gly Gly Gly Lys Asp Leu Phe Tyr Val Ser Arg Pro Pro Leu
625                 630                 635                 640

Ala Arg Ser Ser Pro Ala Tyr Cys Thr Ser Ser Asp Ile Thr Glu
                645                 650                 655

Pro Glu Gln Lys Met Leu Ser Val Asn Lys Ser Val Ser Met Leu Asp
                660                 665                 670

Leu Gln Gly Asp Gly Pro Gly Gly Arg Leu Asn Ser Ser Ser Val Ser
            675                 680                 685

Asn Leu Ala Ala Val Gly Asp Leu Leu His Ser Ser Gln Ala Ser Leu
        690                 695                 700

Thr Ala Ala Leu Gly Leu Arg Pro Ala Pro Ala Gly Arg Leu Ser Gln
705                 710                 715                 720

Gly Ser Gly Ser Ser Ile Thr Ala Ala Gly Met Arg Leu Ser Gln Met
                725                 730                 735

Gly Val Thr Thr Asp Gly Val Pro Ala Gln Gln Leu Arg Ile Pro Leu
                740                 745                 750

Ser Phe Gln Asn Pro Leu Phe His Met Ala Ala Asp Gly Pro Gly Pro
        755                 760                 765

Pro Ala Gly His Gly Gly Ser Ser Gly His Gly Pro Pro Ser Ser His
    770                 775                 780

His His His His His His His Arg Gly Gly Glu Pro Pro Gly
785                 790                 795                 800

Asp Thr Phe Ala Pro Phe His Gly Tyr Ser Lys Ser Glu Asp Leu Ser
                805                 810                 815

Thr Gly Val Pro Lys Pro Pro Ala Ala Ser Ile Leu His Ser His Ser
            820                 825                 830

Tyr Ser Asp Glu Phe Gly Pro Ser Gly Thr Asp Phe Thr Arg Arg Gln
        835                 840                 845

Leu Ser Leu Gln Asp Asn Leu Gln His Met Leu Ser Pro Pro Gln Ile
```

-continued

```
            850                 855                 860
Thr Ile Gly Pro Gln Arg Pro Ala Pro Ser Pro Gly Gly Gly Ser
865                 870                 875                 880

Gly Gly Gly Ser Gly Gly Gly Gly Gly Gln Pro Pro Leu Gln
                885                 890                 895

Arg Gly Lys Ser Gln Gln Leu Thr Val Ser Ala Ala Gln Lys Pro Arg
                900                 905                 910

Pro Ser Ser Gly Asn Leu Leu Gln Ser Pro Glu Pro Ser Tyr Gly Pro
                915                 920                 925

Ala Arg Pro Arg Gln Gln Ser Leu Ser Lys Glu Gly Ser Ile Gly Gly
            930                 935                 940

Ser Gly Gly Ser Gly Gly Gly Gly Gly Leu Lys Pro Ser Ile
945                 950                 955                 960

Thr Lys Gln His Ser Gln Thr Pro Ser Thr Leu Asn Pro Thr Met Pro
                965                 970                 975

Ala Ser Glu Arg Thr Val Ala Trp Val Ser Asn Met Pro His Leu Ser
            980                 985                 990

Ala Asp Ile Glu Ser Ala His Ile Glu Arg Glu Tyr Lys Leu Lys
            995                 1000                1005

Glu Tyr Ser Lys Ser Met Asp Glu Ser Arg Leu Asp Arg Val Lys Glu
    1010                1015                1020

Tyr Glu Glu Ile His Ser Leu Lys Glu Arg Leu His Met Ser Asn
1025                1030                1035                1040

Arg Lys Leu Glu Glu Tyr Glu Arg Arg Leu Leu Ser Gln Glu Glu Gln
                1045                1050                1055

Thr Ser Lys Ile Leu Met Gln Tyr Gln Ala Arg Leu Glu Gln Ser Glu
                1060                1065                1070

Lys Arg Leu Arg Gln Gln Gln Val Glu Lys Asp Ser Gln Ile Lys Ser
    1075                1080                1085

Ile Ile Gly Arg Leu Met Leu Val Glu Glu Glu Leu Arg Arg Asp His
    1090                1095                1100

Pro Ala Met Ala Glu Pro Leu Pro Glu Pro Lys Lys Arg Leu Leu Asp
1105                1110                1115                1120

Ala Gln Arg Gly Ser Phe Pro Pro Trp Val Gln Gln Thr Arg Val
                1125                1130                1135
```

<210> SEQ ID NO 22
<211> LENGTH: 4272
<212> TYPE: DNA
<213> ORGANISM: Unknown Organism
<220> FEATURE:
<223> OTHER INFORMATION: Description of Unknown Organism: mammalian SYNGAP-A

<400> SEQUENCE: 22

```
aggatgggga tagcacccca gagtgaaggg gtctgtgtgg ggtaggtggt gtcctggggt    60
gagagggcag ctgagggtcc cactctccct cctggaatgg agcagtgggg ttgacagatg   120
ggtgccccaa ggaggcgtta agggagacaa tcccgctgtc ccttggtgac gtccagtcct   180
ggtggttggt gatgttccag ggtcgggtgc actgggaagg aggtctgtga cgctgggtgg   240 gccgggtag gtgcacagg gaaggaggtc tgtgatgctg ggtgggctag tggtctgcgg    300
tgttccggaa ctcgccgttc tctgtgatct gcagccgggg tggggggggt gggctgggg    360 gggccaggcc gttccaaggt gggggccagcg tcacacgcgg gtttgttgga cccaagggg   420 gaagctgcct ctctgagcgt cgagcagcct cttcttgggt tcaggcagcg gctcagccat   480
```

-continued

```
ggcggggtgg tcccggcgca gctcctcctc caccagcatc agcctgccaa tgatgctctt      540
gatctgggag tccttctcca cctgctgctg cctcaagcgc ttctcgctct gctccaggcg      600
ggcttggtac tgcatcagga tcttgctggt ctgctcttcc tgggacagca gcctccgctc      660
gtactcttcc agcttccggt tggacatgtg tagcctttcc ttcagtgagt ggatctcctc      720
ctcgtactcc ttcaccctgt ccagtcggct ctcgtccatg acttcgagt actccttcag       780 cttgtactct tcccgctcaa tgtgtgcact ctcgatgtca gcggacaggt gaggcatatt      840
ggacacccag gctacagtcc gctccgaggc cggcatcgtg gggttcagcg tggatggagt      900
ctgggaatgc tgcttggtga tggagggctt gagcccccca ccccctccgc caccgctgcc      960
cccgctgccc ccaatgctgc cctctttgct gaggctctgt tgccgtggac gggcaggacc     1020
ataacttggt tccggggact gcaataggtt cccgctggac ggccggggtt tctgggcagc     1080
actcactgtc aactgctgag atttgcccct ctgcaaggga ggtggctggc ccccaccgcc     1140
cccaccactg cccccaccac tgccccctcc tggccctgag ggagctggcc tctggggacc     1200
gatggtgatc tggggcgggg agagcatgtg ctgtaggttg tcctgaagtg agagctgccg     1260
acgggtaaaa tcagtaccag agggtccaaa ctcatcactg tagctgtggc tgtgaaggat     1320
ggaggccgca gggggcttag ggaccccctgt agagaggtcc tcgctcttgc tatagccatg     1380
gaacggggca aaagtgtccc ctgggggttc tcccctcgg tgatggtgat ggtggtggtg      1440
gtggtgatgg gaggaaggtg gaccatggcc actgctccct ccatggcctg ctgggggccc     1500
tggtccatcg gcagccatat ggaagagagg gttctggaag gaaagaggga tgcgcagttg     1560
ctgggcgggg acaccatccg tagtgacacc catctggctg aggcgcatgc cggctgctgt     1620
gatggaagag ccactcccttt gggagaggcg cccggcaggt gcaggccgca accccaaggc    1680
tgctgtcagt gaagcctggc ttgagtgcaa caggtcccca acagctgcca ggttggaaac     1740
actactgctg ttaaggcggc ccccaggccc gtcgccctgc aggtccagca tggacacact     1800
cttgttgaca ctcagcatct tctgctccgg ctctgtgatg tccgagctgc tcgtgcagta     1860
tgctggggag gaccgggcca gtggtggccg gctcacatag aacaggtctt tacccccacc     1920
gggagggggc ggcgggggtt tctccttggt tggggagggg aggcgagcca tgtccataga    1980
gctgttgagg cctcgagcca tgaaggactg aaggtcgatg gagctgttga ggtcccgcat     2040
catgtagccc tgcatctcgg ctgacggccc gcgcagcacc atgggctgag accgagcgcg     2100
ctcgctctgg cggctcggct gcctttggat gttagggttc ctcagggctg tgctgatgtc     2160
gctgaggagc cggggcagcg ggcccagctt caggagggct tccttgctga gctggggcag     2220
cacctcccag agcagggcgt gaagtgtgga gagctcgcgg cccaagtcta tgtagccctc     2280
aaaactgctg ctgttggtca gtgtgtccag gttggatatc tcatacaaga attgctgcat     2340 agaacccac tccagctcca gaaactcgtt catgaagccc aggaagtcct cctttgaggt      2400
aaacttggaa aagttggcca ggttctggat aaccttggcg atgagggtga gggttcgtga     2460
ggtctgctca tctgggtact cctgcatcag tccaaacaga ctgggcgaca tgatggccgg     2520
gcagaggaag cgcaggaaga gcgaggcgct gatcagcctg tcagcaatgt cctcccggcc     2580
ccgctctgca cagcgcagcc gccatgatgc aaacacctcc ttcagctccc tcgggaacac     2640
gcaatgggag ttgaccacct tgcacagggc caactcacag cacatccgca ggttggcctg     2700
gtgctctgcc agactggacg ctgtgcactt gatgggtct acttcacagt tctcctcaga      2760
ttcatacaga gcccggatga actccccaat ggcatccttg aggtatttct ggccaatcag     2820
```

-continued

```
tctcatatac tcttctatgg ctttagtggc gagcgtgttc tcgcggaata tgaggtgttc    2880
ccgctccatg aaccggtcta cctctgacat ggccatgtct gaaaggaagt ccttggcctt    2940
gcctgtgctt tgcaggatgt gaaccagtgc actagcgacc tcctccttgc ccttgacatt    3000
gagggcgggc tccagcacgg cacacagcat gcggtagtgg ttggtcacat attctgcaaa    3060
ctccttatat agctccatgg gcaggatact cattgtctgg taacgggcct tcagccgcac    3120
agcaggacag cctcctttcc ctttgccccc tgagccgccc cctgaccccc tcctcccccc    3180
cgagcccata cccccagagc ccccacttcc tgttggcagg gtcacggggt accactgctc    3240
tgtgaagtgg cgcccagcca gggtggccac tggaacagtc accaggccaa cgtagcctgc    3300
cttgtccttc ttccgctttt tgtccgagtc acggtacaga tgcagccgca gcgcccggac    3360
agcaggcagg ttgttaaact cgaagtgctc gccccaaaag acagtgtctc ctgaggctga    3420
gcggggcttg gaagtggtcc gtgcatagag catgtcgtcc aggcataact cgcagtaata    3480
tcgcttcttg gggggcagct ctcgagcttc tatgatccat agtttcagca cgttatctac    3540
ccggcggctg ttgtccttgt tgggtttcac agccctctgt agattctcaa tccatttgtc    3600
cctttcggct gcagaccgac aggcaaaaca ttttgtccca gacgatgttg ttacctcaaa    3660
gcagaactcc tggcccagga tggagctgtg tactggcttg ataatggagt cttcatccag    3720
gttgagctcc agggcctcag cagcactgct gggactcagc agggactcat gggagtgaga    3780
ctccttgaag ctctgcatca gccgggcccg gtcatggtca gcacttcgga agcgaggcag    3840
gatctgtcga aagctgctgg tccggtcaag tttgggttgt gactttgtac gtttgatgga    3900
gcttttagc ctccggctca ggaagccttg cgagggccgg aagggcgcag cggggcggc     3960
ttccatgctg tactgttttcc ccccggggac actcttcctc ctcgagcgac ccaagtggta    4020
ttcatgctcg ccgtggggcc gcccctccac tggcacagag acggtgcgtc tcagcagttt    4080
gtttcggctg gactcgctcc tccggtcgcg gatcagaagg gggtgtatct catcctcatc    4140
cagcatgagc agctggttcc cagagatgat gcagaaccgg gggttccaac cgggacggtc    4200
atacggggaa tgaacgtatt gggttcggtg catagggggt ccccgtacat ctctgaaggg    4260
ggcataggac at                                                       4272
```

<210> SEQ ID NO 23
<211> LENGTH: 4134
<212> TYPE: DNA
<213> ORGANISM: Unknown Organism
<220> FEATURE:
<223> OTHER INFORMATION: Description of Unknown Organism: mammalian
      SYNGAP-B

<400> SEQUENCE: 23

```
aggatgggga tagcacccca gagtgaaggg gtctgtgtgg ggtaggtggt gtcctggggt      60
gagagggcag ctgagggtcc cactctccct cctggaatgg agcagtgggg ttgacagatg    120
ggtgccccaa ggaggcgtta agggagacaa tcccgctgtc ccttggtgac gtccagtcct    180
ggtggttggt gatgttccag ggtcgggtgc actgggaagg aggtctgtga cgctgggtgg    240
gccggggtag ggtgcacagg gaaggaggtc tgtgatgctg ggtgggctag tggtctgcgg    300
tgttccggaa ctcgccgttc tctgtgatct gcagccgggg tggggggggt ggggctgggg    360
gggccaggcc gttccaaggt ggggccagcg tcacgcgcgg gtttgttgga cccaagggggg    420
gaagctgcct ctctgagcgt cgagcagcct cttcttgggt tcaggcagcg gctcagccat    480
ggcggggtgg tcccggcgca gctcctcctc caccagcatc agcctgccaa tgatgctctt    540
```

-continued

| | |
|---|---|
| gatctgggag tccttctcca cctgctgctg cctcaagcgc ttctcgctct gctccaggcg | 600 |
| ggcttggtac tgcatcagga tcttgctggt ctgctcttcc tgggacagca gcctccgctc | 660 |
| gtactcttcc agcttccggt tggacatgtg tagcctttcc ttcagtgagt ggatctcctc | 720 |
| ctcgtactcc ttcaccctgt ccagtcggct ctcgtccatg gacttcgagt actccttcag | 780 |
| cttgtactct tcccgctcaa tgtgtgcact ctcgatgtca gcggacaggt gaggcatatt | 840 |
| ggacacccag gctacagtcc gctccgaggc cggcatcgtg gggttcagcg tggatggagt | 900 |
| ctgggaatgc tgcttggtga tggagggctt gagcccccca cccctccgc caccgctgcc | 960 |
| cccgctgccc ccaatgctgc cctctttgct gaggctctgt tgccgtggac gggcaggacc | 1020 |
| ataacttggt tccgggggact gcaataggtt cccgctggac ggccgggatt tctgggcagc | 1080 |
| actcactgtc aactgctgag atttgccccct ctgcaaggga ggtggctggc ccccaccgcc | 1140 |
| cccaccactg cccccaccac tgcccccctcc tggccctgag ggagctggcc tctggggacc | 1200 |
| gatggtgatc tggggcgggg agagcatgtg ctgtaggttg tcctgaagtg agagctgccg | 1260 |
| acgggtaaaa tcagtaccag agggtccaaa ctcatcactg tagctgtggc tgtgaaggat | 1320 |
| ggaggccgca gggggcttag ggaccctgt agagaggtcc tcgctcttgc tatagccatg | 1380 |
| gaacggggca aaagtgtccc ctgggggttc tccccctcgg tgatggtgat ggtggtggtg | 1440 |
| gtggtgatgg gaggaaggtg gaccatggcc actgctccct ccatggcctg ctgggggccc | 1500 |
| tggtccatcg gcagccatat ggaagagagg gttctggaag gaaagaggga tgcgcagttg | 1560 |
| ctgggcgggg acaccatccg tagtgacacc catctggctg aggcgcatgc cggctgctgt | 1620 |
| gatggaagag ccactccctt gggagaggcg cccggcaggt gcaggccgca accccaaggc | 1680 |
| tgctgtcagt gaagcctggc ttgagtgcaa caggtcccca acagctgcca ggttggaaac | 1740 |
| actactgctg ttaaggcggc ccccaggccc gtcgccctgc aggtccagca tggacacact | 1800 |
| cttgttgaca ctcagcatct tctgctccgg ctctgtgatg tccgagctgc tcgtgcagta | 1860 |
| tgctggggag gaccgggcca gtggtggccg gctcacatag aacaggtctt taccccccacc | 1920 |
| gggaggggc ggcggggtt tctccttggt tgggagggg aggcgagcca tgtccataga | 1980 |
| gctgttgagg cctcgagcca tgaaggactg aaggtcgatg gagctgttga ggtcccgcat | 2040 |
| catgtagccc tgcatctcgg ctgacggccc gcgcagcacc atgggctgag accgagcgcg | 2100 |
| ctcgctctgg cggctcggct gcctttggat gttagggttc ctcagggctg tgctgatgtc | 2160 |
| gctgaggagc cggggcagcg ggcccagctt caggagggct tccttgctga gctggggcag | 2220 |
| cacctcccag agcagggcgt gaagtgtgga gagctcgcgg cccaagtcta tgtagccctc | 2280 |
| aaaactgctg ctgttggtca gtgtgtccag gttggatatc tcatacaaga attgctgcat | 2340 |
| agaaccccac tccagctcca gaaactcgtt catgaagccc aggaagtcct cctttgaggt | 2400 |
| aaacttggaa aagttggcca ggttctggat aaccttggcg atgagggtga gggttcgtga | 2460 |
| ggtctgctca tctgggtact cctgcatcag tccaaacaga ctgggcgaca tgatggccgg | 2520 |
| gcagaggaag cgcaggaaga gcgaggcgct gatcagcctg tcagcaatgt cctcccggcc | 2580 |
| ccgctctgca cagcgcagcc gccatgatgc aaacacctcc ttcagctccc tcgggaacac | 2640 |
| gcaatgggag ttgaccacct tgcacagggc caactcacag cacatccgca ggttggcctg | 2700 |
| gtgctctgcc agactggacg ctgtgcactt gatgggtct acttcacagt tctcctcaga | 2760 |
| ttcatacaga gcccggatga actccccaat ggcatccttg aggtatttct ggccaatcag | 2820 |
| tctcatatac tcttctatgg ctttagtggc gagcgtgttc tcgcggaata tgaggtgttc | 2880 |
| ccgctccatg aaccggtcta cctctgacat ggccatgtct gaaaggaagt ccttggcctt | 2940 |

-continued

| | | | | |
|---|---|---|---|---|
| gcctgtgctt | tgcaggatgt | gaaccagtgc | actagcgacc | tcctccttgc ccttgacatt | 3000 |
| gagggcgggc | tccagcacgg | cacacagcat | gcggtagtgg | ttggtcacat attctgcaaa | 3060 |
| ctccttatat | agctccatgg | gcaggatact | cattgtctgt | taacgggcct tcagccgcac | 3120 |
| agcaggacag | cctcctttcc | ctttgccccc | tgagccgccc | cctgacccc ctcctccccc | 3180 |
| cgagcccata | cccccagagc | ccccacttcc | tgttggcagg | gtcacggggt accactgctc | 3240 |
| tgtgaagtgg | cgcccagcca | gggtggccac | tggaacagtc | accaggccaa cgtagcctgc | 3300 |
| cttgtccttc | ttccgctttt | tgtccgagtc | acggtacaga | tgcagccgca gcgcccggac | 3360 |
| agcaggcagg | ttgttaaact | cgaagtgctc | gccccaaaag | acagtgtctc ctgaggctga | 3420 |
| gcggggcttg | gaagtggtcc | gtgcatagag | catgtcgtcc | aggcataact cgcagtaata | 3480 |
| tcgcttcttg | ggggcagct | ctcgagcttc | tatgatccat | agtttcagca cgttatctac | 3540 |
| ccggcggctg | ttgtccttgt | tgggtttcac | agccctctgt | agattctcaa tccatttgtc | 3600 |
| cctttcggct | gcagaccgac | aggcaaaaca | ttttgtccca | gacgatgttg ttacctcaaa | 3660 |
| gcagaactcc | tggcccagga | tggagctgtg | tactggcttg | ataatggagt cttcatccag | 3720 |
| gttgagctcc | agggcctcag | cagcactgct | gggactcagc | agggactcat gggagtgaga | 3780 |
| ctccttgaag | ctctgcatca | gccgggcccg | gtcatggtca | gcacttcgga agcgaggcag | 3840 |
| gatctgtcga | aagctgctgg | tccggtcaag | tttgggttgt | gactttgtac gtttgatgga | 3900 |
| gcttttagc | ctccggctca | ggaagccttg | cgagggccgg | aagggcgcag cggggcggc | 3960 |
| ttccatgctg | tactgtttcc | ccccggggga | cactcttcct | cctcgagcga cccaagtggt | 4020 |
| attccccgg | aaagcagcag | gaagagcagc | ggcggcggag | aggctggcgg tgggaaggag | 4080 |
| ggggcaagga | acctgaaccg | gagccccctg | acggggtcgg | ggtgggggc ctta | 4134 |

<210> SEQ ID NO 24
<211> LENGTH: 3981
<212> TYPE: DNA
<213> ORGANISM: Unknown Organism
<220> FEATURE:
<223> OTHER INFORMATION: Description of Unknown Organism: mammalian
    SYNGAP-C

<400> SEQUENCE: 24

| | | | | |
|---|---|---|---|---|
| aggatgggga | tagcacccca | gagtgaaggg | gtctgtgtgg | ggtaggtggt gtcctggggt | 60 |
| gagagggcag | ctgagggtcc | cactctccct | cctggaatgg | agcagtgggg ttgacagatg | 120 |
| ggtgccccaa | ggaggcgtta | agggagacaa | tcccgctgtc | ccttggtgac gtccagtcct | 180 |
| ggtggttggt | gatgttccag | ggtcgggtgc | actgggaagg | aggtctgtga cgctgggtgg | 240 |
| gccggggtag | ggtgcacagg | gaaggaggtc | tgtgatgctg | ggtgggctag tggtctgcgg | 300 |
| tgttccggaa | ctcgccgttc | tctgtgatct | gcagccgggg | tgggggggt ggggctgggg | 360 |
| gggccaggcc | gttccaaggt | ggggccagcg | tcacacgcgg | gtttgttgga cccaagggg | 420 |
| gaagctgcct | ctctgagcgt | cgagcagcct | cttcttgggt | tcaggcagcg gctcagccat | 480 |
| ggcggggtgg | tccggcgca | gctcctcctc | caccagcatc | agcctgccaa tgatgctctt | 540 |
| gatctgggag | tccttctcca | cctgctgctg | cctcaagcgc | ttctcgctct gctccaggcg | 600 |
| ggcttggtac | tgcatcagga | tcttgctggt | ctgctcttcc | tgggacagca gcctccgctc | 660 |
| gtactcttcc | agcttccggt | tggacatgtg | tagcctttcc | ttcagtgagt ggatctcctc | 720 |
| ctcgtactcc | ttcaccctgt | ccagtcggct | tcgtccatg | gacttcgagt actccttcag | 780 |
| cttgtactct | tcccgctcaa | tgtgtgcact | ctcgatgtca | gcggacaggt gaggcatatt | 840 |

-continued

```
ggacacccag gctacagtcc gctccgaggc cggcatcgtg gggttcagcg tggatggagt      900
ctgggaatgc tgcttggtga tggagggctt gagcccccca cccctccgc caccgctgcc       960 cccgctgccc ccaatgctgc cctctttgct gaggctctgt tgccgtggac gggcaggacc     1020
ataacttggt tccggggact gcaataggtt cccgctggac ggccggggtt tctgggcagc     1080
actcactgtc aactgctgag atttgcccct ctgcaaggga ggtggctggc ccccaccgcc     1140
cccaccactg cccccaccac tgccccctcc tggccctgag ggagctggcc tctggggacc     1200
gatggtgatc tgggcggggg agagcatgtg ctgtaggttg tcctgaagtg agagctgccg     1260
acgggtaaaa tcagtaccag agggtccaaa ctcatcactg tagctgtggc tgtgaaggat     1320
ggaggccgca gggggcttag ggaccctgt agagaggtcc tcgctcttgc tatagccatg      1380
gaacggggca aaagtgtccc ctgggggttc tcccctcgg tgatggtgat ggtggtggtg      1440
gtggtgatgg gaggaaggtg gaccatggcc actgctccct ccatggcctg ctgggggccc     1500
tggtccatcg gcagccatat ggaagagagg gttctggaag gaaagaggga tgcgcagttg     1560
ctgggcgggg acaccatccg tagtgacacc catctggctg aggcgcatgc cggctgctgt     1620
gatggaagag ccactcccct gggagaggcg cccggcaggt gcaggccgca accccaaggc     1680
tgctgtcagt gaagcctggc ttgagtgcaa caggtcccca acagctgcca ggttggaaac     1740
actactgctg ttaaggcggc ccccaggccc gtcgccctgc aggtccagca tggacacact     1800
cttgttgaca ctcagcatct tctgctccgg ctctgtgatg tccgagctgc tcgtgcagta     1860
tgctggggag gaccgggcca gtggtggccg gctcacatag aacaggtctt taccccacc     1920 gggagggggc ggcgggggtt tctccttggt tggggagggg aggcgagcca tgtccataga     1980
gctgttgagg cctcgagcca tgaaggactg aaggtcgatg gagctgttga ggtcccgcat     2040
catgtagccc tgcatttcgg ctgacggccc cgcagcacc atgggctgag accgagcgcg      2100
ctcgctctgg cggctcggct gcctttggat gttagggttc ctcagggctg tgctgatgtc     2160
gctgaggagc cggggcagcg ggcccagctt caggagggct tccttgctga gctggggcag     2220
cacctcccag agcagggcgt gaagtgtgga gagctcgcgg cccaagtcta tgtagccctc     2280
aaaactgctg ctgttggtca gtgtgtccag gttggatatc tcatacaaga attgctgcat     2340
agaaccccat tccagctcca gaaactcgtt catgaagccc aggaagtcct cctttgaggt     2400
aaacttggaa aagttggcca ggttctggat aaccttggcg atgagggtga gggttcgtga     2460
ggtctgctca tctgggtact cctgcatcag tccaaacaga ctgggcgaca tgatggccgg     2520
gcagaggaag cgcaggaaga gcgaggcgct gatcagcctg tcagcaatgt cctcccggcc     2580
ccgctctgca cagcgcagcc gccatgatgc aaacacctcc ttcagctccc tcgggaacac     2640
gcaatgggag ttgaccacct tgcacagggc caactcacag cacatccgca ggttggcctg     2700
gtgctctgcc agactggacg ctgtgcactt gatgggtct acttcacagt tctcctcaga      2760
ttcatacaga gcccggatga actccccaat ggcatccttg aggtatttct ggccaatcag     2820
tctcatatac tcttctatgg ctttagtggc gagcgtgttc tcgcggaata tgaggtgttc     2880
ccgctccatg aaccggtcta cctctgacat ggccatgtct gaaaggaagt ccttggcctt     2940
gcctgtgctt tgcaggatgt gaaccagtgc actagcgacc tcctccttgc ccttgacatt     3000
gagggcgggc tccagcacgg cacacagcat gcggtagtgg ttggtcacat attctgcaaa     3060
ctccttatat agctccatgg gcaggatact cattgtctgg taacgggcct tcagccgcac     3120
agcaggacag cctcctttcc ctttgccccc tgagccgccc cctgacccc ctcctccccc      3180
```

-continued

```
cgagcccata cccccagagc ccccacttcc tgttggcagg gtcacggggt accactgctc    3240
tgtgaagtgg cgcccagcca gggtggccac tggaacagtc accaggccaa cgtagcctgc    3300
cttgtccttc ttccgctttt tgtccgagtc acggtacaga tgcagccgca gcgcccggac    3360
agcaggcagg ttgttaaact cgaagtgctc gccccaaaag acagtgtctc ctgaggctga    3420
gcggggcttg gaagtggtcc gtgcatagag catgtcgtcc aggcataact cgcagtaata    3480
tcgcttcttg gggggcagct ctcgagcttc tatgatccat agtttcagca cgttatctac    3540
ccggcggctg ttgtccttgt tgggtttcac agccctctgt agattctcaa tccatttgtc    3600
cctttcggct gcagaccgac aggcaaaaca ttttgtccca gacgatgttg ttacctcaaa    3660
gcagaactcc tggcccagga tggagctgtg tactggcttg ataatggagt cttcatccag    3720
gttgagctcc agggcctcag cagcactgct gggactcagc agggactcat gggagtgaga    3780
ctccttgaag ctctgcatca gccgggcccg gtcatggtca gcacttcgga agcgaggcag    3840
gatctgtcga aagctgctgg tccggtcaag tttgggttgt gactttgtac gtttgatgga    3900 gcttttttagc ctccggctca ggaagccttg ctggggagca aatgggaaat ggggtgcttg    3960
gggcagctca gtctctccct a                                              3981
```

SIGNAL TRANSDUCING SYNAPTIC MOLECULES AND USES THEREOF

CROSS-REFERENCE TO RELATED APPLICATIONS

The present application is a continuation of pending U.S. provisional application Ser. No. 60/082,690 filed on Apr. 22, 1998, and pending U.S. provisional application Ser. No. 60/082,717 filed on Apr. 23, 1998, the disclosures of both provisional applications fully incorporated herein by reference.

BACKGROUND OF THE INVENTION

1. Field of the Invention

The present invention relates to signal transducing synaptic molecules and particularly to mammalian SYNGAP (Synaptic GTPase Activating Protein), including recombinant SYNGAPs and fragments and derivatives thereof. In one aspect, the invention provides molecules for detecting and analyzing SYNGAPs in vitro and in vivo. In another aspect, the invention provides assays for detecting compounds that modulate SYNGAP or SYNGAP-related activities. The invention has a variety of applications including use in screens to detect pharmacological agents useful in the diagnosis or treatment of disorders associated with SYNGAP.

2. Background

Neurons communicate by a variety of means including synaptic transmission. One form of synaptic transmission involves chemical signaling; a process generally involving neurotransmitter release from one neuron and modulation of a post-synaptic receptor in another neuron. The release and modulation is usually manifested by propagation of a chemical or electrical impulse. See Edelman, G. M. et al. (eds.) (1987) in *Synaptic Function*, New York: Wiley; and Goodman and Gilman (1996) in *The Pharmacological Basis of Therapeutics*, 9$^{th}$ ed. J. G. Hardman, et al. (eds) Pergamon Press, NY.

In many instances, chemical signaling requires specialized neuronal structures called chemical synapses. Analysis of chemical synapses has attracted substantial interest. For example, chemical synapses have been reported to be involved in many, if not all, nervous system functions including neuronal plasticity. In particular, neuronal plasticity is believed to impact critical functions such as cognition, e.g., memory and learning, as well as certain neurodegenerative disorders. See e.g., Kandel, E. R. et al; (1991) in *Principles of Neuroscience*, Appleton & Lange, Norwalk, Conn. and references cited therein.

A variety of approaches have been used in attempts to understand chemical synapses. For example, certain molecular and biochemical approaches have suggested that chemical synapses are structured and include molecules such as receptors, cytoskeletal proteins, and signal transduction molecules. See e.g., Ehlers, M. D., et al. (1996) *Curr. Opin. Cell Biol.* 8: 484; Sheng, M. (1996) *Neuron* 17:575; and Huganir, R. L. and Greengard, M. (1990) *neuron* 5: 555.

More particularly, it has been reported that appropriate chemical synapse structure requires presence of a protein termed PSD-95/SAP90. The PSD-95/SAP90 protein is representative of a family of molecules including SAP120. Specific members of the PSD-95/SAP90 family are localized at or near chemical synapses. See e.g., Ehlers, M. D., et al. supra; Sheng, M supra; Lau, L. F., et al. (1996) *J. Biol. Chem.* 271:21622; Muller, B. M., et al. (1996) *Neuron* 17:255; and references cited therein.

There has been much effort towards understanding PSD-95/SAP90 and related proteins. For example, it has been reported that most members of the protein family exhibit the same or a closely related structure, i.e., three tandem PDZ (PSD-95, DLG, ZO-1) domains, a SH3 (src homology 3) domain, and an inactive yeast guanylate kinase domain (GK). See e.g., Kim, E., et al. (1995) *Nature* 378:85; Kornau, H. C., et al. (1995) *Science* 269:1737.

There has been recognition that PDZ domains exist in proteins associated with cell membranes. For example, it has been reported that the PDZ domains of PSD-95 bind to specific subunits of the (N-methyl-D-aspartate) NMDA receptor. It has also been reported that the last three amino acids of the NMDA receptor subunits define a consensus sequence (T/SXV; X is any amino acid). The subunit sequence has been reported to facilitate the binding. See e.g., Kennedy, M. B. (1995) *Trends Biochem. Sci.* 20; Gomperts, S. N. (1996) *Cell* 84:659; Sheng, M. supra.

There has also been recognition that chemical synapses can employ signal transduction to modulate pre- and post-synaptic activity. For example, certain members of the PSD-95/SAP90 protein family are believed to be associated with signal transduction. More particularly, the PSD-95 protein has been proposed to interact with certain signal transduction kinases. That interaction has been proposed to be important to synaptic function. See Gomperts, supra; Saras, J., and Heldin, C. H. (1996) *Trends Biochem. Sci.* 21:455; Huganir, R. L. and Greengard, M. supra.

There has also been recognition that the PSD-95/SAP90 protein may be capable of serving as an adaptor molecule. More specifically, there have been reports that the PSD-95/SAP90 protein may be able to relate synaptic activity and signal transduction in some instances. That property is believed to important to appropriate synapse function. See e.g., Brenman, J. E. et al. (1996) *Cell* 84: 757; and Saras, J. and Heldin, Carl-Henrik (1996), supra.

A variety of signal transduction molecules are known including specified kinases and proto-oncogenes. For example, the proto-oncogene Ras is recognized as a G-protein that is apparently involved in signal transduction pathways affecting, e.g., cell growth, cell differentiation, neuronal plasticity and cell survival. In particular, Ras appears to have a substantial role in kinase activation. In addition, biological activity manifested by a variety of neurotrophic factors (i.e. neurotrophins) may be derived through Ras-associated signaling pathways. See e.g., Bokoch, G. M., and Der, C. J. (1993) *FASEB. J.* 7:750; Marshall, C. J. (1996) *Cell Biol.* 8:197; Finkbeiner, S. and Greenberg, M. E. (1996) *Neuron* 16:233; Kang, H., and Schuman, E. M. (1996) *Science* 273:1402.

Certain neuronal functions have been proposed to be affected by Ras-mediated signal transduction. See e.g., Seger, R., and Krebs, E. G. (1995) *FASEB J.* 9:726; and Finkbeiner and Greenberg, supra.

Additional signal transduction pathways are known. For example, the inositol triphosphate signaling pathway has been reported to couple modulation of certain receptors to a variety of functions, many of which relate to calcium. See e.g., Berridge, M. J. (1988) *Pro. R. Soc. Lond.* (*Biol*) 234: 359.

It would be desirable to identify molecules that impact chemical synapse function and particularly interact with the PSD-95/SAP90 protein. It would be further desirable to identify molecules that can bind the PSD-95/SAP90 protein and affect signal transduction. It would also be desirable to have effective assays for identifying compounds and especially pharmaceutical agents with capacity to modulate the function of these molecules.

SUMMARY OF THE INVENTION

The present invention features molecules that relate to SYNGAP (Synaptic GTPase Activating Protein); an excitatory synapse protein that has been found to bind synaptic proteins and modulate signal transduction. In one aspect, the invention provides isolated polynucleotides that encode SYNGAP or fragments or derivatives thereof Further provided are SYNGAP or SYNGAP-related polypeptide encoded by the polynucleotides. In another aspect, the invention provides immunological molecules that are capable of binding the polypeptides. Additionally provided are methods for using the molecules of this invention, e.g., to treat or prevent at least one disorder mediated by SYNGAP. The invention also provides screening assays for detecting compounds useful in the diagnosis or treatment of disorders impacted by SYNGAP.

We have discovered mammalian SYNGAP: a novel protein that binds synaptic proteins important for chemical synapse function. Additionally, we have found that SYNGAP is capable of modulating certain signal transduction molecules and particularly the Ras proto-oncogene (Ras). We have particularly found that SYNGAP is positioned to relate synaptic activity and signal transduction, thereby indicating a significant role in many aspects of nervous system function.

As will be discussed below, SYNGAP is represented by a family of alternatively spliced variants including SYNGAP-a, SYNGAP-b, and SYNGAP-c.

The present invention provides a number of significant uses and advantages. For example, the invention relates, for the first time, recognized synaptic proteins such as PSD95/SAP90 and SAP120 to signal transduction. More particularly, the invention provides SYNGAP and SYNGAP-related molecules that are believed to serve as adaptors between key synaptic proteins and specific transduction pathways. Accordingly, the present invention is expected to facilitate attempts to more fully understand relations between synapses and signal transduction, particularly relationships between synaptic function and signaling molecules such as Ras, inositol triphosphate and certain other transduction molecules.

The present invention has a wide spectrum of important applications. For example, specific molecules of this invention can be used as a diagnostic tool to detect excitatory synapses, i.e., those that include mammalian SYNGAP. Illustrative of such excitatory synapses are those impacting neuronal plasticity, particularly habituation, sensitization, leaning and memory; as well as certain neurological disorders. In addition, the invention can be employed in the diagnosis, treatment or prophylaxis of certain neurological disorders impacted by SYNGAP. As will be discussed in more detail below, exemplary neurological conditions include those specifically affecting awareness and cognition as well as neuronal growth and survival.

Further, the present invention provides a variety of highly useful molecular markers including polynucleotides, polypeptides, and immune system molecules that can be used in many commercial, medical, home or research settings. For example, certain molecules of this invention can be used in screening assays to detect compounds and particularly pharmaceutical agents useful in the diagnosis or treatment of neurological disorders impacted by SYNGAP. Of particular interest are recognized manipulations that can be employed for the identification of small molecules, e.g., synthetic peptides, peptide mimetics, drugs, etc., that can modulate interaction between SYNGAP and the synaptic proteins to which it associates; interaction between SYNGAP and signal transduction molecules or both. Related techniques can be used to screen for small molecules that potentially block or enhance one or all of these interactions. In particular, in vitro screens are provided that can detect SYNGAP antagonists or agonists.

Additional uses include use of SYNGAP polynucleotides to detect SYNGAP expression in desired cells or groups of cells such as tissue or an organ by conventional in situ hybridization methods.

Particularly useful are SYNGAP-binding immune system molecules of this invention such as the antibodies and antigen-binding antibody fragments provided below. For example, the antibodies (monoclonal and polyclonal) can be used alone or in combination with other agents to facilitate identification of excitatory chemical synapses that include SYNGAP. In some instances, it may be desirable to include the antibodies wholly or as part of a therapeutic strategy to monitor or in some cases modulate the excitatory chemical synapses. Preferred molecules of the invention are flexible and can be modified, if desired, to deliver a desired molecule such as a drug, toxin, enzyme or radionuclide optionally through a linker sequence such as a peptide linker sequence. As an illustration, a SYNGAP binding antibody of this invention can be detectably-labeled to identify excitatory chemical synapses in vitro or in vivo.

The SYNGAP and SYNGAP-related molecules of this invention have additional uses and advantages in vitro and in vivo. For example, the molecules can be employed in functional, cellular and molecular assays (e.g., screens) and in structural analysis, including X-ray crystallography, nuclear magnetic resonance imaging (NMRI), computational techniques. Of particular interest are those techniques involving computer-assisted simulation of synapses (i.e. formulation of virtual synapses). Also included are useful techniques for using the SYNGAP and SYNGAP-related molecules as markers that can provide diagnostic imaging of excitatory chemical synapses in vivo. By way of illustration, certain molecules of this invention can be employed to visualize specific neurons and particularly chemical synapses including SYNGAP in the brain of a living patient. In this embodiment, the desired molecule will usually be detectably-labeled with a suitable tag such as a radionuclide or other suitable imaging component known in the field.

Specific SYNGAP and SYNGAP-related molecules of this invention can be provided in a kit form or other convenient form to facilitate manufacture, packaging, dissemination, storage, and/or use of the present invention.

Accordingly, in one aspect, the invention provides isolated polynucleotides (RNA, mRNA, cDNA, genomic DNA, or chimeras thereof) that encode SYNGAP or a fragment or derivative of SYNGAP. Illustrative of such polynucleotides include those encoding a mammalian SYNGAP, e.g., a primate and particularly a rat or a human SYNGAP. In one embodiment, the polynucleotide encodes a mammalian SYNGAP having a molecular weight of between about 100 to about 15 kDa or greater. In another embodiment, the polynucleotide has at least about 70 percent sequence identity to any of the nucleotide sequences shown in SEQ ID NOS. 1, 3, or 5. Such sequence similarity (i.e. about 70%) or greater similarity will sometimes be referred to herein as "substantial homology" or like term. Specifically preferred polynucleotides of the invention encode the rat SYNGAP shown in any of the SEQ ID Nos. 2, 4, or 6.

In another aspect, the present invention provides an isolated polynucleotide that is capable of hybridizing to the nucleotide sequence shown n SEQ ID Nos. 1≧2, 4–5, or 7–8 under moderate stringency hybridization conditions. In a preferred embodiment, the polynucleotide will also hybridize to those specific sequences shown in SEQ ID NOS. 1–2, 4–5, or 7–8 under high stringency conditions. The terms "moderate" and "high" hybridization stringency have readily understandable meaning to those of skill in this field. Exemplary stringency conditions are disclosed in the discussion and examples which follow. In one embodiment, the polynucleotide capable of hybridizing to the SEQ ID NO: 1 or under high stringency conditions is between from about 12 to about 50 nucleotides in length. Illustrative of such polynucleotides are oligonucleotide primers made by conventional synthetic methods. In another embodiment, the polynucleotide is between about 100 to about 3500 nucleotides in length or greater. Illustrative of such polynucleotides are restriction enzyme fragments or chemically synthesized fragments complementary to the sequences shown in SEQ ID Nos. 1, 3, or 5.

In another embodiment of the invention, the polynucleotide capable of hybridizing to the nucleotide sequence shown in SEQ ID Nos. 1, 3, or 5 under high stringency conditions has a length of between about 100 up to about 4000 nucleotides or greater. In a preferred embodiment, the polynucleotide is a cDNA encoding an amino acid sequence capable of modulating the proto-oncogene Ras as determined, e.g., by a standard Ras GTPase activity assay. In a specific embodiment, the amino acid sequence encoded by the polynucleotide is capable of inhibiting the Ras protein by at least about 10% up to about 100% in the standard Ras GTPase assay. Additionally preferred are polynucleotides that encode polypeptides capable of modulating Ras-mediated signaling transduction pathways and optionally signal transduction molecules "downstream" of Ras (directly or indirectly). Examples of such downstream molecules include recognized signaling and effector molecules. Illustrative methods for identifying such polynucleotides and amino acid sequences are described below.

One or a combination of standard approaches can be used to monitor Ras GTPase activity in cells or cell lysates. Preferably, the cell or cell lysate will include a naturally-occurring or recombinant Ras protein. Preferred assays for measuring and quantitating the Ras GTPase activity are discussed below.

Additionally preferred polynucleotides of this invention encode a mammalian SYNGAP or fragment or derivative thereof that is capable of significantly reducing inositol triphosphate signaling as determined, e.g., by modulation of phospholipase C activity in a standard phospholipase C enzyme assay. Preferably, the polynucleotide is a cDNA that is capable of increasing or decreasing the enzyme activity by at least about 10% or more up to about 100% relative to a suitable control assay. Specific phospholipase C assays are described below.

Additionally preferred polynucleotides of this invention encode a mammalian SYNGAP or a SYNGAP-related amino acid sequence that is capable of binding at least from about 1, 2 or 3 up to about 10 PDZ domains as determined by a standard PDZ domain binding assay. As noted above, the PDZ domain has been reported to be present in a variety of membrane proteins, e.g., the PSD95/SAP90 and SAP 120 proteins, and is believed to significantly impact chemical synapses.

By the term "SYNGAP-related" nucleotide or amino acid sequence or similar term is meant a fragment or derivative of SYNGAP sequence (polynucleotide or polypeptide as described below.

A variety of methods are known in this field for detecting and quantifying, if desired, PDZ binding. In general, the methods are capable of detecting formation of a binding complex and can be optimized to provide qualitative or quantitative characterization of those binding complexes. Illustrative methods for detecting the PDZ binding are more fully disclosed in the discussion and examples that follow.

Additionally preferred polynucleotides are those molecules that encode an amino acid sequence that includes at least a Ras GTPase Activating Protein (GAP) domain up to about 2 to about 3 GAP domains, and a C-terminal sequence that includes at least the following general amino acid sequence: (T or S), X V; wherein X is an amino acid, preferably one of the 20 natural amino acids.

Further preferred are those polynucleotides that encode an amino acid sequence that includes at least one pleckstrin homology (PH) up to about 3 PH domains and at least one C2 domain up to about 3 C2 domains.

Particularly preferred polynucleotides of this invention encode an amino acid sequence that includes in an N- to C-terminal orientation: at least one PH homology, preferably one PH homology; at least one C2 domain, preferably one C2 domain; at least one GAP domain, preferably one GAP domain; and the C-terminal sequence having the sequence (T or S), X V described above. Additionally preferred is a polynucleotide encoding an amino acid sequence that includes in an N- to C-terminal direction at least about the following amino acids of SEQ ID NO. 6, 4 to 72, 87 to 190, 266 to 502 and 1132 to 1135.

Specifically preferred are those polynucleotides that encode a rat SYNGAP as represented by any one of SEQ ID NOS. 2, 4 or 6 including fragments or derivatives thereof.

One or a combination of different strategies can be used to analyze the SYNGAP or SYNGAP-related molecules disclosed herein, e.g., to detect homologous molecules or to identify protein domains (e.g., GAP, PH, and C2). Specifically included are biochemical, immunological and biosensor-type assays as well as certain well-known computer-assisted manipulations.

Additionally provided by the present invention are fragments or derivatives of the polynucleotides encoding mammalian SYNGAP or SYNGAP-related molecules, as well as recombinant vectors including the polynucleotides or the fragments or derivatives thereof It is generally preferred that the recombinant vector be capable of propagating the isolated polynucleotide in a suitable prokaryotic or eukaryotic host cell. Additionally preferred recombinant vectors are capable of expressing that isolated polynucteotide as RNA and preferably mRNA, in a suitable cell expression system. The recombinant vector can include nearly any number of useful elements, however in most cases the vector will include control elements operably linked to the inserted nucleic acid (e.g., promoter, leader, and/or enhancer elements) which control elements can be selected to optimize replication and/or transcription of the vector in the cells.

As noted, polynucleotides of the invention generally encode mammalian SYNGAP or a fragment or derivative thereof In one embodiment, the polynucleotides are substantially homologous to the SYNGAP sequence shown in SEQ ID NO: 2, 4, or 6. In a specific embodiment, the isolated polynucleotides include or consists of cDNA and have a length of between about 50 to about 100 nucleotides up to about 4000 nucleotides or more, as determined by standard nucleic acid sizing methods. In another embodiment, the isolated nucleic acid includes or consists of RNA and particularly mRNA that is also substantially homologous to the specific rat SYNGAP sequence and which can have substantially the same length as the cDNA.

Also provided are host cells that include a polynucleotide as disclosed herein including those that express SYNGAP, a SYNGAP-related molecule or a fragment or derivative thereof under suitable cell culture conditions. Preferably, the host cells are capable of expressing the desired amino acid sequence in the host cell, cell medium, or both.

The invention also includes methods for isolating a polynucleotide encoding a mammalian SYNGAP or SYNGAP-related molecule such as the rat SYNGAP sequence specifically described below. In general, the methods include introducing the polynucleotide into host cells, typically as a recombinant vector including the polynucleotide, culturing the host cells under conditions suitable for propagating the polynucleotide and purifying the polynucleotide from the host cells to obtain larger portion of the isolated polynucleotide therefrom. Host cells useful for propagating the polynucleotides and/or polypeptides of this invention can be eukaryotic, prokaryotic, more particularly, fungal, yeast, animal or insect as desired. Host cells amenable for large scale production of mammalian SYNGAP are especially useful for commercial and industrial applications. Alternatively PCR amplification or related amplification methods can be used to isolate the polynucleotide.

Further provided are cultured host cells which have been transformed, transfected or infected either transiently or stably by at least one recombinant vector of the invention which vector includes an isolated polynucleotide that encodes a mammalian SYNGAP or a fragment or derivative thereof (DNA or RNA).

Recombinant vectors of the invention can be introduced into suitable cells or groups of such cells including tissue or organs if desired either in vitro or in vivo. Preferably, the cells are capable of expressing the recombinant vector at detectable levels. Host cells comprising the vectors can be cultured in medium capable of supporting propagation and/or expression of the vectors in the cells. The cells can be eukaryotic cells, preferably mammalian cells such as neurons and neuron-associated cells (e.g., glia) which cells are capable of expressing desired sequences in the recombinant vector. The cells can be primary cells or the cells can be immortalized. In some instances it will be desirable to introduce the vector into a suitable prokaryotic host e.g., bacteria, insect, yeast or fungal cells to propagate the vector.

The present invention also provides useful oligonucleotide primers, typically single-stranded primers, which oligonucleotide primers are complementary to a polynucleotide encoding a mammalian SYNGAP. For example, in one embodiment, the oligonucleotide primers are complementary to the rat SYNGAP sequence shown in any one of SEQ ID Nos. 1, 3, or 5. The oligonucleotide primers have a variety of useful applications, e.g., to detect or amplify a mammalian SYNGAP of interest. Exemplary oligonucleotide primers will generally have length of between about 12 to about 70 nucleotides although somewhat larger or smaller primers are useful for some applications.

Additional polynucleotides of the present invention have important uses. For example, as discussed, the invention provides for recombinant vectors that include an isolated polynucleotide relating to SYNGAP. Specific recombinant vectors can be used to produce significant amounts of nucleic acid sequence that can be sense or anti-sense, single-stranded or double-stranded as needed. Generally, RNA transcribed from DNA is referred to as the "sense" RNA strand and oppositely oriented RNA is termed antisense RNA. Antisense polynucleotides, then, refer to sequences of DNA or RNA which can bind in a Watson-Crick fashion to a sequence on a target mRNA. See generally Bentley, D. L. and Groudine, M. (1986) *Nature* 321:702; and Kimelman, D. *Gene regulation: Biology of Antisense RNA and DNA*, R. P. Erickson, J. G. Izant, eds. (Raven Press, New York).

Mammalian SYNGAP RNA and particulary a SYNGAP mRNA existing in a biological sample such as in an excitatory chemical synapse (in vivo or in vitro) will sometimes be referred to herein as a "target" to denote potential for specific binding between a polynucleotide of interest, e.g., a suitable anti-sense RNA, and the SYNGAP mRNA in the sample.

In one preferred embodiment, the recombinant vectors include DNA sequences that encode an anti-sense RNA which RNA is substantially homologous to mammalian SYNGAP polynucleotides of this invention e.g., a rat SYNGAP. It is preferred that the recombinant vectors include cDNA sequences. In this instance it will be understood that the anti-sense RNA will usually include a uracil (U) in place of thymidine (T) where the cDNA sequence has a thymidine. In a preferred embodiment, the anti-sense RNA has a length of at least about 20 to about 50 nucleotides, at least about 100 to about 250 nucleotides, at least about 300 to about 700 nucleotides, at least about 1000 to about 2000 nucleotides and up to about 2500 to about 4000 nucleotides as determined by standard polynucleotide sizing methods. In most cases, the length of the anti-sense RNA will be guided by intended use including the length of the target and the level of anti-sense suppression desired.

The antisense RNA encoded by specific recombinant vectors of this invention is usually designed to undergo complementary base pairing (hybridization) with the target, rendering the target essentially unavailable for translation in most cases. In some instances, the antisense RNA will render the target susceptible to degradation, thereby substantially reducing the amount of the target in relevant cells or tissue. Accordingly, the recombinant vectors of the invention can be used to control the synthesis and/or expression of SYNGAP in desired neurons in vitro or in vivo.

Specific recombinant vectors of this invention that are capable of producing anti-sense RNA complementary to a mammalian SYNGAP mRNA (or more than one of such mRNA) can be used therapeutically to reduce levels of the target in vivo or in vitro. For example, in one embodiment, a desired recombinant vector is administered to a patient suffering from or suspected of suffering from a SYNGAP related disorder such as those specified herein. In this instance, the patient will benefit from substantially reduced or totally absent levels of the target. Preferred administration is sufficient to reduce levels of the target mRNA in the patient. Efficacy of the technique can be monitored and quantified if desired by a variety of techniques including Northern and Western blotting.

In another embodiment, the recombinant vector is formatted to produce anti-sense DNA of about the same size as the anti-sense RNA.

In addition, the polynucleotides of this invention and particularly the isolated nucleic acids and recombinant vectors described herein can be used as important controls for detecting and analyzing normal and aberrant mammalian SYNGAP expression in vitro and in vivo.

In another aspect, the present invention provides isolated mammalian SYNGAP preferably having an apparent molecular weight of between about 100 to about 150 kDa. The molecular weight of the SYNGAP can be determined by a variety of standard means including polyacrylamide gel electrophoresis. Preferred are polypeptide sequences having at least about 200 amino acids up to about 1000 amino acids or greater including about 1100 amino acids. Specifically provided is rat SYNGAP as shown at the amino acid sequence level in any one of SEQ ID NOS. 2, 4, or 6.

In another aspect, there is provided an isolated polypeptide having at least about 170 percent amino acid sequence homology to the sequence illustrated in SEQ ID NO: 2, 4, or 6. Additionally provided are isolated fragments or derivatives of that polypeptide.

The invention also provides methods for producing a mammalian SYNGAP in which the method includes culturing the host cell in medium under conditions suitable for expression of the SYNGAP in the host cell or medium.

In another aspect, the present invention provides an antibody or antigen-binding fragment thereof capable of binding the amino acid sequence shown in SEQ ID NO. 6. Preferably, the binding of the antibody or antigen-binding fragment is blocked by at least about 80%, 90% or more up to about 100% by contact with the amino acid sequence shown in SEQ ID NO:21 or a sequence substantially homologous thereto. The percent blocking by the amino acid sequence can be determined by a variety of means including a conventional immunoprecipitation assay or a Western immunoblot.

In one preferred embodiment, the antibody is a capable of binding excitatory synapses as determined by microscopy. In this embodiment, the antibody can be a monoclonal or a polyclonal antibody or an antigen-binding fragment thereof. In most cases, the antibody or antigen-binding fragment will be detectably-labeled or will be capable of generating a detectable label as specified below to help visualize and optionally quantitate synaptic binding.

Additionally, the invention pertains to methods for making specific immune system molecules and particularly antibodies (polyclonal, monoclonal or chimeric molecules) which bind certain SYNGAP or a SYNGAP-related molecules described herein. The methods generally include using a substantially purified sample of a desired SYNGAP polypeptide, as immunogen. Exemplarly antibodies are monoclonal antibodies obtained by conventional hybridoma manipulations. The antibodies can also be generated from an immunogenic peptide that comprises one or more epitopes of the polypeptide. It will be useful in some settings to covalently attach a suitable cytotoxic, anti-metabolic, or detectable label to the antibody by methods well-known in the field to help detect and/or modulate desired synapses that include mammalian SYNGAP and particularly human or rat SYNGAP in vitro or in vivo.

It will be understood that an "immune system molecule" generally relates to antibodies and antigen-binding fragments of those antibodies that are derived from the immune system of a mammal such as a mouse, rat, rabbit, human, and the like.

The immune system molecules of this invention provide a number of uses and advantages. For example, the immune system molecules can be used to modulate mammalian SYNGAP expression in vitro or in vivo, e.g., by employing conventional microinjection techniques. In one approach, a suitable amount of a desired SYNGAP antibody is suspended in a physiologically acceptable buffer and injected into a desired cell or group of cells including tissue or an organ, which amount is sufficient to reduce or eliminate SYNGAP expression as determined, e.g., by the biochemical and functional assays described herein. In some instances, such approaches will be well-suited to modulate SYNGAP function, e.g., to impact neuronal plasticity in vitro or in vivo.

In another aspect, the present invention provides a kit that typically includes at least one container means comprising at least one of: 1) an antibody or antigen-binding fragment thereof capable of binding mammalian SYNGAP, 2) an isolated polynucleotide comprising sequence with at least about 70% sequence homology to any one of the sequences shown in SEQ ID NOs: 1, 3, or 5; 3) a pair of oligonucleotide primers capable of hybridizing to any one of the sequences shown in SEQ ID NOs: 1, 3, or 5, preferably under high stringency conditions; and 4) a polypeptide with at least about 70% to about 100% sequence homology to the sequence shown in any one of the sequences shown in SEQ ID NOs: 2, 4, or 6 a fragment or a derivative thereof.

In one embodiment, the kit includes a system for: 1) treating or preventing a disorder in a mammal associated with the SYNGAP, 2) detecting excitatory synapses in a cell or group of cells in vitro or in vivo, or both.

Isolated polynucleotides and polypeptides of the invention can be obtained as a substantially pure preparation if desired. That is, the nucleic acids and polypeptides can be isolated in substantially pure form by standard methods and can be provided as sterile preparations if desired. Methods for providing substantially pure preparations of nucleic acids and polypeptides are discussed below.

In another aspect of the present invention, there is provided methods for modulating excitatory synapse function in a cell or group of cells in vitro or in vivo. In this embodiment, the method includes administering to the cells a modulation effective amount of at least one polynucleotide of this invention or fragment or derivative thereof By the term "modulation effective" is meant a change in exciting synapse function (e.g., amout of SYNGAP).

The present invention also includes methods for modulating excitatory synapse function in a cell or group of cells in vitro or in vivo. In this embodiment, the method includes administering to the cells a modulation effective amount of a mammalian SYNGAP of this invention, including a fragment or derivative thereof In embodiments of the methods for modulating excitatory synapse function, the modulation can include an increase in excitatory synapse number. Excitatory synapses can be visualized and quantified, if desired, by a variety of means including microscopy or centrifugation.

In another aspect, the present invention includes methods for treating a disorder associated with a mammalian SYNGAP including administering to a patient suffering from or susceptible to such disorder an effective amount of at least one isolated polynucleotide of this invention or fragment or derivative thereof Additionally provided are methods for treating a disorder associated with a mammalian SYNGAP comprising administering to a patient suffering from or susceptible to such disorder an effective amount of an isolated SYNGAP of this invention or fragment or derivative thereof In embodiments of the methods for treating SYNGAP-related disorders, the disorder can be a neurological disorder of the central (CNS) or peripheral (PNS) nervous system. In a specific embodiment, the CNS disorder is at least one of an affective disorder, a cognitive disorder, or a neurodegenerative disorder. For example, the affective disorder can be depression; the cognitive disorder can be at least one of memory loss, a learning disability, or schizophrenia; and the learning disability can be attention deficit disorder (ADD). In another specific embodiment, the degenerative disorder can be at least one of Parkinson's disease (PD), Huntington's disease (HD), senile dementia, or Alzhemier's disease (AD). In a further specific embodiment, the PNS disorder is amyotrophic lateral sclerosis. In another specific embodiment, the neurological disorder is associated with at least one of trauma, an immune response or ischemia.

The methods for treating or preventing the SYNGAP-related disorders will also find applicability in the manipulation of habituation, sensitization, learning and memory in research settings.

As noted, the present invention provides a variety of screening assays for detecting compounds and especially pharmaceutical agents for use in the diagnosis or treatment of disorders impacted by mammalian SYNGAP.

In one embodiment, there is provided methods for identifying a compound useful in the diagnosis or treatment of a disorder relating to the SYNGAP. In a specific embodiment, the method includes at least one of the following steps:
  a) culturing cells capable of forming synapses comprising SYNGAP under conditions conducive to forming or maintaining synapses,
  b) contacting the cells with a candidate compound,
  c) analyzing the cells for an increase or decrease in the number of synapses; and
  d) detecting the increase or decrease as indicative of the compound useful in the diagnosis or treatment of the disorder relating to SYNGAP.

In another embodiment, the invention provides methods for detecting a compound capable of modulating a Ras-activated second messenger pathway. In this embodiment, the method includes at least one of the following steps:
  a) providing a Ras response system comprising a recombinant mammalian GTPase Activating Protein at Synapses (SYNGAP),
  b) contacting the Ras response system with a candidate compound,
  c) analyzing the Ras response system for an increase or decrease in Ras activity; and
  d) detecting the increase or decrease in the Ras activity as indicative of the compound capable of modulating the Ras-activated second messenger pathway.

In preferred embodiments, the Ras response system which includes at least one of Ras a nucleotide di- or tri-phosphate; adenylate cyclase; and an isolated polynucleotide encoding the SYNGAP or a fragment or a derivative thereof. The Ras response system can be provided by one or a combination different strategies including being provided in a host cell or a group of host cells (e.g., tissue or an organ), or a lysate of the cells, tissue or organ.

In another embodiment, the invention includes methods for detecting a compound capable of modulating a Ras-Raf (MAP kinase) cascade. The RAS-GTPase activating activity of SYNGAP can be measured using the MAP kinase as a reporter in a suitable primary or cultured cells. In this embodiment, the method includes at least one of the following steps:
  a) transfecting a cells with a reporter gene construct capable of being modulated by Ras-Raf (MAP kinase),
  b) transfecting the cells with a polynucleotide encoding any one of the SYNGAP sequences shown in SEQ ID Nos. 2, 4, or 6,
  c) contacting the cells with a candidate compound; and
  d) detecting the reporter gene construct as being indicative of the compound capable of modulating the Ras-GTPase activity of SYNGAP.

It will be appreciated that in some embodiments of the method, the SYNGAP cDNA can be provided before, during or after transfection of the reporter gene construct.

In another embodiment, the invention includes methods for detecting a compound capable of modulating a phospholipid-activated second messenger pathway. In this embodiment, the method includes at least one of the following steps:
  a) providing an inositol triphosphate response system comprising a recombinant SYNGAP,
  b) contacting the inositol triphosphate response system with a candidate compound,
  c) analyzing the inositol triphosphate response system for an increase or decrease in phospholipase activity; and
  d) detecting the increase or decrease in the phospholipase activity as indicative of the compound capable of modulating the phospholipid-activated second messenger pathway. In preferred embodiments, the phospholipase is a phosphoinositide-specific enzyme such as phospholipase C.

In one embodiment of the method, the inositol triphosphate response system further includes at least one of phosphatidylinositol (PI) and an isolated polynucleotide encoding the SYNGAP or a fragment or a derivative thereof. In a specific embodiment, the inositol triphosphate response system includes at least one of diacylglycerol, protein kinase C, and inositol 1,4,5 triphosphate ($INSP_3$). In a related embodiment, the phospholipid-activated second messenger pathway is capable of at least one of calcium ($Ca^{+2}$) release or protein phosphorylation. The inositol triphosphate response system can be provided by one or a combination different strategies including being provided in a host cell or a group of host cells (e.g., tissue or an organ), or a lysate of the cells, tissue or organ.

In another embodiment of the method, at least the pleckstrin (PH) homology of SYNGAP is provided for use with the inositol triphosphate response system. In another embodiment of the method, at least the PH homology and the SYNGAP C2 domain is used with the inositol triphosphate response system.

Additionally provided by the present invention are methods for detecting a compound capable of modulating phospholipid-dependent calcium ($Ca^{-2}$) binding to at least the SYNGAP C2 domain. In this embodiment, the method includes at least one of the following steps:
  a) mixing a phospholipid, calcium ($Ca^{+2}$) and at least the SYNGAP C2 domain, the mixing being under conditions conducive to forming a complex,
  b) contacting the mixture with a candidate compound,
  c) analyzing the mixture for formation of the complex; and
  d) detecting the complex as indicative of the compound capable of modulating the phospholipid-dependent binding between the calcium ($Ca^{+2}$) and at least the C2 domain of SYNGAP.

In another embodiment of the method, at least the PH homology and the SYNGAP C2 domain is used with the inositol triphosphate response system.

In embodiments of the present invention in which use of rat SYNGAP is desired, it will be possible to use a polypeptide sequence that includes and preferably consists of the sequence represented by any one of SEQ ID Nos: 2, 4 or 6.

Also contemplated are embodiments of the present invention which include use of a fragment or a derivative of the rat SYNGAP sequence as show in SEQ ID NOs: 2, 4, or 6.

The methods for detecting the compound capable of modulating the phospholipid-activated second messenger pathway are flexible and can be used if one or more components of the inositol triphosphate response system, e.g., PI, act "upstream" or "downstream" of SYNGAP.

In another embodiment of the present invention, there is provided methods for detecting a test amino acid sequence capable of binding a mammalian SYNGAP. In one embodiment, the method includes contacting the test amino acid sequence with the mammalian SYNGAP or a binding fragment or the derivative thereof under conditions conductive to forming a complex; and detecting the complex as indicative of the test amino acid sequence capable of binding the SYNGAP. For example, in a specific embodiment, the mammalian SYNGAP can be the rat SYNGAP sequence shown in SEQ ID NO: 6 or a suitable fragment or derivative thereof. Detection of the binding can be acomplished by one or a combination of different strategies such as at least one of immunoprecipitation, affinity chromatography, or a suitable biosensor assay.

In another embodiment of the method for detecting a test amino acid sequence capable of binding a mammalian SYNGAP, the contacting step can be performed in cells and the detecting step can include monitoring expression of a detectable gene product expressed by the cells In a preferred embodiment, the steps are performed in yeast cells.

Particulary preferred are those yeast cells (strains) that are suited for performing what is generally known in the field as a "two-hybrid" assay or a related term. In other embodiments, the detecting step of the methods can include screening a polypeptide expression library or a combinatorial peptide library, e.g., by a hybridization type assay using a suitable polynucleotide of this invention, for the test amino acid sequence.

In preferred instances, the methods for detecting the binding between the test amino acid sequence and the SYNGAP will typically register binding between at least one PDZ domain in the test amino acid sequence and a C-terminal sequence in the SYNGAP or fragment or derivative thereof. Preferably, the C-terminal sequence has the following general sequence: (T or S) XV; wherein X is an amino acid as defined below. The SYNGAP sequence used can be the rat SYNGAP sequence disclosed in SEQ ID NO: 2, 4, or 6 as well as suitable fragments or derivatives of that sequence.

Additionally provided are amino acid sequences detected by any of the methods for detecting the test amino acid sequence capable of binding a mammalian SYNGAP.

The present invention includes, in another aspect, methods for detecting excitatory synapses in a cell or group of cells. In one embodiment, the methods include contacting the cells or group of cells with an antibody or antigen-binding fragment of this invention under conditions sufficient to detect the excitatory synapses in the cells or group of cells. In a specific embodiment, the antibody or antigen-binding fragment is detectably-labeled or is capable of producing a detectable label. Illustrative of such labels include a radionuclide; a protein tag; a chromophore; a fluorescent, chemiluminescent or phosphorescent molecule. In another specific embodiment the antibody or antigen-binding fragment thereof is labeled with at least one enzyme capable of producing a chromophore, a fluorescent, chemiluminescent or phosphorescent molecule.

In another aspect, the present invention provides a library that includes a plurality of the polynucleotides or the polypeptides of this invention including fragments or derivatives of those polynucleotides or polypeptides. Illustrative of such libraries include cDNA and genomic DNA libraries, combinatorial and peptide expression libraries.

BRIEF DESCRIPTION OF THE DRAWINGS

FIGS. 1A–1E are drawings showing the nucleotide sequence of SYNAP-a coding (SEQ ID NO. 1) and non-coding (SEQ ID NO.22) strands. The predicted amino acid sequence is also shown (SEQ ID. NO. 3).

FIGS. 2A–2E are drawings showing the nucleotide sequence of SYNGAP-b coding (SEQ ID NO. 4) and non-coding (SEQ ID NO. 23) strands. The predicted amino acid sequence is also shown (SEQ ID. NO. 6).

FIGS. 3A–3E are drawings illustrating the nucleotide sequence of SYNGAP-c coding (SEQ ID NO. 7) and non-coding (SEQ ID NO. 24) strands. Also shown is the amino acid sequence (SEQ ID NO. 9) and an untranslated amino acid sequence (SEQ ID NO. 8A) following the C-terminus of the predicted SYNGAP-c protein.

FIG. 4A is a drawing showing the predicted amino acid sequence of SYNGAP-c (SEQ ID NO. 21).

FIG. 4B is a schematic drawing showing the domain organization of SYNGAP-c.

FIG. 4C is a drawing showing a sequence alignment between the Ras-GAP domain of SYNGAP-c (SEQ ID NO. 7), Rattus norvegicus (m) Ras-GAP (L13151; SEQ ID NO. 8) Homo sapiens neurofibromin (hs 1NF1, M38107; SEQ ID NO. 9). Identical residues are in bold type. Hyphens designate conceptual amino acid sequence deletions to maximize alignment.

FIG. 5 is a drawing showing a sequence alignment between the pleckstrin homology (PH) of SYNGAP-a (SEQ ID NO. 10), Homo sapiens p120 RasGAP (Hs p120 Genbank Accession No. P20936; SEQ ID NO. 11); D. melanogaster GAP1 (Dm GAP1 Genbank Accession No. P48423; SEQ ID NO. 12); and Homo sapiens pleckstrin (Hs Plec Genbank Accession No. P08567 SEQ ID NO. 10). Dots designate conceptual amino acid sequence deletions to maximize alignment.

FIG. 6 is a drawing showing a sequence alignment between the C2 domain of SYNGAP-a (SEQ ID NO. 14); Homo sapiens p120 RasGAP (Hs p120 Genbank 20 Accession No. P20936; SEQ ID NO. 15); Rattus norvegicus Synaptotagamin II (Genbank Accession No. P29101; SEQ ID NO. 16); and Bos taurus Rabphilin 3A (Genbank Accession No. A48097; SEQ ID NO. 17). Dots designate conceptual amino acid sequence deletions to maximize alignment.

DETAILED DESCRIPTION OF THE INVENTION

Figure 7A:
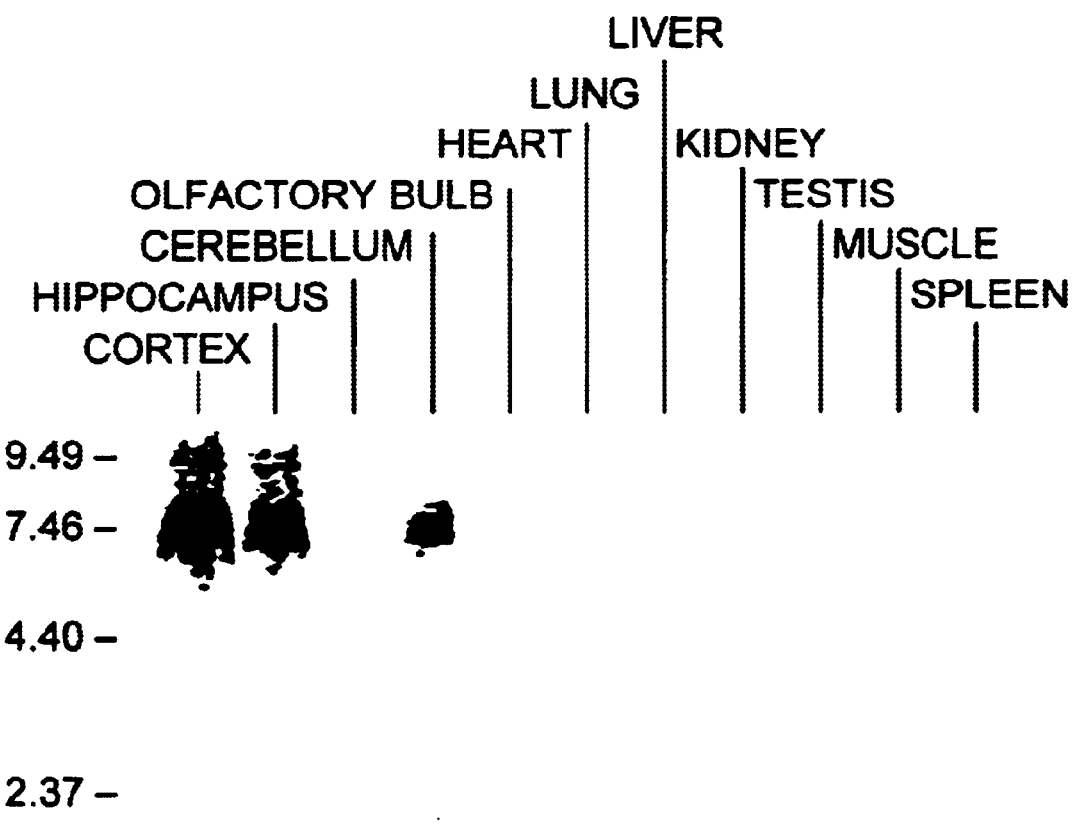
FIG. 7A is a representation of a Northern blot showing high level of SYNGAP mRNA expression in the brain.

As summarized above, the present invention features molecules that relate to mammalian SYNGAP and methods of using such molecules. Particularly provided are novel polynucleotides and polypeptides that can be used in the methods. Further provided are methods for isolating the molecules and using same to treat or prevent disorders relating to SYNGAP. Additionally provided are screening methods that can be employed to detect compounds with capacity to diagnose or treat disorders associated with SYNGAP.

In general, optimal practice of the present invention can be achieved by use of recognized manipulations such as those involving molecular, cell culture, biochemical and electrophysiological techniques. For example, techniques for and purifying nucleic acids, methods for making and screening cDNA libraries, methods for making recombinant vectors, cleaving DNA with restriction enzymes, ligating DNA, introducing DNA into host cells by stable or transient means, culturing the host cells, methods for isolating and purifying polypeptides, methods for making antibodies, methods for assaying signal transduction molecules, methods for detecting protein binding and particularly binding to PDZ and receptor domains, computer-assisted methods for detecting nucleic acid or amino acid sequence homologies, and electrophysiological techniques are generally known in the field. See generally Sambrook et al., *Molecular Cloning* (2d ed. 1989); Ausubel et al., *Current Protocols in Molecular Biology*, (1989) John Wiley & Sons, New York; S. Altschul et al. *Nuc. Acids Res.*, 25: 3389–3402 (1997); Marshall, C. J. Current Opin. in Cell Biol. (1996) 8: 197; Sheng, M. Neuron (1996) 17: 575 and references cited therein.

Unless otherwise indicated, reference to SYNGAP means a polynucleotide or amino acid sequence that is substantially homologous to at least one of SYNGAP-a, SYNGAP-b, or SYNGAP-c. Preferred use of the term SYNGAP means SYN GAP-a, SYNGAP-b or SYNGAP-c. As noted, SYNGAP-a, SYGAP-b, and SYNGAP-c are alternatively spliced variants. Sometimes SYNGAP-c will be specifically referred to herein as "GAPSYN".

Polynucleotides of this invention can be derived from a variety of sources such as a mammalian source and particularly a rodent or a primate source, e.g., rat, rabbit, mouse or human source. It will be appreciated that the present disclosure provides ample information to facilitate isolation of a variety of mammalian SYNGAPs through use of recognized molecular techniques such as the Polymerase Chain Reaction (PCR) amplification and related amplification techniques. Typically, the isolated polynucleotide will be positioned in a recombinant vector, although in some cases it may be desirable to provide the polynucleotide without a recombinant vector, e.g., as a PCR-amplified product. Particularly, the polynucleotide can be provided in a suitable DNA vector capable for expressing an encoded SYNGAP or a fragment or derivative thereof in a eukaryotic or prokaryotic cell expression system. The polynucleotide may include operably linked transcriptional elements such as a promoter, leader and optimal enhancer sequences to drive expression of the encoded polypeptide in a desired host cell expression system. Alternatively, the DNA vector itself may provide some or all of the control elements. In general, polynucleotides of the invention that encode SYNGAP including fragments and derivatives thereof, are often made so that naturally-occuring SYNGAP control sequences (e.g., genomic control sequences) are reduced in number and preferably removed.

As will be apparant from the preceeding discussion, the ability to detect and modulate SYNGAP in vitro and in vivo is very important. For example, inappropriate SYNGAP activity may negatively impact synaptic function, signal transduction or both. That inappropriate SYNGAP activity may arise from one or a combination of different causes such as a genetic deficiency, chronic illness, viral infection, bacterial infection, trauma (e.g., emotional or physical) and the like. In particular, relationship between synapse function, receptor function and signal transduction may be adversely affected by the inappropriate SYNGAP activity. Thus, the present methods are particularly useful for diagnosing and treating disorders arising from unsuitable SYNGAP activity.

By the term "SYNGAP activity" or like term is meant those functions attributed to SYNGAP as discussed herein, e.g, PDZ domain and rasGTPase inhibition. It will be appreciated that related activities can impact SYNGAP activity including synthesis of SYNGAP (transcription and translation), SYNGAP processing (e.g., protein maturation including modification such as glycosylation), protein stability in SYNGAP-expressing cells, and neuromodulation.

As discussed above, the present invention provides methods to detect mammalian SYNGAP in vitro or in vivo. Further provided are useful methods for modulating, including enhancing, expression or activity of SYNGAP in particular cells such as those that include chemical synapses with SYNGAP. By way of illustration, one can provide an anti-sense SYNGAP molecule to neurons to selectively inhibit SYNGAP activity in those neurons. In addition, a suitable SYNGAP antibody or antigen-binding fragment thereof can be provided to reduce or eliminate SYNGAP function. Further, compounds identified by the methods of this invention can be administered in vitro or in viva e.g., to enhance SYNGAP function including increasing the number or quality of chemical synapses that include SYNGAP.

In general, therapuetic methods of this invention include administration of a therapeutically effective amount of a SYNGAP or SYNGAP-related molecule to a subject and particularly a human patient in need of such treatment. Therapuetic methods of the invention also include administration of an effective amount of compound identified by this invention to the subject, in need of such treatment for an indication as disclosed herein.

Illustrative subjects for the purposes of this invention include those mammals suffering from or susceptible to those conditions generally discussed above, ie. disorders of the CNS and PNS such as an affective disorder, cognitive disorder, or a neurodegenerative disorder. In particular, a wide variety of CNS disorders may be alleviated by selectively enhancing or inhibiting SYNGAP activity in the CNS and particularly in the brain. As will be shown below, SYNGAP is predominantly expressed in the brain. Illustrative CNS disorders are affective disorders (e.g., depression), disorders of thought (e.g., schizophrenia) and degenerative disorders, as well as disorders manifested by application of anesthesia CNS disorders of severe impact include presenile dementia (sometimes referred to as Alzheimer's disease (AD) or early-onset Alzheimer's disease), senile dementia (dementia of the Alzheimer's type), Parkinson's disease (PD), and Huntington's disease (HD, sometimes referenced as Huntington's chorea). Such CNS disorders are well-represented in the human population. See generally; Gusella, J. F. et al. (1983) *Nature* 306: 234; Borlauer. W. and Jprmuloewoca. P. (eds.) (1976); *Adv. in Parkinsonism: Biochemistry, Physiology, Treatment. Fifth International Symposium on Parkinson's Disease* (Vienna) Basel: Roche; and references cited therein. Subjects that have suffered acute CNS trauma also may be treated in accordance with the invention, e.g. brain or spinal cord ischemia or trauma, stroke, heart attack or neorological deficits that may be associated with surgery.

In the methods of the invention, a desired therapuetic molecule (ie. a suitable SYNGAP or SYNGAP-related molecule or identified compound) can be administered to a subject in need of treatment or suspected of needing treatment in any of several ways. For example, a desired SYNGAP or SYNGAP-related polynucleotide, immune system molecule or a therapeutic compound can be administered as a prophylactic to prevent the onset of or reduce the severity of a targeted condition. Alternatively, the therapuetic molecule can be administered during or following the course of a targeted condition.

More specifically, the therapeutic molecule can be administered to a subject, either alone or in combination with one or more therapeutic agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, to particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain of the compounds.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly, e.g., by use of stents.

A therapeutic molecule of this invention can be employed in the present treatment methods as the sole active pharmaceutical agent or can be used in combination with other active ingredients, e.g., those compounds known in the field to be useful in the treatment of cognitive and neurological disorders.

The concentration of one or more treatment compounds in a therapeutic composition will vary depending upon a number of factors, including the dosage of the therapuetic compound to be administered, the chemical characteristics (e.g., hydrophobicity) of the composition employed, and the intended mode and route of administration. In general terms, one or more than one of the therapuetic compounds is compounds may be provided in an aqueous physiological buffer solution containing about 0.1 to 10% w/v of a compound for parenteral administration. As noted above, GAPYSN antibodies and antigen-binding fragments thereof can be modfied according to standard methods to deliver useful molecules or can be modified to include detectable labels and tags to facilitate visualization of synapses including SYNGAP.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day.

Therapuetic compounds identified by the present methods can be suitably administrated by conventional routes. For example, when the therapuetic compound is a synthetic or naturally-occuring chemical compound such as a drug, it will be preferred to administer the compound in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Current therapuetic practice typically utilizes one or a combination of different drugs to treat the disorders described above. As noted, the present invention provides methods for detecting compounds capable of treating or preventing the disorders. Compounds identified by these methods may be used either alone, or in combination with currently used therapies to alleviate the disorders or to reduce symptoms associated with the disorders. In particular, specific drugs that have been reported to be of use in the treatment of affective disorders, e.g., depression, manic-depressive disorders, anxiety disorders such as panic attacks and the like. Many of these drugs have been reported to work by modulating synaptic function, e.g., by altering receptor activity. According to methods of the present invention, compounds with capacity to modulate neuroreceptors, e.g., by increasing SYNGAP activity, may be similarly effective at treating depressive disorders. Such compounds may be identified by practice of the screening methods described herein.

Compounds identified by the methods of the invention can be further tested if desired in standard assays used to measure higher nervous system functions such as habituation, sensitization, learning and memory. Examples of such systems include those using well known test organisms such as Aplysia, *C elegans, D melanogaster*, primates such as monkeys, and rodents such as mice, rabbits and rats. Preferred compounds are those that can increase or decrease at least one of these functions by at least about 10%, 20%, 30%, 40%, 50%, 60%, 70%, 80%, 90% up to about 100% as determined by a suitable testing protocol recognized in the test organism selected.

Compounds identified by the present methods can be administered to a subject and preferably a human patient suffering from or suspected of suffering from a SYNGAP-related disorder as described above.

Particularly preferred systems for performing the testing methods of this invention involve cell culture assays and especially cell culture assays employing primary or cultured cells dervived from the nervous system. Preferred cultured cells are capable of expressing or express excitatory chemical synapses including SYNGAP such as CNS-derived cells such as those derived from the brain. Illustrative cells include are provided below in the examples. If desired, a cultured cell line can be tested for SYNGAP expression by determining if the cells express or can be made to express SYNGAP. Methods for detecting expression include immunological methods involving a suitable SYNGAP antibody, e.g., a Western blot, RIA, ELISA or other immunoassay.

In addition to the specific CNS- and PNS-related applications described herein, the present invention can also be used to therapeutically intervene in other systems that are affected by inappropriate SYNGAP activity. Such systems include the endocrine system for treatment of hormonal imbalances, the immune system for intervention in antigen processing, secreted immunomodulators, and viral processing, as well as anti-tumor applications, such as regulation of synapse formation in malignancies of the neuroendocrine system. To reduce or avoid CNS-or PNS-related side-effects, compounds identified in the methods of this invention may be re-screened multiple times, e.g., 2, 3, 4, or 5 times to identify compounds that specifically modulate SYNGAP in the neurons.

As discussed, the present invention provides isolated polynucleotides that encode SYNGAP or a fragment or a derivative of SYNGAP. The isolated polynucleotides may be cloned or subcloned using nearly any method known in the art. See e.g., Sambrook, J. et al., supra. In particular, nucleotide sequences of the invention may be cloned into any of a large variety of vectors. Possible vectors include, but are not limited to, cosmids, plasmids or modified viruses, although the vector system must be compatible with the host cell used. Viral vectors include, but are not limited to, lambda, simian virus, bovine papillomavirus, Epstein-Barr virus, and vaccinia virus. Viral vectors also include retroviral vectors, such as Amphatrophic Murine Retrovirus (see Miller et al., *Biotechniques*, 7:980–990 (1984)), incorporated herein by reference). Plasmids include, but are not limited to, pBR, pCMV5, PUC, pGEM (Promega), and Bluescript™ (Stratagene) plasmid derivatives. Introduction into and expression in host cells is done for example by, transformation, transfection, infection, electroporation, etc. See the examples which follow for particularly preferred recombinant vectors.

For preferred production of anti-sense RNA, use of specified recombinant vectors typically including strong bacterial or eukaryotic (e.g., viral) promoters will usually be desired. See e.g., Ausubel et al. supra.

The term "vector" or "recombinant vector" as used herein means any nucleic acid sequence of interest capable of being incorporated into a host cell and resulting in the expression of a nucleic acid sequence of interest. Vectors can include, e.g., linear nucleic acid sequences, plasmids, cosmids, phagemids, and extrachromosomal DNA. Specifically, the vector can be a recombinant DNA. Also used herein, the term "expression" or "gene expression", is meant to refer to the production of the protein product of the nucleic acid sequence of interest, including transcription of the DNA and translation of the RNA transcript. Most recombinant vectors will include a "cloning site" which as used herein is intended to encompass at least one restriction endonuclease site. Typically, multiple different restriction endonuclease sites (e.g., a polylinker) are contained within the vector to facilitate cloning.

As noted, preferred polynucleotides of this invention encode a mammalian SYNGAP having a molecular of between about 100, 110, 120, 130, 140, or about 150 kDA or greater. Also preferred are those polynucleotides that are at least 70%, 75%, 80%, 90%, 95%, 99% or greater sequence identity to any of the nucleotide sequences specifically shown in SEQ ID NOS: 1, 3, or 5. As will be fully appreciated, such sequences are substantially homologous to the sequences shown in SEQ ID NOS: 1, 3, or 5. A more preferred polynucleotide of the invention encodes the rat SYNGAP shown in SEQ ID NOS. 2, 4, or 6. A specifically preferred polynucleotide encodes the rat SYNGAP shown in SEQ ID NO. 6. See FIGS. 1A–1E; 2A–2E; and 3A–3E.

By the term "substantially homologous" is meant relationship between two nucleic acid molecules and generally refers to subunit sequence similarity between the two molecules. Typically, the two nucleic acid molecules will be DNA. When a subunit position in both of the DNA molecules is occupied by the same monomeric subunit, i.e. a nucleotide, then they are homologous at that position. Homology between the two sequences is a direct function of the number of matching or homologous positions, e.g., if 50% of the subunit positions in the two DNA sequences are homologous then the two sequences are 50% homologous. By "substantially homologous" is meant largely but not wholly homologous. More particularly, the term is meant to denote at least about 70% or greater homology as defined above with respect to the rat SYNGAP sequences illustrated in SEQ ID NOs. 1, 3, or 5. Preferred nucleotide sequences of the invention have at least about 75%, 80%, 85%, 90%, 95%, 97%, 98% or 99% homology as defined above with respect to the rat SYNGAP sequences illustrated in SEQ ID NOs: 1, 3, or 5.

The term "substantially homologous" is also used herein with reference to relationship between two polypeptide sequences and generally refers to subunit sequence similarity between the two molecules. When a subunit position in both of the polypeptides is occupied by the same monomeric subunit, i.e. an amino acid sometimes refered to as an amino acid residue, then they are homologous at that position. Homology between the two sequences is a direct function of the number of matching or homologous positions, eg., if 50% of the subunit positions in the two polypeptides are homologous then the two sequences are 50% homologous. By "substantially homologous" is meant largely but not wholly homologous. More particularly, the term is meant to denote at least about 70% or greater homology as defined above with respect to the rat SYNGAP sequences illustrated in SEQ ID NO: 2, 4 or 6. Preferred polypeptides of the invention have at least about 75%, 80%, 85%, 90%, 95%, 97%, 98% or 99% homology as defined above with respect to the rat SYNGAP sequences illustrated in SEQ ID NO: 2, 4, or 6.

Two substantially homologous polynucleotides can be identified by one or a combination of different strategies. For example, in one approach, a polynucleotide of this invention that is substantially homologous to any one of sequences shown in SEQ ID NOs: 1, 3, or 5, in addition to fragments and derivatives thereof of a length sufficient to bind to the sequences in the sequences, can be identified by employing moderately stringent conditions. In particular, moderate stringency conditions are meant to include a hybridization buffer comprising about 20% formamide in 0.8M saline/ 0.08M sodium citrate (SSC) buffer at a temperature of 37° C. and remaining bound when subject to washing once with that SSC buffer at 37° C. Additionally, highly stringent conditions are meant to include a hybridization buffer comprising about 50% formamide in SSC buffer at about 42° C. and remaining bound when washed in SSC buffer. See e.g., Sambrook et al. supra.

Additional methods of detecting and quantitating substantial homology refer to so-called "dry" methods and include use of publically available computer programs that can readily determine homology between nucleic acids of known or partially known sequence. Exemplary of such programs include the BLAST program available from the National Library of Medicine (Genbank). See also S. Altschul et al. *J. Mol. Biol.*, 215:403410 (1990); and S. Altschul et al. *Nuc. Acids Res.*, 25: 3389–3402 (1997) for specific disclosure relating to use of the BLAST program.

Nucleic acid fragments and derivatives of this invention preferably should comprise at least about 12 to about 50 nucleotides, at least about 60, 100 to 200 nucleotides, at least about 300, 400, to about 500 nucleotides, or at least about 1000, 1500, 2000, 2500, 3000, 3500 to about 4000 nucleotides or more. In some preferred embodiments, the nucleic acid fragment or derivative is bound to a suitable moiety, sometimes called a tag, which permits ready identification such as a radionucleotide, fluorescent or other chemical identifier.

The polynucleotide sequences of the invention can be altered by mutations such as substitutions, additions or deletions (contiguous or non-contiguous) that can provide for substantially homologous nucleic acid sequences. In particular, a given nucleotide sequence can be mutated in vitro or in vivo, to create variations in the nucleotides, e.g., to form new or additional restriction endonuclease sites or to destroy preexisting ones and thereby to facilitate further in vitro modification. Any technique for mutagenesis known in the an can be used including, but not limited to, in vitro site-directed mutagenesis (Hutchinson et al., *J. Biol. Chem.*, 253:6551 (1978)), use of TAB Registered TM linkers (Pharmacia), PCR-directed mutagenesis, and the like.

It will be appreciated that due to the degeneracy of genetic code, a number of different nucleic acid sequences may be used in the practice of the present invention. This includes the substitution of different codons encoding the same amino acid residue within the sequence, thus producing a silent or nearly silent change. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character. See generally Alberts et al., *Molecular Biology of the Cell*, (1989) Garland Publishing, New York.

Thus, the present invention includes polynucleotides with genetic alterations that do not substantially impact SYNGAP function as related herein. The genetic alterations can be synthetic, i.e., can be introduced experimentally, or may be naturally-occurring, e.g., in the form of SYNGAP isoforms or allelic variants. Additionally, SYNGAP-a, SYNGAP-b, and SYNGAP-c are illustrative of naturally-occuring splice variants. See FIGS. 1A–1E; 2A–2E; and 3A–3E.

As noted, the present invention provides oligonucleotide primers that are complementary to any of the nucleotide sequences shown in SEQ ID NOs: 1, 3, or 5. In most cases, the primers will be a DNA sequence of between about 12 to about 70 nucleotides in length preferably about 20, 30, 40, to about 50 or about 55 nucleotides in length. The oligonucleotide primers can suitably include restriction sites to add specific restriction enzyme cleavage sites to the PCR product as needed, e.g., to introduce a ligation site. Preferred DNA oligonucleotide primers are spaced from one another in opposing direction relative to extension of the primers. That is, the primers are spaced relative to each other on a polynucleotide template (usually on different strands) sufficient to produce an amplification product of at least about 50 nucleotides, at least about 60 to about 100 nucleotides, at least about 200 to 500 nucleotides, at least about 600 to 1000 nucleotides, or at least about 1000 to 3000 nucleotides up to about 4000 nucleotides as determined, e.g., by gel electrophoresis. Synthetic methods for making oligonucleotide primers are well known in the field. Exemplary primers are provided in the examples which follow.

Preferred polynucleotides of this invention are capable of modulating and preferably inhibiting Ras by at least 10%, 20%, 30%, 40%, 50%, 60%, 70%, 80%, 90%, up to about 100% in what has been referred to as a standard Ras GTPase assay. A variety of Ras GTPase assays are known in the field. For example, a preferred standard assay includes at least one of the following general steps:

a) mixing Ras or a GTPase- active portion of Ras with a suitable amount of detectably-labeled GTP (e.g., $\gamma^{32}P$-GTP), c) contacting the mixture with a mammalian SYNGAP, e.g., the amino acid sequence shown in SEQ ID NO: 2 or a fragment thereof including at least a Ras-GTPase active portion of the SYNGAP (ie., the GAP domain); and d) detecting binding of the detectably-labeled GTP to the Ras or Ras portion.

As will be shown below, the Ras and/or the SYNGAP protein can be fused (ie. covalently linked) to a suitable protein tag such as GST to facilitate protein isolation and purification. If desired, the above general method can be adapted to include a suitable control which can be a GST-fussion protein such as those known in the field. In general, the control is prepared and incubated under the same or closely related conditions as the assay but does not include addition of the SYNGAP or fragment thereof. A particularly preferred method for detecting Ras-GTPase activity involves measuring $\gamma$-$^{32}$P-GTP over a time period of between from about 30 seconds to about one hour or longer, typically from about 1 minute to about 20 minutes or longer. See Settleman et al. (1992) *Cell*. 69:539.

By the term "Ras-GTPase" portion of SYNGAP is meant at least the SYNGAP Ras-GTPase domain which domain is capable of negatively regulating Ras as determined by the standard Ras-GTPase assay described herein. Additional SYNGAP Ras-GTPase domains are those domains that are substantially homologous to the GAP domain shown between amino acid residues 266 and 502 of the rat SYN-GAP sequence. See FIG. 4C and SEQ ID No. 11. Preferred Ras-GTPase portions have a length of between about 200, 300 to about 400 amino acids and include amino acid residues (bold) shown in 4C (GAPSYN). The bolded amino acids shown in FIG. 4C will typically be present in the Ras-GTPase portion in the alignment shown.

By the term "pleckstrin homology" (P) is meant an amino acid sequence that is substantially homologous to any one of the following amino acid sequences: SynGAP-a, 162 to 243; SYNGAP-b, 60–141; and SYNGAP-c, 4 to 85. See FIGS. 1A–1E; 2A–2E; and 3A–3E; and 4A–B. Preferred PH domains have a length of between about 20, 30, 40, 30 50, 60, 70, 80, 90, to about 100 amino acids and include amino acid residues (bold) shown in FIG. 5 (SYNGAP-a). The bolded amino acids shown in FIG. 5 will typically be present in the PH domain in the alignment shown.

By the term "C2 domain" is meant an amino acid sequence that is capable of modulating phospholipid-dependent calcium ($Ca^{+2}$) binding to the SYNGAP as determined by assays disclosed herein. Preferred are those sequences which are substantially homologous to any one of the following amino acid sequences: SynGAP-a, 245 to 354; SYNGAP-b, 143 to 252; and SYNGAP-c, 87 to 196. See FIGS. 1A–1E; 2A–2E; 3A–3E and 4A–B. Additionally preferred C2 domains have a length of between about 90, 100, 120, 130, up to about 150 and include amino acid residues (bold) shown in FIG. 6 (SYNGAP-a). The bolded amino acids shown in FIG. 6 will typically be present in the PH domain in the alignment shown.

A variety of phospholipase C assays are known in the field which assays can be readily adapted in accord with the present invention. See e.g., James, S. R. et al., (1997) *Cell Signal*. 329; and Hurley, J. H. (1997) *Curr. Opin. Struct. Bio*. 7:557; and references cited therein.

The RasGTPase activating activity of SYNGAP can be measured by a variety of means including use of the MAP kinase cascade as a reporter in a primary or immortalized cell culture, e.g., hippocampal neurons or HEK 293, NIH3T3 cells. The regulation of Ras activity by SYNGAP in a selected cell or cell line can be observed by transfecting the cells with a SYNGAP cDNA plasmid with, e.g., a luciferase or other suitable reporter construct that is activated by the MAP kinase cascade. See e.g., 1997 instruction manual entitled *PathDetect™ In Vivo Signal Transduction Pathway Trans-Reporting Systems*, pp. 1–20 (Stratagene Cloning Systems, La Jolla, Calif.). Alternatively, SYNGAP cDNA can be transfected into primary culture cells with the reporter construct. SYNGAP activity can then be indirectly assayed by quantifying luciferase (or other reporter activity) with a luminometer or other suitable measuring device. Various agents, e.g., drugs, that regulate SYNGAP activity of the pathway can be rapidly screened by this method. For example, a variety of drugs such as growth factors, cytokines, neurotransmitters and the like can be tested for capacity to regulate SYNGAP. Importantly, agents that activate or inhibit SYNGAP activity can be rapidly analyzed.

Additionally preferred polynucleotides of this invention encode a mammalian SYNGAP or SYNGAP-related amino acid sequence that is capable of binding 1, 2, 3, up to about 10 PDZ domains as determined by a standard PDZ domain binding assay. For example, a prefered standard PDZ domain binding assay involves what has been referred to as the yeast two-hybrid system.

In general, the yeast GAL4 two hybrid system can detect protein-protein interactions based on the reconstitution of function of GAL4 (yeast transcriptional activator) by activation of a GAL1-lacZ reporter gene. Like several many other transcription activating factors, the GAL4 protein contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, UAS[G]). Several examples of yeast two-hybrid assays have been reported. See e.g., U.S. Pat. Nos. 5,693,476 and 5,695,941.

A two hybrid system such as is described above may be used to identify proteins and particularly synaptic proteins that include at least one suitable SYNGAP-binding PDZ domain. As noted above and more specifically in the following discussion, that interaction is believed to occur due to binding between the PDZ domain and the C-terminal sequence ((T or S), X V) at the end of SYNGAP wherein X is any of the 20 common amino acids (Ala, Arg, Asn, Asp, Lys, Gln, Glu, Gly, His, Ile, Lev, lys, Met, Phe, Pro, Ser, Thr, Trp, Tyr, Val). A specific PDZ binding assay involves at least one of the following steps:

a) fusing a polynucleotide encoding SYNGAP or a suitable fragment thereof to the GAL4 DNA binding domain (G4BD) (fusion protein) in a suitable yeast expression vector, b) transforming the vector carrying fusion protein into yeast cells harboring a suitable reporter gene activated by GAL4 (e.g., a suitable LacZ construct), c) transforming the cells with a second vector carrying a fusion between a polypeptide comprising at least one PDZ domain (e.g, PSD-95/SAP90) and the transcription activating domain of yeast GAL4; and d) screening the transformants for expression of the reporter gene in the yeast.

In most cases, the yeast transformants are screened using a beta-galactosidase (beta-gal) assay on plates containing the chromogenic substrate X-gal. Reporter-expressing cells can be selected, cloned, and analyzed if desired. It may be of interest in some instances to use a second two hybrid system, described in detail in Ausubel, et al., that utilizes a native *E. coli* LexA repressor protein. That protein binds tightly to appropriate operators. A plasmid is used to express one of a pair of interacting proteins (the "bait" protein) as a fusion to LexA. Example 2 below descibes an especially preferred assay for detecting PDZ binding to SYNGAP using a yeast two-hybrid system.

Preferred polynucleotides are capable of encoding sequence that result in at least about a 10% to 20% up to about a 100% increase or more of positive (blue) colonies relative to a suitable control. Colony number can be determined by inspection.

Additional standard assays can be conducted to detect PDZ binding to SYNGAP and SYNGAP-related polypeptides of this invention. For example, specific biochemical assays are useful for detecting PDZ interactions including certain partner assays. For example, a polynucleotide can be expressed and the encoded polypeptide immobilized on a suitable solid support. A suitable PDZ protein such as PSD-95/SAP90 or a fragment or a derivative thereof is contacted to the solid support under conditions conducive to binding between the PDZ protein and the SYNGAP or SYNGAP-related polypeptide . Typically, the PDZ protein will be detectably-labeled, e.g., with a radionuclide or other suitably detectable tag to facilitate detection and quantitation, if desired, of the binding. Preferred methods for detecting the binding include well known panning methods, e.g., immunopanning, preferably conducted in multi-well plates. Alternatively, the binding can be assayed by conventional immunological techniques such as RIA, ELISA, affinity chromatography, Western blots, etc. Preferred polynucleotides are capable of encoding polypeptides that exhibit and increase in binding to the PDZ protein of at least about 20%, 300%, 40%, 50%, 60%, 70%, 80%, 90%, up to 100% or more relative to a suitable control polypeptide that does not include a detectable PDZ domain (e.g, LacZ).

Additionally preferred polynucleotides of this invention are capable of encoding polypeptides that bind PDZ domains as detected by use of affinity biosensor methods. Such methods may be based on a variety of detectable effects including surface plasmon resonance (SPR). SPR is particular advantageous for monitoring molecular interactions in real-time, enabling a sensitive and comprehensive analysis of the effects of test compounds on the binding interactions between two proteins than the methods discussed above. Preferred polynucleotides of this invention are capable of encoding polypeptides that are capable of binding proteins comprising at least one PDZ domain and causing a change in reflectance intensity of at least about 10% to about 20% relative to a suitable control protein (e.g., LacZ). See e.g., Cullen, D. C., et al., *Biosensors* 3:211–225 (1988).

The above-mentioned methods can be readily adapted to detect compounds that can modulate SYNGAP activity, e.g., by modulating SYNGAP binding to a polypeptide comprising one or more PDZ domains, modulating SYNGAP-mediated Ras GTPase activity, or both. In general, any of the methods can be optimized to include addition of one or more test compounds optionally in parallel with a suitable control, to detect modulation.

A variety of different compounds may be screened using methods of the present invention. They include peptides, macromolecules, small molecules, chemical and/or biological mixtures, and fungal, bacterial, or plant extracts. Such compounds, or molecules, may be either biological, synthetic organic, or even inorganic compounds, and may be obtained from a number of sources, including commercial or publically-accessible vendors of libraries of compounds.

In cases where an identified compound is a peptide, the peptide may be utilized to aid in the discovery of small molecule mimetics. Methods of the present invention are well suited for screening libraries of compounds in multi-well plates (e.g., 96-well plates), with a different test compound in each well. In particular, the methods may be employed with combinatorial libraries. A variety of combinatorial libraries of random-sequence oligonucleotides, polypeptides, or synthetic oligomers have been proposed including small-molecule libraries. Alternatively, the library may be formed by solid-phase synthetic methods in which beads containing different-sequence oligomers that form the library are alternately mixed and separated, with one of a selected number of subunits being added to each group of separated beads at each step. The identity of library compounds with desired effects on the binding of an SYNGAP and a protein comprising one or more PDZ domains such as PSD-95/SAP90 can be determined by any of the methods described herein. See e.g., Houghten, R. A., (1985) *PNAS (USA)* 85:5131.

As noted, particularly preferred polynucleotides of this invention exhibit a length of between about 50 to about 100 nucleotides, about 200, 300, 400, 500, 600, 800, 1000, 1500, 2000, 2500, 3000, 3500, 4000 or more as determined by standard nucleic acid sizing techniques such as agarose or polyacrylamide gel electrophoresis. The polynucleotide can be RNA, DNA or a chimera thereof as desired.

Exemplary host cells which can express the isolated polynucleotides of this invention are known in the field and include bacterial cells (e.g., *E. coli*) such as MM294, DM52, XL1-blue (Stratagene) strains of *E. coli*, and animal cells (e.g., CV-1 and COS-7 cells). In addition, it is possible to express certain isolated nucleic acids of the invention in certain yeast cells (e.g., *S. cerevisiae*), amphibian cells (e.g., *Xenopus oocyte*), and insect cells (e.g., *Spodoptera frugiperda* and *Trichoplusia ni*). Methods for expressing isolated and recombinant DNA in these cells are known. See e.g., Sambrook et al., *Molecular Cloning* (2d ed. 1989), Ausubel et al. supra, and Summer and Smith, *A Manual of Methods for Baculovirus Vectors and Insect Cell Culture Procedures*: Texas Agricultural Experimental Station Bulletin No. 1555, College Station Texas (1988). Specifically preferred host cells are discussed more fully below.

The polynucleotides of this invention can be readily made by techniques well known in the field including those techniques involving large-scale production thereof such as those including use of roller bottles, bioreactors and the like.

The term "complementary" or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99 to about 100%. Complementary polynucleotide sequences can be identified by a variety of approaches including use of well-known computer algorithms and software.

Polynucleotides of this invention are typically isolated, meaning that the polynucleotides usually constitute at least about 0.5%, preferably at least about 2%, and more preferably at least about 5% by weight of total polynucleotide present in a given fraction. A partially pure polynucleotide constitutes at least about 10%, preferably at least about 30%, and more preferably at least about 60% by weight of total nucleic acid present in a given fraction. A pure polynucleotide constitutes at least about 80%, preferably at least about 90%, and more preferably at least about 95% by weight of total polynucleotide present in a given fraction. Purity can be determined by standard methods including gel electrophoresis.

It is preferred that the polypeptides of the present invention be substantially pure. That is, the polypeptides have been isolated from cell substituents that naturally accompany it so that the polypeptides are present preferably in at least 80% or 90% to 95% homogeneity (w/w). Polypeptides having at least 98 to 99% homogeneity (w/w) are most preferred for many pharmaceutical, clinical and research applications. Once substantially purified the polypeptide should be substantially free of contaminants for therapeutic applications. Once purified partially or to substantial purity, the polypeptides can be used therapeutically, or in performing a desired assay. Substantial purity can be determined by a variety of standard techniques such as chromatography and gel electrophoresis.

Particularly preferred polynucleotides and polypeptides of this invention are provided as substantially sterile formulations.

As noted, illustrative polynucleotides of this invention include those encoding a mammalian SYNGAP as identified herein. Preferably the polynucleotides are at least substantially homologous to any of the sequences shown in SEQ ID NOs: 2, 4, or 6. For example, the mammalian SYNGAP can be derived from a primate such as a monkey or a human; or the mammalian SYNGAP can be derived from a rodent such as a rat, mouse, guinea pig, or rabbit. By the term "derived from" is meant that at least a portion of the polynucleotide was isolated from or copied from a naturally-occuring mammalian nucleic acid such as a genomic DNA or cDNA.

The SYNGAP and SYNGAP-related polypeptides of the present invention can be separated and purified by appropriate combination of known techniques. These methods include, for example, methods utilizing solubility such as salt precipitation and solvent precipitation, methods utilizing the difference in molecular weight such as dialysis, ultrafiltration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the polypeptides of this invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

Preferred polypeptides of this invention generally exhibit a molecular weight from about 100, 110, 120, 130, 140, to about 150 kDa as determined by standard protein sizing manipulations such as polyacrylamide gel electrophoresis and centrifugation sedimentation. Additionally preferred are those polypeptides that are substantially homologous to the SYNGAP sequence shown in SEQ ID NO: 6 (ie. at least 70%, 80%, 90%, 95% up to about 99% homologous) as determined by the methods described earlier. Particularly preferred are those polypeptides having from between about 200, 300, 400, 500, 600, 700, 800, 900, 1000, 1100, up to about 1500 amino acids.

The term "amino acid sequence" as used herein generally refers to any polymer preferably consisting essentially of any of the 20 naturally occurring amino acids regardless of its size. Although the term "protein" is often used in reference to relatively large proteins, and "polypeptide" or "peptide" is often used in reference to small amino acid sequences, use of these terms in this field often overlaps. Thus, it will be understood that the term generally refers to proteins, polypeptides, and peptides unless otherwise noted.

As noted, the present invention provides a variety of methods for detecting a Ras-activated signaling pathway or a phospholipid-activated pathway (sometimes called a Ras-activated or a phospholipid-activated second messenger pathway, respectively). Additionally, the present methods provide means of detecting modulation of Ras-Raf (MAP kinase) cascades. In preferred embodiments the methods include a Ras- or inositol triphosphate response system which systems can be provided in a suitable host cell or cell lysate.

In general, the response systems can be obtained by coupling a mammalian SYNGAP or a suitable fragment thereof encoded by an isolated cDNA molecule to an appropriate second messenger response system. Particular SYN-GAP fragments of interest include those that modulate Ras activity or include the C2 domain as disclosed herein. The system can include but is not limited to systems relating to adenylate cyclase, phosphoinositide hydrolysis, guanylate cylase, MAP kinase, and certain synaptic receptor proteins such as the NMDA receptor. One way to obtain a suitable response system is by transfection of an appropriate isolated polynucleotide of this invention into a suitable host cell that includes the desired second messenger system. Alternatively, a lysate can be prepared from the cell that includes purified or partially purifed molecules in the pathway. When cells are used, the cells can be obtained from pre-existing cell lines or can be generated by inserting suitable components of the desired second messenger system into those existing cell lines. Such a transfection system will preferably provide, in a single cell line, a complete Ras- or inositol triphosphate response system for detection of componds capable of modulating the desired signalin pathway.

As noted, the present also embraces immune system molecules and particularly antibodies and antigen-binding fragments thereof that binding mammalian SYNGAP and particularly the SYNGAP sequence shown in SEQ ID NO: 2.

In particular, antibodies of the invention can be prepared by techniques generally known in the art, and are typically generated to a purified sample of SYNGAP, SYNGAP-related polypeptide. The antibodies also can be generated from an immunogenic peptide that comprises one or more epitopes of SYNGAP. Examples of such immunogenic peptides are described more fully below in the examples. As discussed above, monoclonal antibodies are sometimes preferred, although polyclonal antibodies also can be employed.

More particularly, antibodies can be prepared by immunizing a mammal with a purified SYNGAP or preferably an immunogenic peptide thereof such as those peptides specifically described below. The SYNGAP or SYNGAP peptide can be administered to the mammal alone or complexed with a carrier. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. The optimal immunizing interval, immunizing dose, etc. can vary within relatively wide ranges and can be determined empirically based on this disclosure. Typical procedures involve injection of the antigen several times over a number of months. Antibodies are collected from serum of the immunized animal by standard techniques and screened to find antibodies specific for the SYNGAP. Monoclonal antibodies can be produced in cells which produce antibodies and those cells used to generate monoclonal antibodies by using standard fusion techniques for forming hybridoma cells. See G. Kohler, et al., *Nature*, 256:456 (1975). Typically this involves fusing an antibody producing cell with an immortal cell line such as a myeloma cell to produce the hybrid cell. Alternatively, monoclonal antibodies can be produced from cells by the method of Huse, et al., *Science*, 256:1275 (1989).

One suitable protocol provides for intraperitoneal immunization of a mouse with a composition comprising purified immunogenic SYNGAP peptide such as those specifically disclosed below conducted over a period of about two to seven months. Spleen cells then can be removed from the immunized mouse. Sera from the immunized mouse is assayed for titers of antibodies specific for the immunogenic SYNGAP peptide prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT) or thymidine kinase deficiency (TK$^-$). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See G. Kohler, et al., *Nature*, supra. The thus cloned hybridoma is grown in a culture medium, e.g. RPMI-1640. See G. E. More, et al., *Journal of American Medical Association*, 199:549 (1967). Hybridomas, grown after the fusion procedure, are screened such as by radioimmunoassay or enzyme immunoassay for secretion of antibodies that bind specifically to the purified SYNGAP or the immunogenic SYNGAP polypeptide. Preferably an ELISA is employed for the screen. Hybridomas that show positive results upon such screening can be expanded and cloned by limiting dilution method. Further screens are preferably performed to select antibodies that can bind to SYNGAP or the immunogenic SYNGAP peptide in solution as well as in a mammalian fluid sample such as those obtained from a human. The isolated antibodies can be further purified by any suitable immunological technique including affinity chromatography.

For human therapeutic applications, it may be desirable to produce chimeric antibody derivatives, e.g. antibody molecules that combine a non-human animal variable region and a human constant region, to thereby render the antibodies less immunogenic in a human subject than the corresponding non-chimeric antibody. A variety of types of such chimeric antibodies can be prepared, including e.g. by producing human variable region chimeras, in which parts of the variable regions, especially conserved regions of the antigen-binding domain, are of human origin and only the hypervariable regions are of non-human origin. See also discussions of humanized chimeric antibodies and methods of producing same in S. L. Morrison, *Science*, 229:1202–1207 (1985); Oi et al., *BioTechniques*, 4:214 (1986); Teng et al., *Proc. Natl. Acad. Sci. U.S.A.*, 80:7308–7312 (1983); Kozbor et al., *Immunology Today*, 4:7279 (9183); Olsson et al., *Meth. Enzymol.*, 9:3–16 (1982). Additionally, transgenic mice can be employed. For example, transgenic mice carrying human antibody repertoires have been created which can be immunized with SYNGAP or the immunogenic SYNGAP peptide. Splenocytes from such immunized transgenic mice can then be used to create hybridomas that secrete human monoclonal antibodies that specifically react with the SYNGAP or immunogenic SYNGAP peptide. See N. Lonberg et al., *Nature*, 368:856–859 (1994); L. L. Green et al., *Nature Genet.*, 7:13–21 (1994); S. L. Morrison, *Proc. Natl. Acad. Sci. U.S.A.*, 81:6851–6855 (1994).

As described previously, an antibody of this invention (polyclonal or monoclonal) or antigen-binding fragment thereof can be specifically bound to SYNGAP, e.g., in an excitatory chemical synapse. Thus, a pharmaceutical composition containing the antibody and particularly a monoclonal antibody in a pharmaceutically acceptable carrier or diluent is useful for the detection or diagnosis of cells comprising SYNGAP, e.g., neurons and other cells which may use SYNGAP as a marker such as tumors derived from neurons.

To faciliate detection or diagnosis, the desired antibody will usually be detectably-labeled. A wide spectrum of labels are known in the field such as those that can be readily detected following administration to a subject and particularly a human patient. However, a radioisotope can be desirably used as a label because such labels are usually well suited to use in diagnostic imaging, especially those methods using scintigraphy or related methods. Choice of label will depend on several parameters the half-life or particle desired and the purpose of the detection or diagnosis. In many cases, it will be useful to choice a radionuclide that can be stored in a target tissue such as $^{99}$Tc and other suitable radionuclides.

For in vivo administration, nearly any kind of carrier or diluent, preferably a pharmaceutically acceptable carrier or diluent is acceptable and can be used for preparation of the pharmaceutical composition of the present invention. It is also possible to use a plurality of carriers or diluents in combination. It is desirable to use a sterile and aqueous isotonic suspension or solution including, for example, a physiological saline and a phosphate buffer physiological saline. The pharmaceutical composition of the present invention can be administered by non-oral administration such as subcutaneous administration, intramuscular administration, intravenous administration, intraperitoneal administration, or other routes as discussed above. Preferred amounts of the pharmaceutical composition to be administered include those specific amounts discussed above.

Additionally, suitably labelled antibodies and antigen-binding fragments that bind SYNGAP or SYNGAP-related molecules can be used in vito, e.g., in tissue culture, to detect excitatory chemical synapses in developing or established neuronal cell cultures. In this example, the antibody can be detectably-labeled with a variety of labels known in the field.

By the term "specific binding" or similar term is meant a molecule disclosed herein which binds another molecule, thereby forming a specific binding pair, but which does not recognize and bind to other molecules as determined by, e.g., Western blotting, ELISA, RIA, gel mobility shift assay, enzyme immunoassay, competitive assays, saturation assays or other suitable protein binding assays known in the field.

As specifically shown in the examples which follow, we have isolated a novel Ras-GTPase activating protein called SYNGAP. The SYNGAP protein specifically interacts with the PDZ domains of PSD-95 and SAP102 in vitro and in vivo. SYNGAP is selectively expressed in brain and is highly enriched at excitatory synapses where it is present in a large macromolecular complex with PSD-95 and the NMDA receptor. SYNGAP stimulates the GTPase activity of Ras suggesting that it negatively regulates Ras activity at excitatory synapses. Ras signaling at the postsynaptic membrane may be involved in the modulation of excitatory synaptic transmission by NMDA receptors and neurotrophins. These results indicate that SYNGAP may play an important role in the modulation of synaptic plasticity.

In particular, the examples below show that SYNGAP is a brain-specific protein of about 125 kDa that is associated in a large complex with PSD-95/SAP90, SAP102, and the NMDA receptor in brain. Immunocytochemical studies show that SYNGAP is highly enriched at excitatory synapses and colocalizes with PSD-95/SAP90, SAP102, and the NMDA receptor. The GTPase activating domain shares significant homology with other rasGAPs and has rasGAP activity. These results suggest that the PSD-95/SAP90 family, through SYNGAP, may play a role in the regulation of synaptic ras signal transduction cascades.

The following non-limiting examples are illustrative of the present invention.

The following Examples 1–8 refer to the isolation and characterization of SYNGAP-c (GAPSYN) unless otherwise specified

EXAMPLE 1

Molecular Characterization of SYNGAP

Novel proteins that interact with the PDZ domains of the PSD-95/SAP90 family of proteins were identified by using the third PDZ domain of SAP102 to screen a yeast two-hybrid hippocampal cDNA library (Fields, S. and Song, O. (1989) Nature. 340:245; Dong, H., et al., (1997) Nature. 386:279). Screening two million clones led to the isolation of a single clone with an open reading frame of 168 amino acids. Successive screening of a λZAP hippocampal cDNA library yielded several full length cDNAs with insert sizes of ~7.4 kb. The full length cDNA had an open reading frame encoding 1135 amino acids with a calculated molecular weight of 124.7 kDa. See FIGS. 3A–D; and FIGS. 4A–B.

Analysis of the amino acid sequence of the protein indicates that it is novel and contains several functional domains (FIG. 4B). The amino terminal half of the protein includes a region that has some homology to PH (pleckstrin homology) domains, a C2 domain that may be involved in the binding of $C^{2+}$ and phospholipid, and a rasGAP domain. The C-terminal half includes a repeat of 10 histidines which may be involved in metal chelation, several potential serine and tyrosine phosphorylation sites and a T/SXV motif (QTRV) required for the interaction with SAP102 and PSD-95 (see below). The amino acid sequence also predicts that it is a cytosolic protein that has no apparent transmembrane region and no signal peptide. Alignment of the GAP domain of SYNGAP with other ras-GAPs (FIG. 1C) indicates that the amino acids are critical for the interaction of rasGAPs with Ras and the stimulation of Ras GTPase activity are conserved (Scheffzek, K., et al. (1997) Science, 277:333). Because of its ras-GTPase activity and selective localization at excitatory synapses (see below), this protein was named SYNGAP.

FIGS. 4A–C are more particularly described as follows: FIG. 4A: amino acid sequence of SYNGAP (SEQ ID NO. 21). SYNGAP is a 1135 amino acid protein that contains a ras-GAP domain (shaded) and several regulatory domains. Consensus serine and tyrosine phosphorylation sites are underlined. FIG. 4B: In addition to the ras-GAP domain (GAP) the structure of SYNGAP includes a domain that shares a partial homology to PH domains (PH) followed by a C2 domain (C2). The C-terminal four amino acids (QTRV) required for binding to PDZ domains are indicated. FIG. 4C: alignment of the ras-GAP domain of SYNGAP with Rattus norvegicus (rn) ras-GAP (L13151) and Homo sapiens neurofibromin (hs 1NF1, M38107). Identical residues are in bold type. The residues that participate in catalysis (*) and in the interaction with Ras (+) are indicated.

1. Identification and Cloning of SYNCAP

The yeast two-hybrid system was utilized to find protein(s) that interact with the third PDZ domain of SAP102. The third PDZ domain (amino acids 367 to 452) was generated by PCR using a pair of oligonucleotides with restriction digestion sites for SalI and BglII sense (5'-ACGCGTCGACCAGAGAGCCCCGCAAG-3' (SEQ ID NO. 18)) and antisense (5'-GAAGATCAGGTCTATAC GGGCCAC-3' (SEQ ID NO. 19)) and was subcloned into the pPC97 yeast vector containing the GAL4 DNA binding domain (Chevray, P. M., and Nathans, D. (1992) Proc. Natl. Acad. Sci. USA. 89:5789). The bait plasmid was then transformed into Y190 yeast cells (Durfee, T., et al. (1993) Genes Dev. 7:555; Staudinger. J., et al. (1995) J. Cell Biol. 128:263) and a two-hybrid screening was performed using a random-primed cDNA library from rat hippocampus subcloned into the SalI/NotI site of the pPC86 vector containing the GAL 4 transcription activation domain (Brakeman, P. R., et al. (1997) Nature. 386:284; Dong et al., supra). Positive clones were selected on plates lacking leucine, tryptophan, and histidine with 50 mM 3-aminotriazole and confirmed by filter assay for β-galactosidase activity (Breeden, L., and Nasmyth, K. (1985) Cold Spring Harb. Symp. Quant. Biol. 50; 643). For cloning of the full length of SYNGAP, successive rounds of phage library screening were performed with rat hippocampal λZAP cDNA libraries (dT-primed and random-primed). The nucleic acid sequence of the SAP102 protein can be found in Mueller, et al. (1996) Neuron. 17:255. The hippocanpal λZAP cDNA library was made according to standard methods. See e.g., Ausubel et al. supra and Sanbrook et al., supra.

1. Transfection of HEK 293T Cells

SYNGAP subcloned into pGW-1 mammalian expression vector (10 μg) was transfected into HEK 293T cells in 10 cm culture dishes by calcium phosphate co-precipitation (Blackstone, C. D., et. al. (1992) J. Neurochem. 58:1118). After 48 hours of transfection the cells were harvested and analyzed by SDS-PAGE and immunoblotting.

EXAMPLE 2

Interaction of SYNGAP and PDZ Domains Inside Cells

The interaction of SYNGAP with the PDZ domains of PSD-95/SAP90 and SAP102 was further studied in the yeast two-hybrid system. As shown in Table 1 below, SYNGAP interacts with all of the PDZ domains of PSD-95/SAP90. Deletion analysis of SYNGAP's C-terminus revealed that the C-terminal-TRV is critical for binding of SYNGAP to the PDZ domains (Table 1). In addition, the last valine residue is essential for interaction, as has been shown with other ligands for the PSD95/SAP90 family of proteins.

1. Yeast Interaction Studies

The yeast two-hybrid system was used to check for interaction of the carboxy terminal tail of SYNGAP with the various PDZ domains of SAP102 and PSD-95/SAP90. The PDZ domains of PSD-95/SAP90 and SAP102 were amplified by PCR and subcloned into the yeast vector, pPC 86. PDZ domain 1 of PSD-95 covers the amino acids from 40 to 160; PDZ domain 2, from 156 to 248; and PDZ domain 3, from 298 to 403. See e.g., Cho et al., (1992) Neuron 9:929 for disclosure relating to the PSD-95 sequence.

The original yeast clone with the intact C-terminal tail of SYNGAP (968–1136) was subcloned into pPC97 and was used to check for interaction with the various PDZ domains. The requirement of the C-terminal T/SXV motif was investigated by subcloning PCR generated deletion mutants of SYNGAP (894 to 1134 for -QTR* and 894 to 1132 for -Q*) The yeast vectors are transformed into Y190 and scored by growth without leucine, tryptophan, and histidine, in 100 mM 3-aminotriazole and filter assay for β-galactosidase activity.

TABLE 1

PDZ Domain Interaction with the Carboxy Terminal Tail Motif, -QTRV, of SYNGAP

| | (-QTRV*) | | (-QTR*) | | (-Q*) | |
|---|---|---|---|---|---|---|
| | HIS3 | B-Gal | HIS3 | B-Gal | HIS3 | B-Gal |
| SAP102 | | | | | | |
| PDZ 3 | + | + | − | − | − | − |
| PSD-95 | | | | | | |
| PDZ 1 | + | + | | | | |
| PDZ 2 | + | + | | | | |
| PDZ 3 | + | + | | | | |

EXAMPLE 3

Brain-specific Expression of SYNGAP mRNA and Protein

Figure 7B:
FIG. 7B is a representation of a Western blot showing SYNGAP in rat tissues using immunoblot techniques. These antibodies recognized a 130 kDa protein in HEK293T cells transfected with the SYNGAP cDNA (Lane 2) and in rat brain homogenates (Lane 3). The 130 kDa protein was not detected in mock transfected HEK293T cells (lane 1) and immunorecognition of the 130 kDa protein in brain was blocked by preabsorbtion of the antibody with the antigen (Lane 4).
Figure 7C:
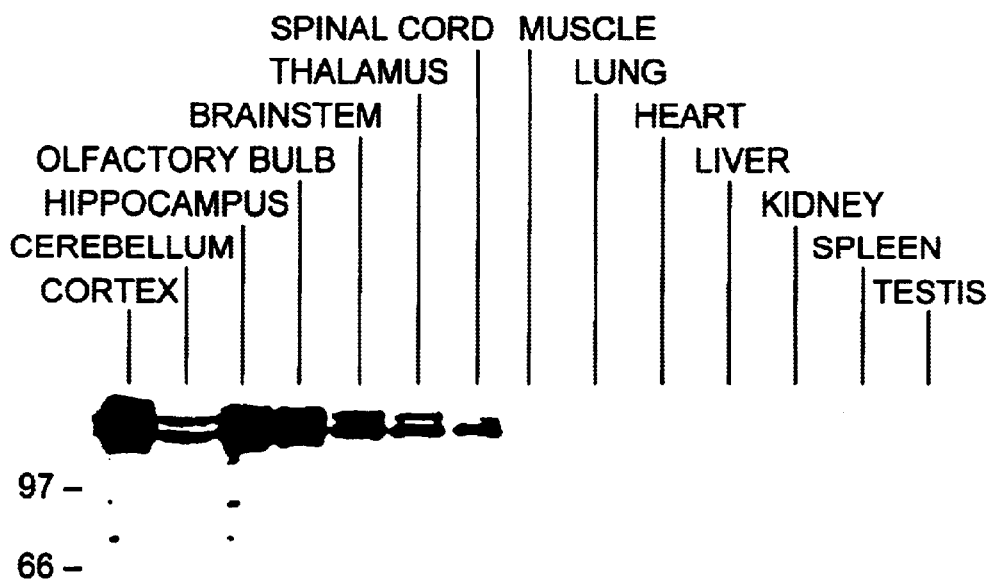
FIG. 7C is a representation of a Western blot showing SYNGAP in rat tissues using the SYNGAP antibody. Expression of the SYNGAP protein is brain specific.

Northern blotting with the SalI/NotI fragment of the yeast clone revealed a mRNA of approximately 7 kb which was detected only in brain and was expressed predominantly in cortex, hippocampus, and olfactory bulb (FIG. 7A). In addition, a less abundant mRNA of about 9 kb was observed in these same tissues. To characterize the SYNGAP protein, an anti-SYNGAP antibody was generated against its last C-terminal amino acids (FIG. 7B). The anti-SYNGAP C-terminal antibody specifically recognized 130 kDa SYNGAP protein when it was expressed in HEK 293 cells. In brain, the anti-SYNGAP antibody recognized a doublet or triplet of proteins at 130 kDa (FIG. 7C). Preabsorption of the anti-SYNGAP antibody with the peptide immunogen completely eliminated the recognition of the 130 kDa protein confirming the specificity of the antibody. The origin of the triplet in brain is not entirely understood. Without wishing to be bound to any specific theory, the triplet may arise from alternative splicing or posttranslational modification. Using the anti-SYNGAP antibody, the expression of SYNGAP in different tissues was examined. As with the Northern blot data. SYNGAP protein was found to be expressed exclusively in brain with high levels in the cortex and hippocampus and relatively low levels in cerebellum (FIG. 7C). SYNGAP was found to be selectively localized to membrane fractions and was resistant to Triton X-100. CHAPS. and RIPA extractions from synaptic plasma membranes (FIG. 7D) similar to other proteins associated with the PSD such as PSD-95/SAP90, SAP102, and the NMDA receptor (Cho, K. O., et al. (1992) Neuron, 9:929; Lau et al., supra 1996; Kim, E., et al. (1997) J. Cell. Biol. 136:669).

Figure 7D:
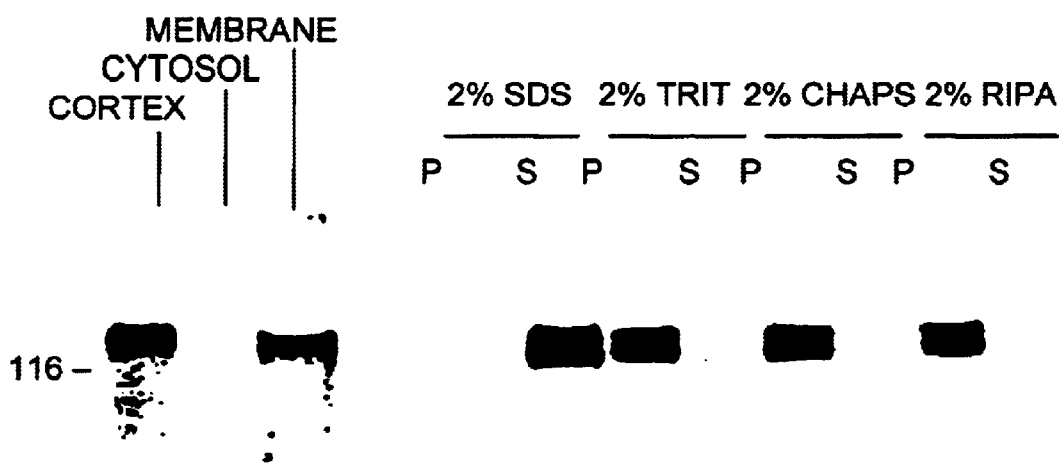
FIG. 7D is a representation of an immunoblot showing that rat brain cortex crude homogenates (cortex) and cytosolic and membrane fractions include membrane-associated SYNGAP. Cortical membranes were extracted with the indicated detergents and then separated into soluble (S) and pellet fractions (P) and the distribution of SYNGAP detected using immunoblot techniques. SYNGAP is resistant to membrane extraction with non-denaturing detergents similar to other proteins located in the PSD fraction.

FIGS. 7A–7D are more specifically described as follows: FIG. 7A Northern blot of SYNGAP mRNA shows high level of SYNGAP mRNA expression in brain. FIG. 7B: antibodies were generated against SYNGAP and used to identify SYNGAP in rat tissues using immunoblot techniques. These antibodies recognized a 130 kDa protein in HEK293T cells transfected with the SYNGAP cDNA (Lane 2) and in rat brain homogenates (Lane 3). The 130 kDa protein was not detected in mock transfected HEK293T cells (lane 1) and imumunorecognition of the 130 kDa protein in brain was blocked by preabsorbtion of the antibody with the antigen (Lane 4). FIG. 7C: immunoblots of rat tissues with the SYNGAP antibody demonstrates that the expression of the SYNGAP protein is brain specific. FIG. 7D: immunoblots of rat brain cortex crude homogenates (cortex) and cytosolic and membrane fractions demonstrate that SYNGAP is membrane-associated. Cortical membranes were extracted with the indicated detergents and then separated into soluble (S) and pellet fractions (P) and the distribution of SYNGAP detected using immunoblot techniques. SYNGAP is resistant to membrane extraction with non-denaturing detergents similar to other proteins located in the PSD fraction.

1. RNA Preparation and Northern Blot Analysis

Total RNA from various tissues of male Sprague Dawley rat at P14 was isolated with RNAzol (Tel-Test) according to the manufacturer's protocol. The RNA (10 μg per lane) was separated on 1.2% formaldehyde agarose gel, transferred onto GeneScreen Plus membrane (Du Pont NEN) and then hybridized with a [α-$^{32}$P]-dCTP labeled SalI/NotI fragment of the original yeast clone. The result was visualized using a phosphoimager cassette. The blot was stripped and rehybridized with radioactively labeled GAPDH (HindIII/BamHI fragment) DNA to ensure equal loading of RNA per lane.

EXAMPLE 4

SYNGAP Associates With PSD-95 and SAP102 in vivo

Figure 8:
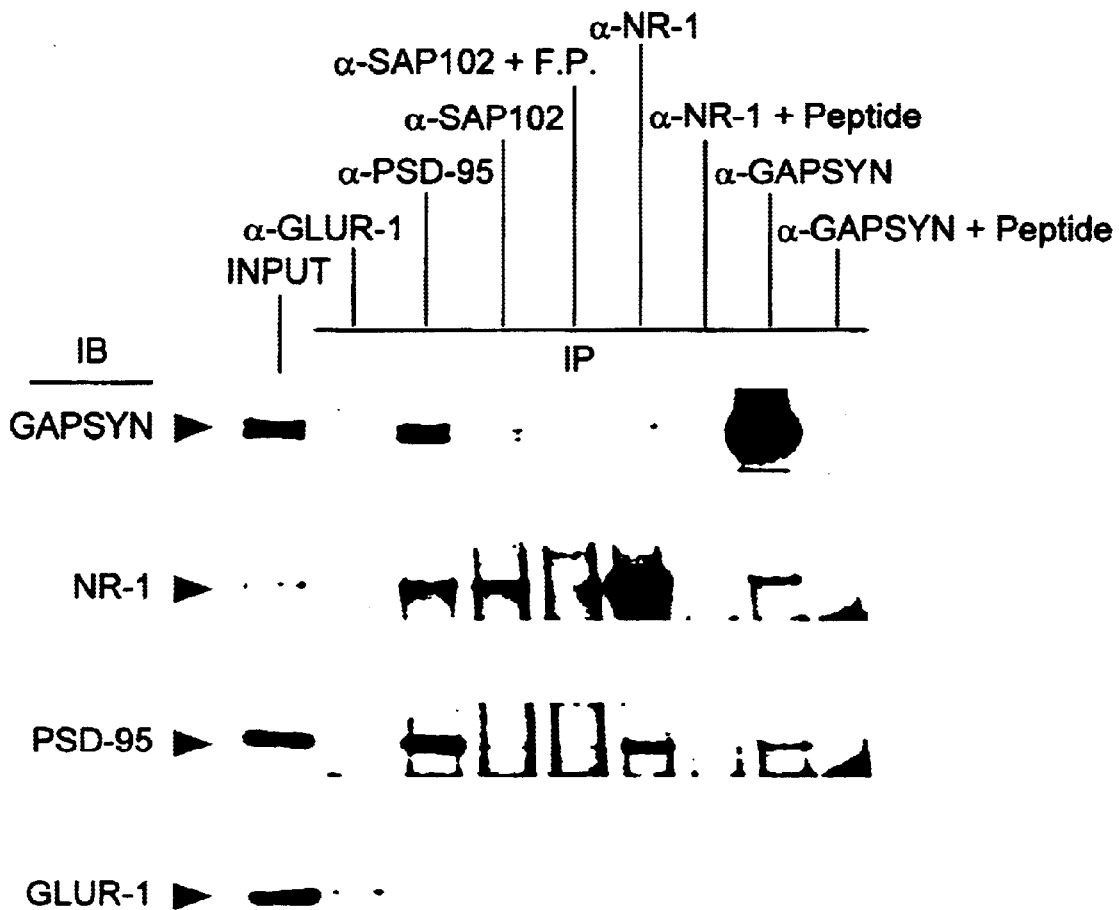
FIG. 8 is a representation of an immunoblot illustrating that SYNGAP is associated with the ONEIDA receptor complex. In this figure, immunoprecipitates were analyzed for the presence of SYNGAP, NMDAR1, PSD-95 and GluR1.

Interaction of SYNGAP, PSD-95/SAP90 and SAP102 was examined in the brain in vivo. As shown in FIG. 8, immunoprecipitation of PSD-95/SAP90 or SAP102 from deoxycholate solubilized brain membrane preparations resulted in the specific coimmunoprecipitation of SYNGAP. Moreover, using antibodies to the NR1 subunit of the NMDA receptor, SYNGAP was also found to be specifically associated with NMDA receptors (FIG. 8). Preabsorption of the SAP102 and NR1 antibodies with their antigens blocked the coimmunoprecipitation of SYNGAP confirming the specificity of the association. In contrast, SYNGAP did not coimmunoprecipitate with the NMDA receptor GluR1 subunit. These results strongly suggest that SYNGAP was associated with an NMDA receptor complex containing NMDA receptor subunits and PSD-95/SAP90 family members.

FIG. 8 is more specifically described as follows: Synaptic plasma membranes were solubilized with deoxycholate and the resulting deterrent extract (input) was used to immunoprecipitation the indicated proteins (IP). The immunoprecipitates were then analyzed for the presence of SYNGAP, NMDAR1, PSD-95 and GluR1 by immunoblot techniques as indicated above.

1. Brain Membrane Preparation and Solubilization

Membrane preparations (P2) and solubilization was carried out according to the procedures described by Luo et al. (1997) with modifications. Cortex and hippocampus from a male Sprague-Dawley rat, age of 4 to 6 weeks were homogenized twice using a glass-Teflon homogenizer with protease inhibitors (antipain, chymotrypsin, leupeptin, Trasylol, 0.1 mM PMSF). After determining the protein concentration of the P2 fraction by a Coomasie assay (Pierce), aliquots of the proteins at 3 mg/ml were stored at −80° C. until use. For coimmunoprecipitation, PA (300 μg per IP) was solubilized by 1.0% sodium deoxycholate followed by 0.1% Triton X-100 and the preparation was centrifuged for 10 minutes at 100,000×g. The supernatant was then used for coimmunoprecipitation.

For detergent extraction of SYNGAP, synaptic plasma membranes were prepared and solubilized using various detergents, SDS, Triton X-100, CHAPS, and RIPA, according to the procedure described by Lau et al. supra.

EXAMPLE 5

Detection of SYNGAP at Specific Synapses

Figure 9A:
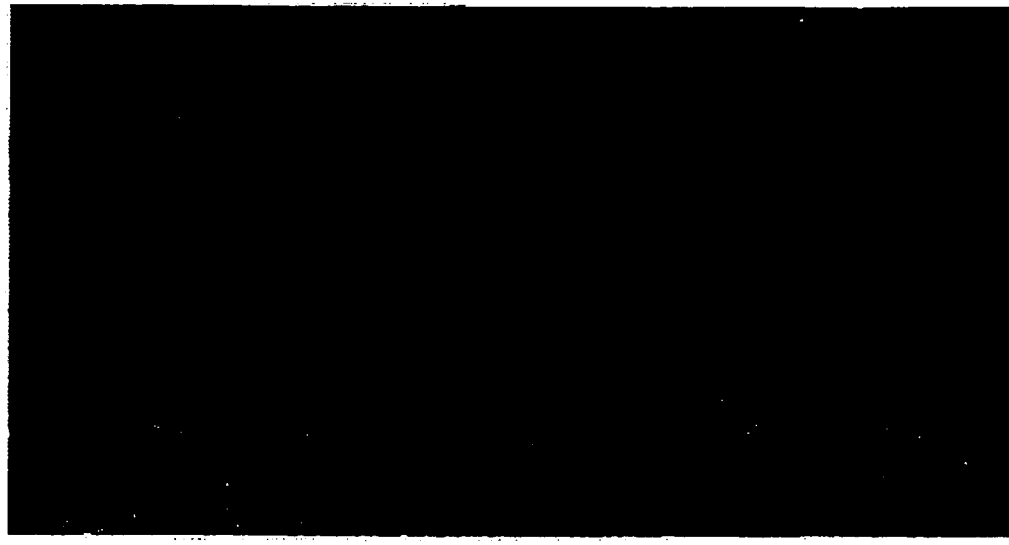
FIGS. 9A–9F are representations of photomicrogaphs showing that SYNGAP is localized to synapses.
Figure 9B:
Figure 9C:
Figure 9D:
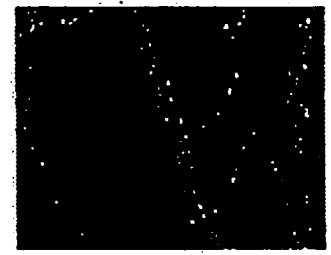
Figure 9E:
Figure 9F:

The subcellular distribution of SYNGAP in neurons was examined in low density hippocampal cultures using the anti-SYNGAP antibody. SYNGAP was expressed in the cell body of neurons but the pattern of immunoreactivity was strikingly punctuate along the processes of the neurons, suggesting that SYNGAP may be localized to synapses (FIG. 9A). Double labeling the hippocampal neurons with antibodies against SYNGAP and the synaptic marker protein synaptophysin demonstrated that SYNGAP is specifically localized to synapses (FIGS. 9B–9D). The staining of the neurons with the SYNGAP antibody was blocked by pre-absorption of the antibody with the antigenic peptide confirming the specificity of the antibody (FIGS. 9E–9F).

As noted above in Example 3, SYNGAP associated with PSD-95 and SAP102 in vivo. Next, the colocalization of the PSD95/SAP90 family members with SYNGAP was examined. It was found that SYNGAP colocalized with PSD-95 (FIGS. 10A–10I). This observation provides additional support for SYNGAP association with PSD-95.

To determine whether SYNGAP is localized to both excitatory and inhibitory synapses, neurons were double labeled with SYNGAP antibodies and antibodies against the NR1 subunit of the NMDA receptor to label excitatory synapses or anti-glutamatic acid decarboxylase (GAD) antibodies to label inhibitory synapses. As shown in FIG. 5B SYNGAP colocalized with NMDA receptors and was present at all excitatory synapses. In contrast, SYNGAP was not observed at GABAergic synapses (FIGS. 10G–10I).

FIGS. 9A–9F are more particularly explained as follows: FIG. 9A: low density hippocampal cultures were stained with the SYNGAP antibody and visualized with a Rhodamine-coupled secondary antibody. SYNGAP is present in the cell soma and is clustered on the neuronal processes. FIGS. 9B–9D: double labeling of the hippocampal cultures with antibodies against SYNGAP and the synaptic marker synaptophysin demonstrates that SYNGAP is synaptically localized FIGS. 9E–9F: the staining of the hippocampal neurons with the SYNGAP antibody is specifically blocked by preincubation of the antibody with the antigen. The right panel shows that the double labeling with anti-synaptophysin antibody is not blocked by the SYNGAP antigen.

Figure 10C:
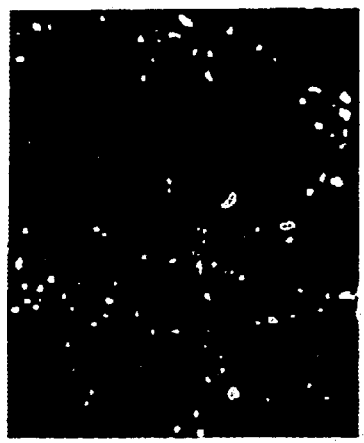
FIGS. 10A–10I are representations of photomicrographs showing that SYNGAP is specifically localized to excitatory synapses.
Figure 10B:
Figure 10A:
Figure 10D:
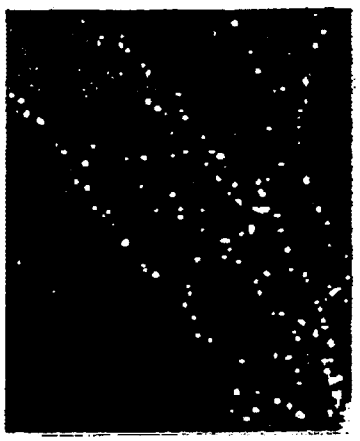
Figure 10G:
Figure 10E:
Figure 10H:
Figure 10F:
Figure 10I:

FIGS. 10A–10I are also more particularly described as follows: FIGS. 10A–10C: double labeling of hippocampal neurons with antibodies against SYNGAP and PSD-95 demonstrates that SYNGAP and PSD-95 are colocalized in the neurons. FIGS. 10D–10F: SYNGAP exists exclusively at excitatory synapses as shown by the colocalization of SYNGAP with the NR1 subunit of the NMDA receptor. FIGS. 10G–10I: to exclude the possibility that SYNGAP is found at inhibitory synapses, the hippocampal neurons were double labeled with the antibodies to SYNGAP and the GABAergic synaptic marker GAD. GAD staining does not overlap with the expression pattern of SYNGAP.

EXAMPLE 6

SYNGAP has Ras-GAP Activity

Figure 11:
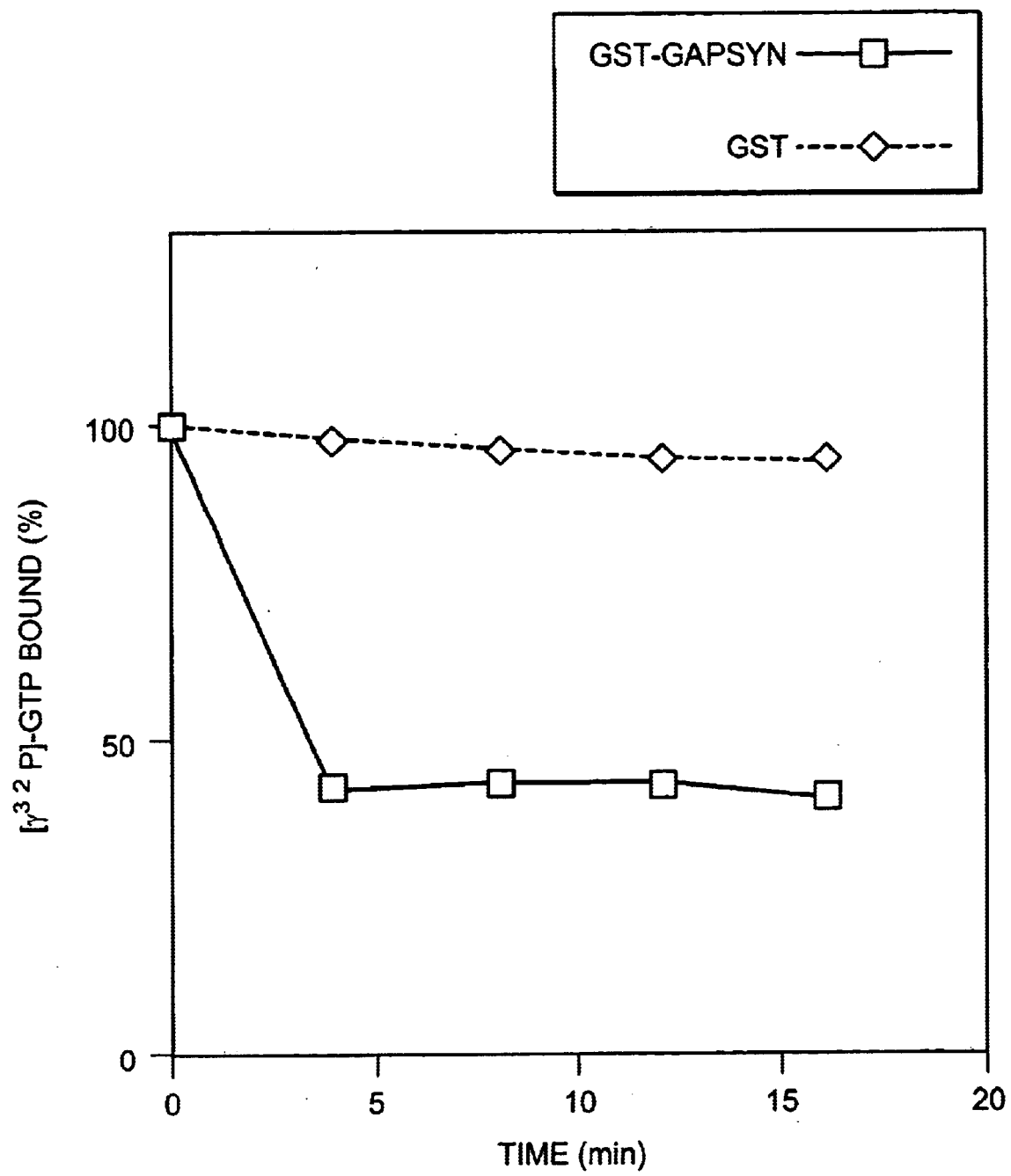
FIG. 11 is a graph showing that the GAP domain of SYNGAP stimulates H-Ras GTPase activity.

SYNGAP shows homology with the GAP domain of rasGAPs suggesting that SYNGAP may regulate the GTPase activity of Ras (Boguski and McCormick, (1993) Nature 366: 643). A glutathione S-transferase (GST) fusion protein of the rasGAP domain of SYNGAP was made and incubated with a purified H-ras GST fusion protein in the presence of $[\gamma\text{-}^{32}P]$-GTP. It was found that GST-ras fusion proteins exhibited a low intrinsic GAP activity in the absence of a rasGAP (FIG. 1). In contrast, addition of the GST fusion protein of the GAP domain of SYNGAP dramatically stimulated the GTPase activity of Ras (FIG. 11). Control GST-backbone protein FIG. 11) or a GST-SAP102 fusion protein had no effect on ras-GTPase activity.

1. Fusion Protein Construction and Preparation

The first 119 amino acids of SAP102 was amplified by PCR and subcloned in frame into pTrcHisB vector (Invitrogen) via the BamHI and EcoRI restriction digest sites. The construct was then transformed into BL21 bacteria and following an induction of expression with IPTG. The protein was purified in a denaturing condition according to the protocol provided by the QIA-expressionist (Qiagen). The GAP domain (266–521) subcloned into pGEX-4T2 and a GST-Ras fusion protein was obtained and expressed in BL21 cells. The fusion protein was purified using glutathione coupled agarose. All of the above proteins were analyzed by SDS-PAGE followed by Coomassie Blue Staining.

2. GAP Assay

The GAP assay was performed following the methods described by Settleman et al. (1992) supra with modifications. Briefly, 0.5 to 1 μM of GST-Ras was incubated with nM $[\gamma\text{-}^{32}P]$-GT (6,000 Ci/mmol, Du Pont-NEN) in 50 mM Tris, pH 7.5, 50 mM NaCl, 1 mM EDTA, 1 mg/ml BSA, and 1 mM DTT for 10 minutes at room temp. GST-GAP or control GST fusion protein (200 ng) was then added in 50 mM Tris, pH 7.5, 5 mM $MgCl_2$, 1 mhI DTT and incubated for the indicated times. After stopping the reaction (by adding 5 volumes of ice-cold 50 mM Tris, pH 7.5, 5 mM $MgCl_2$; 1 mM DTT), the mixture was filtered through HA membranes (Millipore) and the filters were counted for $^{32}P$ in scintillation cocktail.

Results of the GAP assay are shown in FIG. 11. Time course of the GTPase activity of GST H-Ras fusion protein in the presence and absence of the GAP domain of SYNGAP. Incubation of a GST-ras fusion protein with a control GST fusion protein (--◊--) had little effect on the slow intrinsic GTPase activity or GST-Ras. In contrast, addition of the GST-fusion protein containing the GAP domain of SYNGAP dramatically stimulated the GTPase activity of GST-Ras (-□-).

EXAMPLE 7

Generation and Purification of SYNGAP and SAP102 Antibodies

The last 20 amino acids of SYNGAP (KRLLDAQRGSFPPWVQQTRV (SEQ ID NO. 20) were synthesized and purified. The protocol for generation and purification of polyclonal antibody was described by Blackstone et al. (Blackstone et at., 1992 supra). Briefly, the peptide was crosslinked to thyroglobulin with glutaraldehyde and injected into New Zealand white rabbits to generate antiserum (Covance). The antiserum was then purified with Affi-Gel 10 resin (Bio-Rad) coupled to BSA covalently bound to the peptides (Lau et al., (1996), supra). The N-terminal SAP102 fusion protein with hexahistidine tag was immunized similarly to generate a polyclonal rabbit antibody and the antiserum was purified using the antigen coupled to Affi-Gel 10.

1. Coimmunoprepitation and Immunoblotting

To affinity purified antibodies, about 1 to 2 µg were preincubated with 50 µl of 1:1 slurry of protein A-Sepharose for 1 hour and the protein A-antibody complex was spun down at 2000 rpm for 2 minutes. The clarified supernatant of solubilized P2 fraction was then added to the sepharose beads and the mixture incubated for 2 to 3 hours at 4° C. The mixture was washed once with 1% Triton X-100 in immunoprecipitation buffer (137 mM NaCl, 2.7 mM KCl, 4.3 mM $Na_2HPO_4$, 1.4 mM $KH_2PO_4$, 5 mM EDTA, 5 mM EGTA, 1 mM sodium vanadate. 10 mM sodium pyrophosphate, 50 mM NaF, 20 units/ml Trasylol and 0.1 mM phenylmethylsulfonyl fluoride), twice with 1% Triton X-100 in immunoprecipitation buffer plus 300 mM NaCl, and three times with immunoprecipitation buffer. The proteins were eluted by Laemmli sample buffer (Laemmli, 1970) and were separated by SDS-PAGE. The gel was transferred to a PVDF (Millipore) membrane and the membrane was blocked and immununoblotted as described by Lau et al. (1996), supra. When the antibodies were blocked with antigens, they were preincubated with the peptide at concentration of 100 µg/ml or fusion proteins at concentration of 50 µg/ml. The antibodies used in the experiments have been previously described: anti-NR1a C-terminal antibody (Tingley, W. G., et al. (1993) Nature. 364:70), anti-GluR1 C-terminal antibody (Blackstone et al., 1990), anti-NR2B C-terminal antibody (Lau, L. F., and Huganir, R. L. (1995) J. Biol. Chem. 270:20036), and anti-PSD-95 antibody (Gift from Dr. J. S. Trimmer)

2. Immunocytochemistry

Low density hippocampal neuronal culture was performed following the procedure described by Goslin and Banker (Goslin and Banker, 1991). After 13 to 90 days in culture, the neurons were fixed and stained with affinity purified antibodies as previously described with minor modifications (Lau and Huganir, 1995 supra; O'Brien, R. J., et al. (1997) J. Neurosci. 17:7339; Rao, A. and Craig, M. (1997) Neuron. 19:801).

Examples 1 to 8 show the isolation and characterization SYNGAP, a novel synaptic rasGAP that directly interacts with the PSD-95/SAP90 family of proteins. SYNGAP is highly expressed in brain, is not detected in other tissues and is especially abundant in the cortex, hippocampus, and olfactory bulb. SYNGAP is found exclusively at excitatory synapses in hippocampal neurons in culture. The SYNGAP protein is tightly associated with synaptic membranes, and exists as two or more alternate forms. Due to its synaptic localization and association with the PSD it is uniquely positioned to regulate signal transduction events that may involve ras signaling pathways at excitatory synapses.

EXAMPLE 8

Isolation of Human SYNGAP

It is possible to isolate Homo sapiens SYNGAP in accord with the present disclosure. For example, in one approach, the SYNGAP can be obtained by screening a human brain cDNA γZAP phage library (Stratagene) at high stringency conditions. More particularly, the hybridization can be carried out by incubation at 65° C. overnight in 0.08 Na phosphate, pH 6.8, 0.05 mNa citrate, 0.5 mNaCl, 5×Denhardt's solution, 0.5% SDS, 0.1 mg/ml salmon sperm DNA with a probe concentration of about 0.4 million CPM/ml. A preferred probe can be made by standard methods from any of the Rattus norvegicus SYNGAP DNA sequences shown in SEQ ID Nos. 1–2, 4–5, or 7–8. Especially preferred probes have a length between about 500 to about 2000 bases. Such probes are typically restriction fragments that can be readily obtained by restriction enzyme digestion of a desired SYNGAP cDNA followed by purification of the fragment. Typically, the fragment is detectably-labeled, e.g., with $^{32}P$ to facilitate screening. The homology of the clone isolated between the two different species (i.e. rat and human) can be compared: an identity of 70 to 80% may be observed at the DNA sequence level. At the protein, about 70 to about 90% identity may be observed across a substantial length of the human gene. The isolated human clone can be analyzed in accordance with the SYNGAP sequences disclosed herein to identify mRNA expression pattern, GAP activity, and/or participation in a MAP kinase cascade.

The examples also show that SYNGAP has an organized and domain structure which is involved in the regulation of its GAP activity. In addition to the ras-GAP domain the amino terminus contains a region that is partially homologous to pleckstrin homology (PH) domains, a phospholipid binding module of about 100 amino acids that binds polyphosphatidylinositides which is thought to serve as a signal dependent membrane adaptor (Shaw, G. (1996) Bioessays. 18:35). The N-terminal region also contains a C2 domain which has been shown to be involved in the binding of $Ca^{2+}$ in a phospholipid-dependent manner (Luo, J. H., and Weinstein, I. B. (1993) J. Biol. Chem. 268:23580) in protein kinase C, synaptotagmin and rabphilin-3A (Nishizuka Y. (1988) Nature. 334:661; Perin, M. S., et al. (1991) J. Biol. Chem. 266:623; Yamaguchi, et al., (1993) J. Biol. Chem. 268:27164). C2 domains have also been found in other rasGAPs such as human p120GAP and GAP1$^{IP4BP}$ (Cullen. P. J., et al. (1995) Nature. 376:527). The presence of these two domains suggests that SYNGAP may respond to changes in $Ca^{2+}$ and phospholipid second messengers. The association of SYNGAP with the NMDA receptor complex suggests that SYNGAP may specifically respond to changes in $Ca^{2+}$ mediated by activation of NMDA receptors. The C-terminal half of SYNGAP also contains potential regulatory domains including many consensus phosphorylation sites for CaMKII and protein tyrosine kinases. CaMKII is very abundant in the postsynaptic density and has been implicated as having a key role in the modulation of synaptic plasticity (Nicoll, R. A. and Malenka, R. C. (1995) Nature. 377:115). In addition. SYNGAP has ten consecutive histidine residues which may bind divalent transition metals such as $Zn^{2+}$ and $Cu^{2+}$ and play some role in the regulation of SYNGAP function.

The in vivo association of SYNGAP with the NMDA receptor complex and PSD-95 and SAP 102 suggests that SYNGAP plays a specific role in the modulation of ras signaling at excitatory synapses. The specific localization of SYNGAP to excitatory synapses suggests that SYNGAP may play a critical role in the regulation of BDNF signaling in the postsynaptic membrane.

The identification of SYNGAP as a PSD-95 associated protein provides the first evidence that the PSD-95/SAP90 family forms a complex with signal transduction molecules involved in the ras pathway and suggest that ras plays specific roles in the regulation of excitatory synaptic transmission at the postsynaptic membrane. SYNGAP may also regulate ras signaling in response to $Ca^{2+}$.

The invention has been described in detail with reference to preferred embodiments thereof. However, it will be appreciated that those skilled in the art, upon consideration of this disclosure, may make modification and improvements within the spirit and scope of the invention as set forth in the following claims. All references and patent publications cited herein are firmly incorporated herein by reference.

What is claimed is:

1. An isolated polynucleotide encoding a mammalian Synaptic GTPase Activating Protein (SYNGAP), wherein the polynucleotide comprises the sequence of any one of SEQ ID Nos. 1, 3, or 5.

* * * * *